US009522217B2

(12) United States Patent
Kutryk et al.

(10) Patent No.: US 9,522,217 B2
(45) Date of Patent: *Dec. 20, 2016

(54) MEDICAL DEVICE WITH COATING FOR CAPTURING GENETICALLY-ALTERED CELLS AND METHODS FOR USING SAME

(75) Inventors: Michael J. B. Kutryk, York (CA); Robert J. Cottone, Jr., Davie, FL (US); Stephen M. Rowland, Miami, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 245 days.

This patent is subject to a terminal disclaimer.

(21) Appl. No.: 10/835,767

(22) Filed: Apr. 30, 2004

(65) Prior Publication Data
US 2005/0025752 A1 Feb. 3, 2005

Related U.S. Application Data

(63) Continuation-in-part of application No. 10/360,567, filed on Feb. 6, 2003, now abandoned, and a continuation-in-part of application No. 09/808,867, filed on Mar. 15, 2001, now Pat. No. 7,037,332.

(60) Provisional application No. 60/189,674, filed on Mar. 15, 2000, provisional application No. 60/201,789, filed on May 4, 2000.

(51) Int. Cl.
| | |
|---|---|
| A01N 63/00 | (2006.01) |
| C12N 5/071 | (2010.01) |
| C12N 15/00 | (2006.01) |
| A61F 2/04 | (2013.01) |
| A61L 27/08 | (2006.01) |
| A61L 27/30 | (2006.01) |
| A61L 27/44 | (2006.01) |
| A61L 27/54 | (2006.01) |
| A61L 29/10 | (2006.01) |
| A61L 29/12 | (2006.01) |
| A61L 29/16 | (2006.01) |
| A61L 31/08 | (2006.01) |
| A61L 31/10 | (2006.01) |
| A61L 31/12 | (2006.01) |
| A61L 31/16 | (2006.01) |
| B82Y 30/00 | (2011.01) |

(52) U.S. Cl.
CPC ............. *A61L 27/08* (2013.01); *A61L 27/303* (2013.01); *A61L 27/44* (2013.01); *A61L 27/54* (2013.01); *A61L 29/103* (2013.01); *A61L 29/126* (2013.01); *A61L 29/16* (2013.01); *A61L 31/084* (2013.01); *A61L 31/10* (2013.01); *A61L 31/125* (2013.01); *A61L 31/16* (2013.01); *B82Y 30/00* (2013.01); *A61L 2300/258* (2013.01); *A61L 2300/45* (2013.01)

(58) Field of Classification Search
CPC ............ A61K 47/48992; A61K 48/005; C12N 5/0692; A61L 31/16; A61L 31/10; A61L 31/084; A61L 29/16; A61L 29/085; A61L 27/54; A61L 27/34; A61L 27/3808; A61L 27/303; A61L 27/10
USPC ....................................... 424/93.21
See application file for complete search history.

(56) References Cited

U.S. PATENT DOCUMENTS

| | | | |
|---|---|---|---|
| 3,523,807 | A | 8/1970 | Gerendas |
| 3,880,149 | A | 4/1975 | Kawaguchi |
| 4,115,537 | A | 9/1978 | Driscoll et al. |
| 4,344,934 | A | 8/1982 | Martin et al. |
| 4,355,426 | A | 10/1982 | MacGregor |
| 4,487,715 | A | 12/1984 | Nitecki et al. |
| 4,515,160 | A | 5/1985 | Keimel |
| 4,539,198 | A | 9/1985 | Powell et al. |
| 4,548,736 | A | 10/1985 | Muller et al. |
| 4,553,542 | A | 11/1985 | Schenck et al. |
| 4,553,974 | A | 11/1985 | Dewanjee |
| 4,587,258 | A | 5/1986 | Gold et al. |
| 4,738,740 | A | 4/1988 | Pinchuk et al. |

(Continued)

FOREIGN PATENT DOCUMENTS

| | | |
|---|---|---|
| CA | 2260532 | 8/1999 |
| CA | 2472031 | 8/2003 |

(Continued)

OTHER PUBLICATIONS

Dekker et al., 1991, Thrombosis and Haemostasis 66:715-724.*

(Continued)

*Primary Examiner* — Christopher M Babic
*Assistant Examiner* — Kelaginamane T Hiriyanna
(74) *Attorney, Agent, or Firm* — Leason Ellis LLP

(57) ABSTRACT

Therapeutic and drug delivery systems are provided in the form of medical devices with coatings for capturing and immobilizing target cells such as circulating progenitor or genetically-altered mammalian cells in vivo. The genetically-altered cells are transfected with genetic material for expressing a marker gene and a therapeutic gene in a constitutively or controlled manner. The marker gene is a cell membrane antigen not found in circulating cells in the blood stream and therapeutic gene encodes a peptide for the treatment of disease, such as, vascular disease and cancer. The coating on the medical device may be a biocompatible matrix comprising at least one type of ligand, such as antibodies, antibody fragments, other peptides and small molecules, which recognize and bind the target cells. The therapeutic and/or drug delivery systems may be provided with a signal source such as activator molecules for stimulating the modified cells to express and secrete the desired marker and therapeutic gene products.

16 Claims, 21 Drawing Sheets

(56) References Cited

U.S. PATENT DOCUMENTS

| | | |
|---|---|---|
| 4,743,252 A | 5/1988 | Martin et al. |
| 4,795,459 A | 1/1989 | Jauregue |
| 4,804,382 A | 2/1989 | Turina et al. |
| 4,886,062 A | 12/1989 | Wiktor et al. |
| 4,920,016 A | 4/1990 | Allen et al. |
| 4,920,203 A | 4/1990 | Tang |
| 4,967,734 A | 11/1990 | Rennex |
| 5,011,778 A | 4/1991 | Newman et al. |
| 5,043,165 A | 8/1991 | Radhakrishnan |
| 5,059,166 A | 10/1991 | Fischell et al. |
| 5,059,211 A | 10/1991 | Stack et al. |
| 5,061,722 A | 10/1991 | Teetz et al. |
| 5,102,417 A | 4/1992 | Palmaz |
| 5,145,945 A | 9/1992 | Tang et al. |
| 5,152,758 A | 10/1992 | Kaetsu et al. |
| 5,152,781 A | 10/1992 | Tang |
| 5,160,341 A | 11/1992 | Brenneman |
| 5,198,263 A | 3/1993 | Stafford et al. |
| 5,199,939 A | 4/1993 | Dake et al. |
| 5,199,942 A | 4/1993 | Gillis |
| 5,213,580 A | 5/1993 | Slepian et al. |
| 5,225,204 A | 7/1993 | Chen et al. |
| 5,246,445 A | 9/1993 | Yachia et al. |
| 5,254,113 A | 10/1993 | Wilk |
| 5,256,764 A | 10/1993 | Tang et al. |
| 5,274,074 A | 12/1993 | Tang et al. |
| 5,276,732 A | 1/1994 | Stent et al. |
| 5,288,711 A | 2/1994 | Mitchell et al. |
| 5,292,321 A | 3/1994 | Lee |
| 5,292,813 A | 3/1994 | Patil et al. |
| 5,302,168 A | 4/1994 | Hess |
| 5,304,121 A | 4/1994 | Sahatjian |
| 5,306,286 A | 4/1994 | Stack et al. |
| 5,310,669 A | 5/1994 | Richmond et al. |
| 5,324,261 A | 6/1994 | Amundson et al. |
| 5,338,571 A | 8/1994 | Mirkin et al. |
| 5,342,348 A | 8/1994 | Kaplan |
| 5,358,677 A | 10/1994 | Muth et al. |
| 5,366,504 A | 11/1994 | Anderson et al. |
| 5,370,614 A | 12/1994 | Amundson et al. |
| 5,372,600 A | 12/1994 | Beyar et al. |
| 5,376,376 A | 12/1994 | Li |
| 5,412,068 A | 5/1995 | Tang |
| 5,417,699 A | 5/1995 | Klein et al. |
| 5,419,760 A | 5/1995 | Narciso |
| 5,423,885 A | 6/1995 | Williams |
| 5,429,634 A | 7/1995 | Narciso |
| 5,439,446 A | 8/1995 | Barry |
| 5,441,515 A | 8/1995 | Khosravi et al. |
| 5,443,458 A | 8/1995 | Eury |
| 5,443,496 A | 8/1995 | Schwartz et al. |
| 5,443,498 A | 8/1995 | Fontaine |
| 5,449,382 A | 9/1995 | Dayton |
| 5,464,450 A | 11/1995 | Buscemi et al. |
| 5,464,650 A | 11/1995 | Berg et al. |
| 5,470,307 A | 11/1995 | Lindall |
| 5,486,593 A | 1/1996 | Tang et al. |
| 5,489,297 A | 2/1996 | Duran |
| 5,492,890 A | 2/1996 | Ginsberg et al. |
| 5,502,158 A | 3/1996 | Sinclair |
| 5,503,635 A | 4/1996 | Sauer et al. |
| 5,510,077 A | 4/1996 | Dinh et al. |
| 5,527,322 A | 6/1996 | Klein et al. |
| 5,527,337 A | 6/1996 | Stack |
| 5,536,641 A | 7/1996 | Sanz-Moncasi et al. |
| 5,545,208 A | 8/1996 | Wolff et al. |
| 5,551,954 A | 9/1996 | Buscemi |
| 5,554,182 A | 9/1996 | Dinh et al. |
| 5,558,903 A | 9/1996 | Bhushan et al. |
| 5,569,295 A | 10/1996 | Lam |
| 5,571,166 A | 11/1996 | Dinh et al. |
| 5,578,046 A | 11/1996 | Liu et al. |
| 5,588,962 A | 12/1996 | Nicholas et al. |
| 5,591,224 A | 1/1997 | Schwartz et al. |
| 5,591,227 A | 1/1997 | Dinh et al. |
| 5,593,434 A | 1/1997 | Williams |
| 5,599,352 A | 2/1997 | Dinh et al. |
| 5,603,720 A | 2/1997 | Kieturakis |
| 5,605,696 A | 2/1997 | Eury et al. |
| 5,611,794 A | 3/1997 | Sauer et al. |
| 5,613,981 A | 3/1997 | Boyle et al. |
| 5,618,299 A | 4/1997 | Khosravi et al. |
| 5,624,411 A | 4/1997 | Tuch |
| 5,626,611 A | 5/1997 | Liu et al. |
| 5,628,785 A | 5/1997 | Schwartz et al. |
| 5,629,077 A | 5/1997 | Turnlund et al. |
| 5,632,840 A | 5/1997 | Campbell |
| 5,634,936 A | 6/1997 | Linden et al. |
| 5,634,946 A | 6/1997 | Slepian et al. |
| 5,635,386 A | 6/1997 | Palsson et al. |
| 5,635,482 A | 6/1997 | Bhatnagar |
| 5,637,113 A | 6/1997 | Tartaglia et al. |
| 5,641,466 A | 6/1997 | Ebbsen et al. |
| 5,649,952 A | 7/1997 | Lam |
| 5,649,977 A | 7/1997 | Campbell |
| 5,658,894 A | 8/1997 | Weisz |
| 5,661,127 A | 8/1997 | Bhatnagar et al. |
| 5,662,712 A | 9/1997 | Pathak et al. |
| 5,670,161 A | 9/1997 | Healy |
| 5,674,192 A | 10/1997 | Sahatjian et al. |
| 5,674,241 A | 10/1997 | Bley et al. |
| 5,674,276 A | 10/1997 | Andersen et al. |
| 5,674,287 A | 10/1997 | Slepian et al. |
| 5,674,722 A | 10/1997 | Mulligan et al. |
| 5,674,848 A | 10/1997 | Bhatnagar |
| 5,676,685 A | 10/1997 | Razavi |
| 5,677,180 A | 10/1997 | Robinson et al. |
| 5,679,400 A | 10/1997 | Tuch |
| 5,681,559 A | 10/1997 | DiGiusto et al. |
| 5,685,847 A | 11/1997 | Barry |
| 5,688,486 A | 11/1997 | Watson et al. |
| 5,697,943 A | 12/1997 | Sauer et al. |
| 5,697,967 A | 12/1997 | Dinh et al. |
| 5,700,286 A | 12/1997 | Tartaglia |
| 5,707,385 A | 1/1998 | Williams |
| 5,709,713 A | 1/1998 | Evans et al. |
| 5,718,159 A | 2/1998 | Thompson |
| 5,721,108 A | 2/1998 | Robinson et al. |
| 5,725,567 A | 3/1998 | Wolff et al. |
| 5,733,327 A | 3/1998 | Igaki |
| 5,733,330 A | 3/1998 | Cox |
| 5,733,925 A | 3/1998 | Kunz et al. |
| 5,741,323 A | 4/1998 | Pathak et al. |
| 5,746,755 A | 5/1998 | Wood et al. |
| 5,749,915 A | 5/1998 | Slepian |
| 5,749,922 A | 5/1998 | Slepian et al. |
| 5,753,088 A | 5/1998 | Olk et al. |
| 5,755,772 A | 5/1998 | Evans et al. |
| 5,758,562 A | 6/1998 | Thompson |
| 5,762,625 A | 6/1998 | Igaki |
| 5,766,239 A | 6/1998 | Cox |
| 5,766,710 A | 6/1998 | Turnlund |
| 5,769,883 A | 6/1998 | Buscemi |
| 5,770,609 A | 6/1998 | Grainger et al. |
| 5,772,992 A | 6/1998 | Bauer |
| 5,776,184 A | 7/1998 | Tuch |
| 5,779,719 A | 7/1998 | Klein et al. |
| 5,780,436 A | 7/1998 | Bhatnagar et al. |
| 5,782,838 A | 7/1998 | Beyar et al. |
| 5,782,903 A | 7/1998 | Wiktor |
| 5,788,979 A | 8/1998 | Alt |
| 5,792,152 A | 8/1998 | Klein et al. |
| 5,800,507 A | 9/1998 | Schwartz |
| 5,800,521 A | 9/1998 | Orth |
| 5,800,538 A | 9/1998 | Slepian et al. |
| 5,800,836 A | 9/1998 | Morella et al. |
| 5,811,447 A | 9/1998 | Kunz et al. |
| 5,820,917 A | 10/1998 | Tuch |
| 5,824,048 A | 10/1998 | Tuch |
| 5,824,049 A | 10/1998 | Ragheb et al. |
| 5,830,217 A | 11/1998 | Ryan |
| 5,830,760 A | 11/1998 | Tsai et al. |
| 5,833,651 A | 11/1998 | Donovan et al. |
| 5,834,582 A | 11/1998 | Sinclair |

(56) References Cited

U.S. PATENT DOCUMENTS

| | | |
|---|---|---|
| 5,837,008 A | 11/1998 | Berg et al. |
| 5,843,089 A | 12/1998 | Sahatjian et al. |
| 5,843,168 A | 12/1998 | Dang |
| 5,843,172 A | 12/1998 | Yan |
| 5,843,633 A | 12/1998 | Yin et al. |
| 5,849,034 A | 12/1998 | Schwartz |
| 5,849,035 A | 12/1998 | Pathak et al. |
| 5,851,217 A | 12/1998 | Wolff et al. |
| 5,851,230 A | 12/1998 | Weadock et al. |
| 5,851,231 A | 12/1998 | Wolff et al. |
| 5,857,998 A | 1/1999 | Barry |
| 5,860,991 A | 1/1999 | Klein et al. |
| 5,865,723 A | 2/1999 | Love |
| 5,865,814 A | 2/1999 | Tuch |
| 5,868,719 A | 2/1999 | Tsukernik |
| 5,871,437 A | 2/1999 | Alt |
| 5,871,475 A | 2/1999 | Frassica |
| 5,871,535 A | 2/1999 | Wolff |
| 5,873,904 A | 2/1999 | Ragheb et al. |
| 5,874,419 A | 2/1999 | Herrmann et al. |
| 5,879,697 A | 3/1999 | Ding et al. |
| 5,880,090 A | 3/1999 | Hammond et al. |
| 5,891,192 A | 4/1999 | Murayama et al. |
| 5,891,558 A | 4/1999 | Bell et al. |
| 5,893,840 A | 4/1999 | Hull et al. |
| 5,893,867 A | 4/1999 | Bagaoisan et al. |
| 5,895,420 A | 4/1999 | Mirsch |
| 5,897,911 A | 4/1999 | Loeffler |
| 5,902,311 A | 5/1999 | Andreas et al. |
| 5,902,799 A | 5/1999 | Herrmann et al. |
| 5,906,573 A | 5/1999 | Aretz |
| 5,906,631 A | 5/1999 | Imran |
| 5,912,177 A | 6/1999 | Turner et al. |
| 5,916,234 A | 6/1999 | Lam |
| 5,916,585 A | 6/1999 | Cook et al. |
| 5,921,994 A | 7/1999 | Andreas et al. |
| 5,925,353 A | 7/1999 | Mosseri |
| 5,935,506 A | 8/1999 | Schmitz |
| 5,935,940 A | 8/1999 | Weisz |
| 5,945,457 A | 8/1999 | Plate et al. |
| 5,947,977 A | 9/1999 | Slepian et al. |
| 5,951,586 A | 9/1999 | Berg et al. |
| 5,954,693 A | 9/1999 | Barry |
| 5,954,706 A | 9/1999 | Sahatjiam |
| 5,955,105 A | 9/1999 | Mitra et al. |
| 5,957,938 A | 9/1999 | Zhu et al. |
| 5,957,971 A | 9/1999 | Schwartz |
| 5,957,974 A | 9/1999 | Thompson |
| 5,957,975 A | 9/1999 | Lafont |
| 5,958,428 A | 9/1999 | Bhatnagar |
| 5,958,979 A | 9/1999 | Lahr et al. |
| 5,961,547 A | 10/1999 | Razavi |
| 5,964,771 A | 10/1999 | Beyar et al. |
| 5,968,070 A | 10/1999 | Bley et al. |
| 5,968,091 A | 10/1999 | Pinchuk |
| 5,968,092 A | 10/1999 | Buscemi |
| 5,972,029 A | 10/1999 | Fuisz |
| 5,976,161 A | 11/1999 | Kirsch et al. |
| 5,976,181 A | 11/1999 | Whelan et al. |
| 5,976,182 A | 11/1999 | Cox |
| 5,980,551 A | 11/1999 | Summers |
| 5,980,564 A | 11/1999 | Stinson |
| 5,980,565 A | 11/1999 | Jayaraman |
| 5,980,566 A | 11/1999 | Alt |
| 5,980,887 A * | 11/1999 | Isner ............... A61K 45/06 424/85.1 |
| 5,980,972 A | 11/1999 | Ding |
| 5,981,568 A | 11/1999 | Kunz et al. |
| 5,984,963 A | 11/1999 | Ryan |
| 5,990,378 A | 11/1999 | Ellis |
| 5,993,374 A | 11/1999 | Kick |
| 5,994,444 A | 11/1999 | Trescony et al. |
| 5,997,468 A | 12/1999 | Wolff et al. |
| 5,997,563 A | 12/1999 | Kretzers |
| 6,004,346 A | 12/1999 | Wolff et al. |
| 6,007,573 A | 12/1999 | Wallace et al. |
| 6,010,514 A | 1/2000 | Burney et al. |
| 6,013,099 A | 1/2000 | Dinh et al. |
| 6,019,786 A | 2/2000 | Thompson |
| 6,030,333 A | 2/2000 | Sioshansi et al. |
| 6,030,613 A | 2/2000 | Blumberg et al. |
| 6,033,434 A | 3/2000 | Borghi |
| 6,035,856 A | 3/2000 | LaFontaine et al. |
| 6,042,875 A | 3/2000 | Ding et al. |
| 6,045,568 A | 4/2000 | Igaki |
| 6,051,017 A | 4/2000 | Loeb et al. |
| 6,056,775 A | 5/2000 | Borghi et al. |
| 6,056,975 A | 5/2000 | Mitra et al. |
| 6,071,305 A | 6/2000 | Brown |
| 6,074,659 A | 6/2000 | Kunz et al. |
| 6,080,177 A | 6/2000 | Igaki |
| 6,080,190 A | 6/2000 | Schwartz |
| 6,086,611 A | 7/2000 | Duffy et al. |
| 6,090,115 A | 7/2000 | Beyar et al. |
| 6,093,200 A | 7/2000 | Liu et al. |
| 6,096,070 A | 8/2000 | Ragheb et al. |
| 6,098,479 A | 8/2000 | Hoermansdoerfer |
| 6,099,561 A | 8/2000 | Alt |
| 6,099,562 A | 8/2000 | Ding et al. |
| 6,106,454 A | 8/2000 | Berg |
| 6,110,188 A | 8/2000 | Narciso |
| 6,113,621 A | 9/2000 | Wiktor |
| 6,113,628 A | 9/2000 | Borghi |
| 6,117,145 A | 9/2000 | Wood et al. |
| 6,117,165 A | 9/2000 | Becker |
| 6,120,535 A | 9/2000 | McDonald et al. |
| 6,120,764 A | 9/2000 | Graham et al. |
| 6,126,675 A | 10/2000 | Shchervinsky |
| 6,132,460 A | 10/2000 | Thompson |
| 6,132,461 A | 10/2000 | Thompson |
| 6,136,010 A | 10/2000 | Modesitt |
| 6,149,680 A | 11/2000 | Shelso et al. |
| 6,152,141 A | 11/2000 | Stevens et al. |
| 6,152,943 A | 11/2000 | Sawhney |
| 6,153,252 A | 11/2000 | Hossainy et al. |
| 6,153,292 A | 11/2000 | Bell et al. |
| 6,156,062 A | 12/2000 | McGuinness |
| 6,156,064 A | 12/2000 | Chouinard |
| 6,159,142 A | 12/2000 | Alt |
| 6,159,531 A | 12/2000 | Dang et al. |
| 6,159,978 A | 12/2000 | Myers et al. |
| 6,165,185 A | 12/2000 | Shennib et al. |
| 6,168,602 B1 | 1/2001 | Ryan |
| 6,171,609 B1 | 1/2001 | Kunz |
| 6,174,330 B1 | 1/2001 | Stinson |
| 6,175,764 B1 | 1/2001 | Loeb et al. |
| 6,176,871 B1 | 1/2001 | Pathak et al. |
| 6,179,867 B1 | 1/2001 | Cox |
| 6,180,632 B1 | 1/2001 | Myers |
| 6,181,965 B1 | 1/2001 | Loeb et al. |
| 6,185,455 B1 | 2/2001 | Loeb et al. |
| 6,187,342 B1 | 2/2001 | Zeidler et al. |
| 6,187,370 B1 | 2/2001 | Dinh et al. |
| 6,190,591 B1 | 2/2001 | Van Lengerich et al. |
| 6,190,696 B1 | 2/2001 | Groenewoud |
| 6,191,119 B1 | 2/2001 | Rubinfeld |
| 6,193,746 B1 | 2/2001 | Strecker |
| 6,197,042 B1 | 3/2001 | Ginn et al. |
| 6,197,586 B1 | 3/2001 | Bhatnager et al. |
| 6,197,789 B1 | 3/2001 | Grainger et al. |
| 6,200,958 B1 | 3/2001 | Odaka et al. |
| 6,203,536 B1 | 3/2001 | Berg et al. |
| 6,203,551 B1 | 3/2001 | Wu |
| 6,206,893 B1 | 3/2001 | Klein et al. |
| 6,206,914 B1 | 3/2001 | Soykan et al. |
| 6,206,915 B1 | 3/2001 | Fagan et al. |
| 6,214,032 B1 | 4/2001 | Loeb et al. |
| 6,214,037 B1 | 4/2001 | Mitchell |
| 6,214,163 B1 | 4/2001 | Matsuda et al. |
| 6,217,609 B1 | 4/2001 | Haverkost |
| 6,221,099 B1 | 4/2001 | Andersen et al. |
| 6,221,383 B1 | 4/2001 | Miranda et al. |
| 6,221,402 B1 | 4/2001 | Itoh et al. |
| 6,224,626 B1 | 5/2001 | Steinke |

(56) References Cited

U.S. PATENT DOCUMENTS

| | | |
|---|---|---|
| 6,224,894 B1 | 5/2001 | Jamiolkowski et al. |
| 6,228,845 B1 | 5/2001 | Donovan et al. |
| 6,231,600 B1 | 5/2001 | Zhong |
| 6,240,616 B1 | 6/2001 | Yan |
| 6,245,103 B1 | 6/2001 | Stinson |
| 6,245,350 B1 | 6/2001 | Amey et al. |
| 6,245,760 B1 | 6/2001 | He et al. |
| 6,245,897 B1 | 6/2001 | Adachi et al. |
| 6,248,117 B1 | 6/2001 | Blatter |
| 6,248,357 B1 | 6/2001 | Ohno et al. |
| 6,251,116 B1 | 6/2001 | Shennib et al. |
| 6,251,135 B1 | 6/2001 | Stinson et al. |
| 6,251,920 B1 | 6/2001 | Grainger et al. |
| 6,254,628 B1 | 7/2001 | Wallace et al. |
| 6,254,631 B1 | 7/2001 | Thompson |
| 6,254,632 B1 | 7/2001 | Wu et al. |
| 6,258,121 B1 | 7/2001 | Yang et al. |
| 6,258,939 B1 | 7/2001 | Reiter et al. |
| 6,261,316 B1 | 7/2001 | Shaolian et al. |
| 6,261,320 B1 | 7/2001 | Tam et al. |
| 6,261,537 B1 | 7/2001 | Klaveness |
| 6,262,079 B1 | 7/2001 | Grainger et al. |
| 6,264,700 B1 | 7/2001 | Kilcoyne et al. |
| 6,268,348 B1 | 7/2001 | Bhatnagar |
| 6,270,515 B1 | 8/2001 | Linden et al. |
| 6,273,910 B1 | 8/2001 | Limon |
| 6,273,911 B1 | 8/2001 | Cox et al. |
| 6,273,913 B1 | 8/2001 | Wright et al. |
| 6,277,140 B2 | 8/2001 | Ginn et al. |
| 6,277,393 B1 | 8/2001 | Yrjanheikki et al. |
| 6,281,015 B1 | 8/2001 | Mooney et al. |
| 6,281,262 B1 | 8/2001 | Shikinami |
| 6,284,271 B1 | 9/2001 | Lundberg et al. |
| 6,284,305 B1 | 9/2001 | Ding et al. |
| 6,284,803 B1 | 9/2001 | Kothrade et al. |
| 6,287,332 B1 | 9/2001 | Bolz |
| 6,287,336 B1 | 9/2001 | Globerman |
| 6,287,628 B1 | 9/2001 | Hossainy et al. |
| 6,290,722 B1 | 9/2001 | Wang |
| 6,290,728 B1 | 9/2001 | Phelps et al. |
| 6,290,990 B1 | 9/2001 | Grabowski et al. |
| 6,299,604 B1 | 10/2001 | Ragheb et al. |
| 6,299,904 B1 | 10/2001 | Shimizu et al. |
| 6,306,166 B1 | 10/2001 | Barry et al. |
| 6,306,421 B1 | 10/2001 | Kunz et al. |
| 6,309,380 B1 | 10/2001 | Larson et al. |
| 6,312,457 B1 | 11/2001 | Dimatteo et al. |
| 6,312,459 B1 | 11/2001 | Huang et al. |
| 6,312,474 B1 | 11/2001 | Francis |
| 6,315,788 B1 | 11/2001 | Roby |
| 6,316,018 B1 | 11/2001 | Ding et al. |
| 6,322,588 B1 | 11/2001 | Ogle |
| 6,328,979 B1 | 12/2001 | Yamashita et al. |
| 6,328,994 B1 | 12/2001 | Shimizu et al. |
| 6,331,163 B1 | 12/2001 | Kaplan |
| 6,331,189 B1 | 12/2001 | Wolinsky |
| 6,331,316 B1 | 12/2001 | Ullah et al. |
| 6,335,029 B1 | 1/2002 | Kamath et al. |
| 6,338,739 B1 | 1/2002 | Datta et al. |
| 6,340,367 B1 | 1/2002 | Stinson et al. |
| 6,340,471 B1 | 1/2002 | Kershman et al. |
| 6,342,068 B1 | 1/2002 | Thompson |
| 6,342,344 B1 | 1/2002 | Thomas et al. |
| 6,344,028 B1 | 2/2002 | Barry |
| 6,346,110 B2 | 2/2002 | Wu |
| 6,348,065 B1 | 2/2002 | Brown |
| 6,350,277 B1 | 2/2002 | Kocur |
| 6,350,398 B1 | 2/2002 | Breitenbach et al. |
| 6,358,274 B1 | 3/2002 | Thompson |
| 6,358,989 B1 | 3/2002 | Kunz et al. |
| 6,364,893 B1 | 4/2002 | Sahatjian et al. |
| 6,365,712 B1 | 4/2002 | Kelly |
| 6,368,341 B1 | 4/2002 | Abrahamson |
| 6,371,953 B1 | 4/2002 | Beyar et al. |
| 6,371,979 B1 | 4/2002 | Beyar et al. |
| 6,371,980 B1 | 4/2002 | Rudakov et al. |
| 6,372,255 B1 | 4/2002 | Saslawski |
| 6,379,373 B1 | 4/2002 | Sawhney et al. |
| 6,379,381 B1 | 4/2002 | Hossain et al. |
| 6,383,471 B1 | 5/2002 | Chen et al. |
| 6,384,046 B1 | 5/2002 | Schuler et al. |
| 6,387,121 B1 | 5/2002 | Alt |
| 6,387,124 B1 | 5/2002 | Buscemi |
| 6,387,663 B1 | 5/2002 | Hall et al. |
| 6,390,098 B1 | 5/2002 | LaFontaine et al. |
| 6,391,033 B2 | 5/2002 | Ryan |
| 6,391,048 B1 | 5/2002 | Ginn et al. |
| 6,391,052 B2 | 5/2002 | Buirge et al. |
| 6,395,300 B1 | 5/2002 | Straub et al. |
| 6,395,326 B1 | 5/2002 | Castro et al. |
| 6,398,816 B1 | 6/2002 | Breitbart et al. |
| 6,399,101 B1 | 6/2002 | Frontanes et al. |
| 6,399,144 B2 | 6/2002 | Dinh et al. |
| 6,403,675 B1 | 6/2002 | Dang et al. |
| 6,403,758 B1 | 6/2002 | Loomis |
| 6,409,716 B1 | 6/2002 | Sahatjian et al. |
| 6,409,750 B1 | 6/2002 | Hyodoh et al. |
| 6,410,587 B1 | 6/2002 | Grainger et al. |
| 6,413,735 B1 | 7/2002 | Lau |
| 6,413,943 B1 | 7/2002 | McArthur et al. |
| 6,416,549 B1 | 7/2002 | Chinn et al. |
| 6,419,692 B1 | 7/2002 | Yang et al. |
| 6,420,378 B1 | 7/2002 | Rubinfeld |
| 6,423,092 B2 | 7/2002 | Datta et al. |
| 6,423,256 B1 | 7/2002 | Kothrade et al. |
| 6,426,145 B1 | 7/2002 | Moroni |
| 6,432,126 B1 | 8/2002 | Gambale et al. |
| 6,432,128 B1 | 8/2002 | Wallace |
| 6,440,164 B1 | 8/2002 | DiMatteo et al. |
| 6,440,734 B1 | 8/2002 | Pykett et al. |
| 6,443,496 B2 | 9/2002 | Campau |
| 6,443,498 B1 | 9/2002 | Liao |
| 6,443,941 B1 | 9/2002 | Slepian et al. |
| 6,447,443 B1 | 9/2002 | Keogh et al. |
| 6,450,989 B2 | 9/2002 | Dubrul et al. |
| 6,451,373 B1 | 9/2002 | Hossainy et al. |
| 6,455,678 B1 | 9/2002 | Yin et al. |
| 6,458,140 B2 | 10/2002 | Akin et al. |
| 6,458,842 B1 | 10/2002 | Dickinson et al. |
| 6,461,364 B1 | 10/2002 | Ginn et al. |
| 6,461,631 B1 | 10/2002 | Dunn |
| 6,464,709 B1 | 10/2002 | Shennib et al. |
| 6,464,889 B1 | 10/2002 | Lee et al. |
| 6,468,302 B2 | 10/2002 | Cox et al. |
| 6,471,980 B2 | 10/2002 | Sirhan et al. |
| 6,478,776 B1 | 11/2002 | Rosenman et al. |
| 6,482,406 B1 | 11/2002 | Stewart |
| 6,482,834 B2 | 11/2002 | Spada et al. |
| 6,485,514 B1 | 11/2002 | Wrenn |
| 6,485,726 B1 | 11/2002 | Blumberg |
| 6,488,702 B1 | 12/2002 | Besselink |
| 6,488,703 B1 | 12/2002 | Kveen |
| 6,488,961 B1 | 12/2002 | Robinson et al. |
| 6,491,666 B1 | 12/2002 | Santini |
| 6,491,938 B2 | 12/2002 | Kunz et al. |
| 6,491,946 B1 | 12/2002 | Schreder et al. |
| 6,494,861 B1 | 12/2002 | Tsukernik |
| 6,494,908 B1 | 12/2002 | Huxel |
| 6,499,984 B1 | 12/2002 | Ghebre-Sellassie et al. |
| 6,500,203 B1 | 12/2002 | Thompson et al. |
| 6,500,204 B1 | 12/2002 | Igaki |
| 6,500,421 B1 | 12/2002 | Sorrentino et al. |
| 6,503,273 B1 | 1/2003 | McAllister |
| 6,503,278 B1 | 1/2003 | Pohjonen |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,511,505 B2 | 1/2003 | Cox et al. |
| 6,511,748 B1 | 1/2003 | Barrows |
| 6,514,283 B2 | 2/2003 | DiMatteo et al. |
| 6,514,515 B1 | 2/2003 | Williams |
| 6,515,009 B1 | 2/2003 | Kunz et al. |
| 6,517,553 B2 | 2/2003 | Klein et al. |

(56) References Cited

U.S. PATENT DOCUMENTS

| | | |
|---|---|---|
| 6,517,889 B1 | 2/2003 | Jayaraman |
| 6,524,345 B1 | 2/2003 | Vlimaa et al. |
| 6,524,347 B1 | 2/2003 | Myers et al. |
| 6,526,320 B2 | 2/2003 | Mitchell |
| 6,527,801 B1 | 3/2003 | Dutta |
| 6,528,080 B2 | 3/2003 | Dunn |
| 6,528,107 B2 | 3/2003 | Chinn et al. |
| 6,528,526 B1 | 3/2003 | Myers et al. |
| 6,530,951 B1 | 3/2003 | Bates et al. |
| 6,531,147 B2 | 3/2003 | Sawhney et al. |
| 6,537,256 B2 | 3/2003 | Santini et al. |
| 6,537,312 B2 | 3/2003 | Datta |
| 6,540,735 B1 | 4/2003 | Ashby et al. |
| 6,540,774 B1 | 4/2003 | Cox |
| 6,540,776 B2 | 4/2003 | Millare et al. |
| 6,541,116 B2 | 4/2003 | Michal et al. |
| 6,544,185 B2 | 4/2003 | Montegrande |
| 6,544,582 B1 | 4/2003 | Yoe |
| 6,545,097 B2 | 4/2003 | Pinchuk et al. |
| 6,548,025 B1 | 4/2003 | Rasouli et al. |
| 6,548,569 B1 | 4/2003 | Williams et al. |
| 6,551,350 B1 | 4/2003 | Thornton |
| 6,551,352 B2 | 4/2003 | Clerc et al. |
| 6,554,855 B1 | 4/2003 | Dong |
| 6,555,157 B1 | 4/2003 | Hossainy |
| 6,559,176 B1 | 5/2003 | Bassler et al. |
| 6,562,065 B1 | 5/2003 | Shanley |
| 6,565,598 B1 | 5/2003 | Lootz |
| 6,565,599 B1 | 5/2003 | Hong |
| 6,565,600 B2 | 5/2003 | Hojeibane |
| 6,565,601 B2 | 5/2003 | Wallace et al. |
| 6,569,190 B2 | 5/2003 | Whalen et al. |
| 6,569,191 B1 | 5/2003 | Hogan |
| 6,569,441 B2 | 5/2003 | Kunz et al. |
| 6,574,851 B1 | 6/2003 | Mirizzi |
| 6,575,888 B2 | 6/2003 | Zamora et al. |
| 6,579,309 B1 | 6/2003 | Loos |
| 6,583,276 B1 | 6/2003 | Neufeld et al. |
| 6,585,755 B2 | 7/2003 | Jackson |
| 6,585,758 B1 | 7/2003 | Chouinard |
| 6,585,765 B1 | 7/2003 | Hossainy et al. |
| 6,585,773 B1 | 7/2003 | Xie |
| 6,589,546 B2 | 7/2003 | Kamath et al. |
| 6,592,617 B2 | 7/2003 | Thompson |
| 6,596,021 B1 | 7/2003 | Lootz |
| 6,596,022 B2 | 7/2003 | Lau |
| 6,596,296 B1 | 7/2003 | Nelson |
| 6,596,699 B2 | 7/2003 | Zamora et al. |
| 6,599,274 B1 | 7/2003 | Kucharczyk et al. |
| 6,599,928 B2 | 7/2003 | Kunz et al. |
| 6,602,283 B2 | 8/2003 | Doran |
| 6,602,284 B2 | 8/2003 | Cox |
| 6,605,110 B2 | 8/2003 | Harrison |
| 6,605,294 B2 | 8/2003 | Sawhney |
| 6,607,548 B2 | 8/2003 | Pohjonen et al. |
| 6,607,554 B2 | 8/2003 | Dang |
| 6,607,720 B1 | 8/2003 | Xiao et al. |
| 6,607,724 B2 | 8/2003 | O'Reilly et al. |
| 6,610,100 B2 | 8/2003 | Phelps et al. |
| 6,613,070 B2 | 9/2003 | Redmond |
| 6,613,077 B2 | 9/2003 | Gilligan |
| 6,613,079 B1 | 9/2003 | Wolinsky |
| 6,613,080 B1 | 9/2003 | Lootz |
| 6,613,081 B2 | 9/2003 | Kim |
| 6,613,082 B2 | 9/2003 | Yang |
| 6,613,083 B2 | 9/2003 | Alt |
| 6,613,084 B2 | 9/2003 | Yang |
| 6,616,591 B1 | 9/2003 | Teoh et al. |
| 6,616,617 B1 | 9/2003 | Terrera et al. |
| 6,616,689 B1 | 9/2003 | Ainsworth |
| 6,616,765 B1 | 9/2003 | Castro |
| 6,620,122 B2 | 9/2003 | Stinson et al. |
| 6,620,170 B1 | 9/2003 | Ahern |
| 6,620,194 B2 | 9/2003 | Ding et al. |
| 6,620,617 B2 | 9/2003 | Mathiowitz |
| 6,623,494 B1 | 9/2003 | Blatter |
| 6,623,521 B2 | 9/2003 | Steinke |
| 6,626,918 B1 | 9/2003 | Ginn et al. |
| 6,626,936 B2 | 9/2003 | Stinson |
| 6,626,939 B1 | 9/2003 | Burnside |
| 6,627,209 B2 | 9/2003 | Easterling |
| 6,627,246 B2 | 9/2003 | Mehta et al. |
| 6,629,988 B2 | 10/2003 | Weadock |
| 6,629,992 B2 | 10/2003 | Bigus et al. |
| 6,629,993 B2 | 10/2003 | Voinov |
| 6,629,995 B1 | 10/2003 | Wrenn et al. |
| 6,635,068 B1 | 10/2003 | Dubrul et al. |
| 6,641,611 B2 | 11/2003 | Jayaraman |
| 6,645,241 B1 | 11/2003 | Strecker |
| 6,652,575 B2 | 11/2003 | Wang |
| 6,652,582 B1 | 11/2003 | Stinson |
| 6,653,426 B2 | 11/2003 | Alvarado |
| 6,656,136 B1 | 12/2003 | Weng et al. |
| 6,656,156 B2 | 12/2003 | Yang et al. |
| 6,656,162 B2 | 12/2003 | Santini, Jr. et al. |
| 6,660,034 B1 | 12/2003 | Mandrusov et al. |
| 6,663,662 B2 | 12/2003 | Pacetti et al. |
| 6,663,665 B2 | 12/2003 | Shaolian et al. |
| 6,663,880 B1 | 12/2003 | Roorda et al. |
| 6,663,881 B2 | 12/2003 | Kunz et al. |
| 6,664,233 B1 | 12/2003 | Rubinfeld |
| 6,667,051 B1 | 12/2003 | Gregory |
| 6,669,719 B2 | 12/2003 | Wallace et al. |
| 6,670,398 B2 | 12/2003 | Edwards et al. |
| 6,673,341 B2 | 1/2004 | Sukhatme |
| 6,673,385 B1 | 1/2004 | Ding et al. |
| 6,676,694 B1 | 1/2004 | Weiss |
| 6,676,937 B1 * | 1/2004 | Isner et al. .................. 424/93.7 |
| 6,682,473 B1 | 1/2004 | Matsuura et al. |
| 6,682,545 B1 | 1/2004 | Kester |
| 6,682,555 B2 | 1/2004 | Cioanta et al. |
| 6,685,734 B1 | 2/2004 | Valimaa et al. |
| 6,685,739 B2 | 2/2004 | Dimatteo et al. |
| 6,685,745 B2 | 2/2004 | Reever |
| 6,689,148 B2 | 2/2004 | Sawhney et al. |
| 6,689,162 B1 | 2/2004 | Thompson |
| 6,692,520 B1 | 2/2004 | Gambale et al. |
| 6,695,867 B2 | 2/2004 | Ginn et al. |
| 6,695,879 B2 | 2/2004 | Bell |
| 6,696,434 B2 | 2/2004 | Myers et al. |
| 6,699,272 B2 | 3/2004 | Slepian et al. |
| 6,702,850 B1 | 3/2004 | Byun |
| 6,709,452 B1 | 3/2004 | Valimaa |
| 6,709,455 B1 | 3/2004 | Chouinard |
| 6,709,465 B2 | 3/2004 | Mitchell |
| 6,709,514 B1 | 3/2004 | Hossainy |
| 6,712,845 B2 | 3/2004 | Hossainy |
| 6,712,852 B1 | 3/2004 | Chung et al. |
| 6,713,119 B2 | 3/2004 | Hossainy et al. |
| 6,719,784 B2 | 4/2004 | Henderson |
| 6,719,934 B2 | 4/2004 | Stinson |
| 6,720,350 B2 | 4/2004 | Kunz et al. |
| 6,723,120 B2 | 4/2004 | Yan |
| 6,726,696 B1 | 4/2004 | Houser et al. |
| 6,726,923 B2 | 4/2004 | Iyer et al. |
| 6,730,064 B2 | 5/2004 | Ragheb et al. |
| 6,730,120 B2 | 5/2004 | Berg et al. |
| 6,733,768 B2 | 5/2004 | Hossainy et al. |
| 6,736,828 B1 | 5/2004 | Adams et al. |
| 6,737,053 B1 | 5/2004 | Goh et al. |
| 6,740,100 B2 | 5/2004 | Demopulos et al. |
| 6,740,101 B2 | 5/2004 | Houser et al. |
| 6,740,121 B2 | 5/2004 | Geitz |
| 6,743,462 B1 | 6/2004 | Pacetti |
| 6,746,685 B2 | 6/2004 | Williams |
| 6,746,755 B2 | 6/2004 | Morrison et al. |
| 6,746,773 B2 | 6/2004 | Llanos et al. |
| 6,749,621 B2 | 6/2004 | Pantages |
| 6,752,826 B2 | 6/2004 | Holloway |
| 6,752,829 B2 | 6/2004 | Kocur et al. |
| 6,753,071 B1 | 6/2004 | Pacetti |
| 6,755,869 B2 | 6/2004 | Geitz |
| 6,758,857 B2 | 7/2004 | Cioanta et al. |
| 6,759,054 B2 | 7/2004 | Chen et al. |

(56) References Cited

U.S. PATENT DOCUMENTS

| | | |
|---|---|---|
| 6,770,070 B1 | 8/2004 | Balbierz |
| 6,773,455 B2 | 8/2004 | Allen et al. |
| 6,774,278 B1 | 8/2004 | Ragheb et al. |
| 6,780,890 B2 | 8/2004 | Bassler et al. |
| 6,783,793 B1 | 8/2004 | Hossainy et al. |
| 6,786,929 B2 | 9/2004 | Gambale et al. |
| 6,790,185 B1 | 9/2004 | Fisher et al. |
| 6,790,220 B2 | 9/2004 | Morris et al. |
| 6,790,228 B2 | 9/2004 | Hossainy et al. |
| 6,790,606 B1 | 9/2004 | Lau |
| 6,792,979 B2 | 9/2004 | Konya et al. |
| 6,794,363 B2 | 9/2004 | Bejanin et al. |
| 6,796,960 B2 | 9/2004 | Cioanta et al. |
| 6,800,089 B1 | 10/2004 | Wang |
| 6,805,706 B2 | 10/2004 | Solovay et al. |
| 6,805,876 B2 | 10/2004 | Leong |
| 6,805,898 B1 | 10/2004 | Wu et al. |
| RE38,653 E | 11/2004 | Igaki |
| 6,812,217 B2 | 11/2004 | Hendricks |
| 6,818,016 B1 | 11/2004 | Nabel et al. |
| 6,818,247 B1 | 11/2004 | Chen et al. |
| 6,821,296 B2 | 11/2004 | Brauckman et al. |
| 6,821,549 B2 | 11/2004 | Jayaraman |
| 6,821,962 B2 | 11/2004 | Myers et al. |
| 6,824,561 B2 * | 11/2004 | Soykan et al. ............ 623/1.42 |
| 6,827,737 B2 | 12/2004 | Hill et al. |
| 6,830,575 B2 | 12/2004 | Stenzel et al. |
| 6,838,493 B2 | 1/2005 | Williams |
| 6,840,957 B2 | 1/2005 | DiMatteo et al. |
| 6,842,795 B2 | 1/2005 | Keller |
| 6,843,795 B1 | 1/2005 | Houser et al. |
| 6,844,024 B2 | 1/2005 | Su et al. |
| 6,846,323 B2 | 1/2005 | Yip et al. |
| 6,846,815 B2 | 1/2005 | Myers et al. |
| 6,852,122 B2 | 2/2005 | Rush |
| 6,852,124 B2 | 2/2005 | Cox |
| 6,852,533 B1 * | 2/2005 | Rafii et al. ............... 435/372 |
| 6,852,712 B2 | 2/2005 | Myers et al. |
| RE38,711 E | 3/2005 | Igaki |
| 6,860,898 B2 | 3/2005 | Stack |
| 6,860,946 B2 | 3/2005 | Hossainy et al. |
| 6,863,684 B2 | 3/2005 | Kim |
| 6,863,899 B2 | 3/2005 | Koblish et al. |
| 6,864,346 B2 | 3/2005 | Schoenheider |
| 6,866,805 B2 | 3/2005 | Hong |
| 6,867,247 B2 | 3/2005 | Williams et al. |
| 6,869,443 B2 | 3/2005 | Buscemi |
| 6,878,161 B2 | 4/2005 | Lenker |
| 6,881,222 B2 | 4/2005 | White |
| 6,884,429 B2 | 4/2005 | Koziak et al. |
| 6,887,249 B1 | 5/2005 | Houser et al. |
| 6,890,339 B2 | 5/2005 | Sahatjiam et al. |
| 6,890,350 B1 | 5/2005 | Walak |
| 6,893,431 B2 | 5/2005 | Naimark et al. |
| 6,893,458 B2 | 5/2005 | Cox |
| 6,893,657 B2 | 5/2005 | Roser et al. |
| 6,895,282 B2 | 5/2005 | Gellman et al. |
| 6,896,695 B2 | 5/2005 | Mueller |
| 6,896,696 B2 | 5/2005 | Doran et al. |
| 6,896,697 B1 | 5/2005 | Yip et al. |
| 6,896,965 B1 | 5/2005 | Hossainy |
| 6,897,245 B2 | 5/2005 | Gen |
| 6,899,729 B1 | 5/2005 | Cox et al. |
| 6,899,889 B1 | 5/2005 | Hnojewyj |
| 6,902,575 B2 | 6/2005 | Laakso et al. |
| 6,905,455 B2 | 6/2005 | Rapach et al. |
| 6,908,624 B2 | 6/2005 | Hossainy et al. |
| 6,911,003 B2 | 6/2005 | Anderson et al. |
| 6,913,617 B1 | 7/2005 | Reiss |
| 6,913,626 B2 | 7/2005 | McGhan |
| 6,916,483 B2 | 7/2005 | Ralph et al. |
| 6,918,869 B2 | 7/2005 | Shaw et al. |
| 6,921,390 B2 | 7/2005 | Bucay-Couto et al. |
| 6,921,811 B2 | 7/2005 | Zamora et al. |
| 6,926,690 B2 | 8/2005 | Renati |
| 6,926,733 B2 | 8/2005 | Stinson |
| 6,926,919 B1 | 8/2005 | Hossainy et al. |
| 6,936,706 B2 | 8/2005 | do Couto et al. |
| 6,939,381 B2 | 9/2005 | Stark et al. |
| 6,939,568 B2 | 9/2005 | Burrell et al. |
| 6,942,674 B2 | 9/2005 | Belef et al. |
| 6,945,949 B2 | 9/2005 | Wilk |
| 6,946,002 B2 | 9/2005 | Geitz |
| 6,946,145 B2 | 9/2005 | Ng et al. |
| 6,949,080 B2 | 9/2005 | Wolf et al. |
| 6,949,116 B2 | 9/2005 | Solymar et al. |
| 6,951,053 B2 | 10/2005 | Padilla |
| 6,953,481 B2 | 10/2005 | Phelps et al. |
| 6,953,482 B2 | 10/2005 | Doi et al. |
| 6,958,147 B1 | 10/2005 | Alitalo et al. |
| 6,964,658 B2 | 11/2005 | Ashby et al. |
| 6,964,668 B2 | 11/2005 | Modesitt et al. |
| 6,971,998 B2 | 12/2005 | Rosenman et al. |
| 6,976,950 B2 | 12/2005 | Connors et al. |
| 6,976,951 B2 | 12/2005 | Connors et al. |
| 6,979,071 B2 | 12/2005 | Suzuki et al. |
| 6,979,347 B1 | 12/2005 | Wu et al. |
| 6,979,473 B2 | 12/2005 | O'Connor et al. |
| 6,981,944 B2 | 1/2006 | Jamiolkowski et al. |
| 6,981,987 B2 | 1/2006 | Huxel et al. |
| 6,984,247 B2 | 1/2006 | Cauthen |
| 6,986,899 B2 | 1/2006 | Hossainy et al. |
| 6,988,983 B2 | 1/2006 | Connors |
| 6,989,030 B1 | 1/2006 | Ohgushi |
| 6,989,034 B2 | 1/2006 | Hammer et al. |
| 6,989,071 B2 | 1/2006 | Kocur |
| 6,989,262 B2 | 1/2006 | Bejanin |
| 6,991,643 B2 | 1/2006 | Saadat |
| 6,991,646 B2 | 1/2006 | Clerc et al. |
| 6,991,647 B2 | 1/2006 | Jadhav |
| 6,991,681 B2 | 1/2006 | Yoe |
| 6,994,867 B1 | 2/2006 | Hossainy et al. |
| 6,997,948 B2 | 2/2006 | Stinson |
| 6,997,949 B2 | 2/2006 | Tuch |
| 6,997,953 B2 | 2/2006 | Chung et al. |
| 6,997,956 B2 | 2/2006 | Cauthen |
| 6,997,989 B2 | 2/2006 | Spencer et al. |
| 7,001,328 B1 | 2/2006 | Barofsky et al. |
| 7,001,400 B1 | 2/2006 | Modesitt et al. |
| 7,001,410 B2 | 2/2006 | Fisher |
| 7,001,421 B2 | 2/2006 | Cheng |
| 7,001,881 B1 | 2/2006 | Jay |
| 7,004,962 B2 | 2/2006 | Stinson |
| 7,004,970 B2 | 2/2006 | Cauthen et al. |
| 7,004,976 B2 | 2/2006 | Ornberg |
| 7,005,137 B1 | 2/2006 | Hossainy et al. |
| 7,005,500 B2 | 2/2006 | Bejanin et al. |
| 7,008,396 B1 | 3/2006 | Straub |
| 7,008,642 B1 | 3/2006 | Roorda et al. |
| 7,009,034 B2 | 3/2006 | Pathak et al. |
| 7,011,654 B2 | 3/2006 | Dubrul et al. |
| 7,011,677 B2 | 3/2006 | Wallace et al. |
| 7,011,842 B1 | 3/2006 | Simhambhatla et al. |
| 7,012,106 B2 | 3/2006 | Yuan et al. |
| 7,014,861 B2 | 3/2006 | Roorda et al. |
| 7,014,913 B2 | 3/2006 | Pacetti |
| 7,018,401 B1 | 3/2006 | Hyodoh et al. |
| 7,022,132 B2 | 4/2006 | Kocur |
| 7,022,334 B1 | 4/2006 | Ding |
| 7,022,343 B2 | 4/2006 | Philbrook et al. |
| 7,022,372 B1 | 4/2006 | Chen |
| 7,022,522 B2 | 4/2006 | Guan et al. |
| 7,025,776 B1 | 4/2006 | Houser et al. |
| 7,026,374 B2 | 4/2006 | Nathan et al. |
| 7,029,480 B2 | 4/2006 | Klein et al. |
| 7,030,127 B2 | 4/2006 | Nathan et al. |
| 7,031,775 B2 | 4/2006 | Soykan et al. |
| 7,033,395 B2 | 4/2006 | Cauthen |
| 7,033,602 B1 | 4/2006 | Pacetti et al. |
| 7,033,603 B2 | 4/2006 | Nelson |
| 7,034,037 B2 | 4/2006 | Arnold et al. |
| 7,037,332 B2 | 5/2006 | Kutryk et al. |
| 7,037,342 B2 | 5/2006 | Nilsson et al. |
| 7,037,344 B2 | 5/2006 | Kagan et al. |

(56) References Cited

U.S. PATENT DOCUMENTS

| | | |
|---|---|---|
| 7,041,130 B2 | 5/2006 | Santini et al. |
| 7,044,962 B2 | 5/2006 | Elliott |
| 7,048,014 B2 | 5/2006 | Hyodoh et al. |
| 7,048,939 B2 | 5/2006 | Elkins et al. |
| 7,049,373 B2 | 5/2006 | Matyjaszewski et al. |
| 7,052,488 B2 | 5/2006 | Uhland |
| 7,052,513 B2 | 5/2006 | Thompson |
| 7,052,516 B2 | 5/2006 | Cauthen et al. |
| 7,056,337 B2 | 6/2006 | Boatman |
| 7,056,412 B2 | 6/2006 | Henderson |
| 7,056,493 B2 | 6/2006 | Kohn |
| 7,056,495 B2 | 6/2006 | Roser et al. |
| 7,056,523 B1 | 6/2006 | Claude et al. |
| 7,056,550 B2 | 6/2006 | Davila et al. |
| 7,056,591 B1 | 6/2006 | Pacetti |
| 7,060,056 B2 | 6/2006 | Palasis et al. |
| 7,060,087 B2 | 6/2006 | Dimatteo et al. |
| 7,060,319 B2 | 6/2006 | Fredrickson |
| 7,063,884 B2 | 6/2006 | Hossainy |
| 7,066,952 B2 | 6/2006 | Igaki |
| 7,070,556 B2 | 7/2006 | Anderson et al. |
| 7,070,616 B2 | 7/2006 | Majercak et al. |
| 7,070,798 B1 | 7/2006 | Michal et al. |
| 7,074,178 B2 | 7/2006 | Connors et al. |
| 7,074,189 B1 | 7/2006 | Montegrande |
| 7,074,229 B2 | 7/2006 | Adams et al. |
| 7,074,412 B2 | 7/2006 | Weber |
| 7,074,571 B2 | 7/2006 | Bejanin et al. |
| 7,074,803 B2 | 7/2006 | Litmanovitz et al. |
| 7,074,901 B2 | 7/2006 | Bejanin et al. |
| 7,077,860 B2 | 7/2006 | Yan et al. |
| 7,078,032 B2 | 7/2006 | MacLaughlin et al. |
| 7,083,629 B2 | 8/2006 | Weller et al. |
| 7,083,641 B2 | 8/2006 | Stinson et al. |
| 7,083,643 B2 | 8/2006 | Whalen et al. |
| 7,087,263 B2 | 8/2006 | Hossainy et al. |
| 7,087,645 B2 | 8/2006 | Glass et al. |
| 7,087,661 B1 | 8/2006 | Alberte et al. |
| 7,090,655 B2 | 8/2006 | Barry |
| 7,090,699 B2 | 8/2006 | Geitz |
| 7,090,888 B2 | 8/2006 | Snyder et al. |
| 7,091,297 B2 | 8/2006 | Mather et al. |
| 7,094,256 B1 | 8/2006 | Shah et al. |
| 7,094,369 B2 | 8/2006 | Buiser |
| 7,094,418 B2 | 8/2006 | Chudzik |
| 7,094,876 B2 | 8/2006 | Bejanin et al. |
| 7,097,907 B2 | 8/2006 | Bennett et al. |
| 7,100,616 B2 | 9/2006 | Springmeyer |
| 7,101,402 B2 | 9/2006 | Phelps et al. |
| 7,105,021 B2 | 9/2006 | Edens et al. |
| 7,105,058 B1 | 9/2006 | Sinyagin |
| 7,108,701 B2 | 9/2006 | Evens et al. |
| 7,108,714 B1 | 9/2006 | Becker |
| 7,108,716 B2 | 9/2006 | Burnside et al. |
| 7,112,587 B2 | 9/2006 | Timmer et al. |
| 7,115,300 B1 | 10/2006 | Hossainy |
| 7,118,593 B2 | 10/2006 | Davidson |
| 7,122,629 B2 | 10/2006 | Bejanin et al. |
| 7,128,755 B2 | 10/2006 | Su |
| 7,128,756 B2 | 10/2006 | Lowe et al. |
| 7,128,927 B1 | 10/2006 | Dunn |
| 7,129,210 B2 | 10/2006 | Lowinger et al. |
| 7,129,300 B2 | 10/2006 | Roby |
| 7,129,319 B2 | 10/2006 | Shalaby |
| 7,132,423 B2 | 11/2006 | Timmer et al. |
| 7,132,567 B2 | 11/2006 | Alberte et al. |
| 7,135,038 B1 | 11/2006 | Limon |
| 7,135,039 B2 | 11/2006 | De Scheerder et al. |
| 7,137,993 B2 | 11/2006 | Acosta |
| 7,138,439 B2 | 11/2006 | Scheer et al. |
| 7,144,411 B2 | 12/2006 | Ginn et al. |
| 7,144,422 B1 | 12/2006 | Rao |
| 7,150,853 B2 | 12/2006 | Lee |
| 7,151,135 B2 | 12/2006 | Rhee |
| 7,151,139 B2 | 12/2006 | Tiller et al. |
| 7,153,322 B2 | 12/2006 | Alt |
| 7,153,324 B2 | 12/2006 | Case et al. |
| 7,156,862 B2 | 1/2007 | Jacobs et al. |
| 7,156,880 B2 | 1/2007 | Evans et al. |
| 7,160,317 B2 | 1/2007 | McHale et al. |
| 7,160,319 B2 | 1/2007 | Chouinard |
| 7,160,321 B2 | 1/2007 | Shanley |
| 7,160,726 B2 | 1/2007 | Mansbridge et al. |
| 7,163,555 B2 | 1/2007 | Dinh |
| 7,163,562 B2 | 1/2007 | Datta et al. |
| 7,163,943 B2 | 1/2007 | Timmer et al. |
| 7,166,134 B2 | 1/2007 | Datta |
| 7,166,570 B2 | 1/2007 | Hunter et al. |
| 7,166,574 B2 | 1/2007 | Pena et al. |
| 7,166,680 B2 | 1/2007 | DesNoyer |
| 7,169,173 B2 | 1/2007 | Hossainy et al. |
| 7,169,187 B2 | 1/2007 | Datta |
| 7,169,404 B2 | 1/2007 | Hossainy et al. |
| 7,169,784 B2 | 1/2007 | Timmer et al. |
| 7,169,785 B2 | 1/2007 | Timmer et al. |
| 7,173,032 B2 | 2/2007 | Timmer et al. |
| 7,173,096 B2 | 2/2007 | Mather et al. |
| 7,175,644 B2 | 2/2007 | Cooper et al. |
| 7,175,658 B1 | 2/2007 | Flugelman |
| 7,175,669 B2 | 2/2007 | Geitz |
| 7,175,873 B1 | 2/2007 | Roord et al. |
| 7,175,874 B1 | 2/2007 | Pacetti |
| 7,179,883 B2 | 2/2007 | Williams |
| 7,182,771 B1 | 2/2007 | Houser et al. |
| 7,186,789 B2 | 3/2007 | Hossainy et al. |
| 7,189,235 B2 | 3/2007 | Cauthen |
| 7,189,263 B2 | 3/2007 | Erbe et al. |
| 7,189,789 B2 | 3/2007 | Koike et al. |
| 7,195,640 B2 | 3/2007 | Falotico et al. |
| 7,195,646 B2 | 3/2007 | Nahleili |
| 7,198,675 B2 | 4/2007 | Fox et al. |
| 7,202,325 B2 | 4/2007 | Pacetti et al. |
| 7,208,002 B2 | 4/2007 | Shelso |
| 7,208,190 B2 | 4/2007 | Verlee et al. |
| 7,208,550 B2 | 4/2007 | Mather et al. |
| 7,211,039 B2 | 5/2007 | Lamoureux |
| 7,211,109 B2 | 5/2007 | Thompson |
| 7,212,100 B2 | 5/2007 | Terenna |
| 7,214,229 B2 | 5/2007 | Mitchell et al. |
| 7,214,383 B2 | 5/2007 | Daniels |
| 7,214,759 B2 | 5/2007 | Pacetti et al. |
| 7,215,383 B2 | 5/2007 | Hannah et al. |
| 7,217,426 B1 | 5/2007 | Hossainy et al. |
| 7,220,237 B2 | 5/2007 | Gannoe et al. |
| 7,220,268 B2 | 5/2007 | Blatter |
| 7,220,270 B2 | 5/2007 | Sawhney et al. |
| 7,220,272 B2 | 5/2007 | Weadock |
| 7,220,276 B1 | 5/2007 | Williams et al. |
| 7,220,284 B2 | 5/2007 | Kagan et al. |
| 7,220,816 B2 | 5/2007 | Pacetti et al. |
| 7,226,467 B2 | 6/2007 | Lucatero et al. |
| 7,226,473 B2 | 6/2007 | Brar et al. |
| 7,226,589 B2 * | 6/2007 | Nabel et al. ............... 424/93.21 |
| 7,229,428 B2 | 6/2007 | Gannoe et al. |
| 7,229,454 B2 | 6/2007 | Tran et al. |
| 7,229,471 B2 | 6/2007 | Gale et al. |
| 7,230,521 B2 | 6/2007 | Terenna |
| 7,232,573 B1 | 6/2007 | Ding |
| 7,235,087 B2 | 6/2007 | Modesitt et al. |
| 7,235,096 B1 | 6/2007 | Van Tassel et al. |
| 7,238,363 B2 | 7/2007 | Mansouri et al. |
| 7,238,692 B2 | 7/2007 | Timmer et al. |
| 7,241,310 B2 | 7/2007 | Taylor et al. |
| 7,241,344 B2 | 7/2007 | Worsham et al. |
| 7,241,736 B2 | 7/2007 | Hunter et al. |
| 7,244,441 B2 | 7/2007 | Schreiner |
| 7,244,443 B2 | 7/2007 | Pacetti |
| 7,247,313 B2 | 7/2007 | Roorda et al. |
| 7,247,364 B2 | 7/2007 | Hossainy et al. |
| 7,255,675 B2 | 8/2007 | Gertner et al. |
| 7,255,891 B1 | 8/2007 | Pacetti |
| 7,258,891 B2 | 8/2007 | Pacetti et al. |
| 7,261,915 B2 | 8/2007 | Boulais et al. |
| 7,261,946 B2 | 8/2007 | Claude |

(56) References Cited

U.S. PATENT DOCUMENTS

| | | |
|---|---|---|
| 7,265,114 B2 | 9/2007 | Timmer et al. |
| 7,267,686 B2 | 9/2007 | DiMatteo et al. |
| 7,268,134 B2 | 9/2007 | Timmer et al. |
| 7,268,205 B2 | 9/2007 | William et al. |
| 7,270,668 B2 | 9/2007 | Andreas et al. |
| 7,270,675 B2 | 9/2007 | Chun et al. |
| 7,273,492 B2 | 9/2007 | Cheng et al. |
| 7,273,497 B2 | 9/2007 | Ferree |
| 7,279,005 B2 | 10/2007 | Stinson |
| 7,279,008 B2 | 10/2007 | Brown et al. |
| 7,279,174 B2 | 10/2007 | Pacetti et al. |
| 7,279,175 B2 | 10/2007 | Chen et al. |
| 7,285,304 B1 | 10/2007 | Hossainy et al. |
| 7,288,111 B1 | 10/2007 | Holloway et al. |
| 7,288,609 B1 | 10/2007 | Pacetti |
| 7,291,166 B2 | 11/2007 | Cheng et al. |
| 7,291,169 B2 | 11/2007 | Hodorek |
| 7,291,495 B2 | 11/2007 | Bejanin et al. |
| 7,294,115 B1 | 11/2007 | Wilk |
| 7,294,146 B2 | 11/2007 | Chew et al. |
| 7,294,329 B1 | 11/2007 | Ding |
| 7,294,334 B1 | 11/2007 | Michal et al. |
| 7,297,159 B2 | 11/2007 | Hossainy et al. |
| 7,297,348 B2 | 11/2007 | Li et al. |
| 7,297,758 B2 | 11/2007 | Gale et al. |
| 7,301,001 B2 | 11/2007 | Hossainy et al. |
| 7,303,758 B2 | 12/2007 | Falotico et al. |
| 7,304,122 B2 | 12/2007 | Chu et al. |
| 7,311,727 B2 | 12/2007 | Mazumder et al. |
| 7,311,980 B1 | 12/2007 | Hossainy et al. |
| 7,312,299 B2 | 12/2007 | Hossainy et al. |
| 7,314,636 B2 | 1/2008 | Caseres et al. |
| 7,316,710 B1 | 1/2008 | Cheng et al. |
| 7,320,702 B2 | 1/2008 | Hammersmark et al. |
| 7,323,005 B2 | 1/2008 | Wallace et al. |
| 7,323,190 B2 | 1/2008 | Chu et al. |
| 7,323,210 B2 | 1/2008 | Castro et al. |
| 7,326,571 B2 | 2/2008 | Freyman |
| 7,329,277 B2 | 2/2008 | Addonizio et al. |
| 7,329,366 B1 | 2/2008 | Gale et al. |
| 7,329,413 B1 | 2/2008 | Pacetti et al. |
| 7,329,414 B2 | 2/2008 | Fisher et al. |
| 7,331,199 B2 | 2/2008 | Ory et al. |
| 7,331,980 B2 | 2/2008 | Dubrul et al. |
| 7,332,113 B2 | 2/2008 | Beruto et al. |
| 7,332,488 B2 | 2/2008 | Timmer et al. |
| 7,332,489 B2 | 2/2008 | Timmer et al. |
| 7,332,490 B2 | 2/2008 | Timmer et al. |
| 7,332,566 B2 | 2/2008 | Pathak et al. |
| 7,335,220 B2 | 2/2008 | Khosravi et al. |
| 7,335,264 B2 | 2/2008 | Motherwell et al. |
| 7,335,314 B2 | 2/2008 | Wu et al. |
| 7,335,391 B1 | 2/2008 | Pacetti |
| 7,335,508 B2 | 2/2008 | Yayon et al. |
| 7,335,656 B2 | 2/2008 | Timmer et al. |
| 7,335,770 B2 | 2/2008 | Timmer et al. |
| 7,698,111 B2 | 4/2010 | Abrahao et al. |
| 2001/0000802 A1 | 5/2001 | Soykan et al. |
| 2001/0053362 A1 | 12/2001 | Walters |
| 2002/0032315 A1 | 3/2002 | Baca et al. |
| 2002/0049495 A1 | 4/2002 | Kutryk et al. |
| 2002/0051762 A1 | 5/2002 | Rafii et al. |
| 2002/0053092 A1 | 5/2002 | Readhead et al. |
| 2002/0055770 A1 | 5/2002 | Doran et al. |
| 2002/0056148 A1 | 5/2002 | Readhead et al. |
| 2002/0062145 A1 | 5/2002 | Rudakov et al. |
| 2002/0083479 A1 | 6/2002 | Winston et al. |
| 2002/0086316 A1 | 7/2002 | Billing-Medel et al. |
| 2002/0095206 A1 | 7/2002 | Addonizio et al. |
| 2002/0133835 A1 | 9/2002 | Winston et al. |
| 2002/0138865 A1 | 9/2002 | Readhead et al. |
| 2002/0177176 A1 | 11/2002 | Thomas et al. |
| 2002/0192730 A1 | 12/2002 | Soker et al. |
| 2003/0082148 A1 | 5/2003 | Ludwig et al. |
| 2003/0113331 A1 | 6/2003 | Brooks et al. |
| 2003/0125615 A1 | 7/2003 | Schwartz |
| 2003/0157071 A1 | 8/2003 | Wolfe et al. |
| 2003/0185794 A1 | 10/2003 | Colley |
| 2003/0229393 A1 | 12/2003 | Kutryk et al. |
| 2004/0029268 A1 | 2/2004 | Colb et al. |
| 2004/0039441 A1 | 2/2004 | Rowland et al. |
| 2004/0167572 A1 | 8/2004 | Roth et al. |
| 2005/0025752 A1 | 2/2005 | Kutryk et al. |
| 2005/0043787 A1 | 2/2005 | Kutryk et al. |
| 2005/0070989 A1 | 3/2005 | Lye et al. |
| 2005/0147644 A1 | 7/2005 | Sahota |
| 2005/0149163 A1 | 7/2005 | Sahota |
| 2005/0149174 A1 | 7/2005 | Hezi-Yamit et al. |
| 2005/0187607 A1 | 8/2005 | Akhtar et al. |
| 2005/0271701 A1 | 12/2005 | Cottone et al. |
| 2006/0009840 A1 | 1/2006 | Hossainy |
| 2006/0121012 A1 | 6/2006 | Kutryk et al. |
| 2006/0135476 A1 | 6/2006 | Kutryk et al. |
| 2006/0224231 A1 | 10/2006 | Gregorich |
| 2006/0224531 A1 | 10/2006 | Abrahao et al. |
| 2007/0042017 A1 | 2/2007 | Kutryk et al. |
| 2007/0055367 A1 | 3/2007 | Kutryk et al. |
| 2007/0123977 A1 | 5/2007 | Cottone et al. |
| 2007/0128723 A1 | 6/2007 | Cottone et al. |
| 2007/0129789 A1 | 6/2007 | Cottone et al. |
| 2007/0141107 A1 | 6/2007 | Kutryk et al. |
| 2007/0156232 A1 | 7/2007 | Kutryk et al. |
| 2007/0191932 A1 | 8/2007 | Kutryk et al. |
| 2007/0196422 A1 | 8/2007 | Kutryk et al. |
| 2007/0213801 A1 | 9/2007 | Kutryk et al. |

FOREIGN PATENT DOCUMENTS

| | | |
|---|---|---|
| EP | 0251476 | 1/1986 |
| EP | 0366564 | 2/1990 |
| EP | 0411621 | 2/1991 |
| EP | 0754064 | 3/1995 |
| EP | 0895473 | 2/1996 |
| EP | 0817620 | 1/1998 |
| EP | 0831754 | 4/1998 |
| EP | 0939661 | 9/1999 |
| EP | 0817620 | 1/2002 |
| EP | 1181943 | 2/2002 |
| EP | 1410812 | 10/2002 |
| EP | 1354942 | 10/2003 |
| JP | 10067687 | 3/1998 |
| WO | WO 03/66564 | 2/1990 |
| WO | 9112779 | 9/1991 |
| WO | WO 9112779 | 9/1991 |
| WO | WO 94/15583 | 7/1994 |
| WO | WO 96/00782 | 1/1996 |
| WO | WO 9600783 | 1/1996 |
| WO | 9729802 | 8/1997 |
| WO | WO 97/29802 | 8/1997 |
| WO | 9732571 | 9/1997 |
| WO | WO 97/32571 | 9/1997 |
| WO | WO 9732571 | 9/1997 |
| WO | 9815317 | 4/1998 |
| WO | WO 98/15317 | 4/1998 |
| WO | 9822541 | 5/1998 |
| WO | WO 9822541 | 5/1998 |
| WO | WO 98/34563 | 8/1998 |
| WO | WO 98/34563 A | 8/1998 |
| WO | 9932184 | 7/1999 |
| WO | 9935245 | 7/1999 |
| WO | 9936276 | 7/1999 |
| WO | WO 99/37337 | 7/1999 |
| WO | WO 9932184 | 7/1999 |
| WO | WO 9936276 | 7/1999 |
| WO | 9955360 | 11/1999 |
| WO | WO 99/55360 | 11/1999 |
| WO | WO 00/02998 | 1/2000 |
| WO | WO 00/40278 | 7/2000 |
| WO | WO 00/41648 | 7/2000 |
| WO | WO 00/50068 A2 | 8/2000 |
| WO | WO 0044357 | 8/2000 |
| WO | 00108683 | 2/2001 |
| WO | WO 01/15764 | 3/2001 |
| WO | WO 01/43696 | 6/2001 |

(56) References Cited

FOREIGN PATENT DOCUMENTS

| | | |
|---|---|---|
| WO | WO 01/68158 | 9/2001 |
| WO | 00194420 | 12/2001 |
| WO | WO 02/13883 | 2/2002 |
| WO | 02057436 | 7/2002 |
| WO | WO 02060416 | 8/2002 |
| WO | WO 02074925 | 9/2002 |
| WO | 02089727 | 11/2002 |
| WO | 02102430 | 12/2002 |
| WO | 02102971 | 12/2002 |
| WO | WO 02/102837 | 12/2002 |
| WO | 03016099 | 2/2003 |
| WO | 00012028 | 3/2003 |
| WO | 03019136 | 3/2003 |
| WO | WO 03/001936 | 3/2003 |
| WO | WO 03019136 | 3/2003 |
| WO | 03037400 | 5/2003 |
| WO | 03047557 | 6/2003 |
| WO | 03063575 | 8/2003 |
| WO | WO 03/065881 | 8/2003 |
| WO | 03085092 | 10/2003 |
| WO | WO 03/082203 A2 | 10/2003 |
| WO | WO 03082203 A2 | 10/2003 |
| WO | 02092108 | 11/2003 |
| WO | WO 2004/098451 | 11/2004 |
| WO | WO 2008/070304 | 6/2008 |

OTHER PUBLICATIONS

Asahara et al.,1997, Science 275:964967.*
Seeger et al., 1988, J. Vascular Surgery 8:476-482.*
Hotchin et al, 1999, J Cell Sci. 112:2937-3946.*
Akiyama et al ,1996, Hum Cell 9:181-6 (Abstract 2/2).*
Kong et al., 2004, Circulation 109:1769-1775.*
Parik et al (2000, Adv. Drug. Deliv. Rev. 42:139-161.*
Cioffi et al (1999, Gene Therapy 6:1153-1159.*
Boyer et al Jan. 2000, J. Vasc. Surg 31:181-189.*
Bos et al. Small-Diameter Vascular Graft Prostheses: Current Status Archives Physio, Biochem 106: 100-115, 1998.
Chemical and Engineering News, Apr. 9, 1991, p. 59.
Cook et al. Full Sci. Tech. 5(4) p. 695, 1997.
Kohler et al., Continious cultures of fused cells secreting antibody of predefined specificity Nature 265 pp. 495-497, 1975.
Jaffe et al. J. Clin. Invest., 52 pp. 2745-2757, 1973.
Jaffe, E.A., in Biology of Endothelial Cells, ed.; Martinus-Nijhoff, The Hague, 1984, table of contents.
Jaffe, E.A., "Cell Biology of Endothelial Cells", in Human Pathology, vol. 18, No. 3, Mar. 1987.
Reduction in thrombosis events with heparin-coated Palmaz-Schatz stents in normal porcine coronary arteries, Circulation 93 pp. 423-430.
Wilson, S.R. Biological Aspects of Fullerenes: Chemistry, Physics and Technology. Kadish et al. eds., John Wiley & Sons, NY, 2000 pp. 437-465.
Diglio CA, et al. *Isolation and characterization of cerebral resistance vessel endothelium in culture*, Tissue Cell 25(6): 833-46, Dec. 1993. PMID: 8140579 Abstract.
Gera Neufeld et al. *Vascular endothelial growth factor (VEGF) and its receptors*. The FASEB Journal. vol. 13, Jan. 1999, pp. 9-22, Dept. of Biology, Technion, Israel Institute of Technology, Israel.
Hennig Y. et al. Karyotype evolution in a case of uterine angioleiomyoma Cancer Genet. Cytogenet 108(1): 79-80, Jan. 1, 1999. PMID 9973929 Abstract.
Hristov et al. 2003 Endothelial Progenitor Cells Mobilization, Differentiation, and Homing. Arterioscler. Thromb. Vasc.
International Search Report PCT/US03/03645.
Isner et al. *Pro-endothelial Cell Approach to Restenosis* In: p. 55-80, 2001.
Kerr et al. 1999 Novel Small molecule alpha v intergrin antagonists; comparative anti-cancer efficacy with known angiogenesis inhibitors. Anticancer Res. Mar.-Apr.; 19(2A):959-968.

Miyazawa M, Nose M, Kawashima M, Kyogoku M. *Pathogenesis of arteritis of SL/Ni mice, Possible lytic effect of anti-gp70 antibodies on vascular smooth muscle cells*. J Exp. Med 166(4): 890-908, Oct. 1, 1987 PMID: 2888832 Abstract.
Nilbert M. et al. *Complex karyotypic changes, including rearrangements of 12q13 and 14q24, in two leiomyosarcomas*. Cancer Genet. Cytogenet. 48(2): 217-223, Sep. 1990. PMID: 2397453.
Olson NE, Kozlowski J, Reidy MA. *Proliferation of intimal smooth muscle cells. Attenuation of basic fibroblast growth factor 2-stimulated proliferation is associated with inclearsed expression of cell cycle inhibitors*. J. Biol. Chem Apr. 14, 2000; 275(15): 11270-7. PMID: 107537 [PubMed].
Poznansky et al. 1984 Biological approaches to the controlled delivery of drugs: a critical review. Pharmacol. Rev. 36:277-336.
Ross JS et al. *Atherosclerosis and cancer: common molecular pathways of disease development and progression* Ann. NY Acad. Sci. 947:271-92, Dec. 2001. PMID: 11795276.
Schwartz et al. eds., Principles of Surgery, Chapter 20, Arterial Dissease, $7^{th}$ Edition, McGraw-Hill Health Professions Division, New York, pp. 931-1003, 1999.
Stastny JJ, Fosslien E. *Quantitative alteration of some aortic intima proteins in fatty streaks and fibro-fatty lesions* Exp. Mol. Pathol. 57(3): 205-214, Dec. 1992. PMID: 1286671 Abstract.
Tamai H. in Handbook of Coronary Stents $3^{rd}$ Edition, Eds. PW Serruys and MJB Kutryk, Martin Dunitz, p. 297, 2000.
Teofili L, Martini M, Di Mario A, Rutella S, Urbana R, Luongo M, Leone G, Larocca LM. *Expression of p15(ink4b) gene during megakaryocytic differentiation of normal and myelodysplastic hematopoietic progenitors* Blood 98(2): 495-497, Jul. 15, 20011 PMID: 11435325.
Yasushi, et al., "Catheter-Based Prostacyclin Synthase Gene Transfer Prevents in-Stent Restenosis in Rabbit Atheromatous Arteries", Cardiovascular Research. 2004, vol. 61(1), pp. 177-185.
Sun et al., "In Vitro Expression of Calcitonin Gene-Related Peptide in Human Endothelial Cells Transfected with Plasmid and Retroviral Vectors", Neuropeptides, 1994, vol. 26(3), pp. 167-173.
Hunter et al., "In Vivo Gene Transfer of Prepro-Calcitonin Gene-Related Peptide to the Lung Attenuates Chronic Hypoxia-Induced Pulmonary Hypertension in the Mouse". Circulation, 2000, vol. 101(8), pp. 923-930.
Natasha et al., "Role of eNOS, CGRP and p53 in Vascular Smooth Muscle Cell Proliferation", Faseb Journal, 2003, vol. 17, No. 4-5, pages abstract No. 564.3.
European Search Report for European Patent Application No. 05 745 773.1.
Hotchin, et al., "Differential Activation of Focal Adhesion Kinase, Rho and Rac by the Ninth and Tenth FIII Domains of Fibronectin", Journal of Cell Science, 1999, vol. 112, pp. 2937-2946.
Akiyama, et al., "Integrins in Cell Adhesion and Signalin", Hum. Cell 1996, vol. 9, No. (3), pp. 181-186 (Abstract 2/2).
Seeger, et al., "Improved In Vivo Endotheliazation of Prosthetic Grafts by Surface Modification with Febronectin", J. Vascular Surgery, 1988, vol. 8, pp. 476-482.
Zhou, et al., "Unorthodox angiogenesis in skeletal muscle", Cardiovasc Res., Feb. 16, 2001, vol. 49, No. (3), pp. 634-646.
Nachman, et al., "Endothelial cell culture: beginnings of modern vascular biology", The Journal of Clinical Investigation, Oct. 2004, vol. (4), No. 8, 1037-1040.
Urbich, et al., "Endothelial progenitor cells characterization and role in vascular biology", Circulation Research, Aug. 20. 2004, pp. 343-353.
Kong, et al., "Enhanced inhibition of neointimal hyperplasia by genetically engineered endothelial progenitor cells", Circulation, 2004, 109, pp. 1769-1775, ISSN: 1524-4539.
Di Stefano, et al., "Modulation of arterial growth of the rabbit carotid artery associated with experimental elevation of blood flow", Journal of Vascular Research, 1998, vol. 35, No. 1, pp. 1-7.
Wu MH, et al., "Dynamic changes of smooth muscle and endothelial markers in the early healing process of Dacron vascular grafts in the dog, using RT-PCR", Int. J. Angiol . . . , Mar. 2000, vol. 9, No. (2), pp. 107-110.

(56) References Cited

OTHER PUBLICATIONS

Arras, et al., "Monocyte activation in angiogenesis and collateral growth in the rabbit hindlimb", Journal Clinical Investigation, Jan. 1998, vol. 101, No.(1), pp. 40-50.
Boyer, et al., "Isolation of endothelial cells and their progenitor cells from human peripheral blood", Journal of Vascular Surgery, Jan. 2000, vol. 3, No. (1), part 1., pp. 181-189.
Alamo, et al., "Comorbidity indices in hematopoietic stem cell transplantation: a new report card", Bone Marrow Transplantation, 2005, vol. 36, pp. 475-479.
Kerr, "Cell adhesion molecules in the pathogenesis of and host defence against microbial infection", J. Clin. Pathol.: Mol. Pathol., 1999, vol. 52, pp. 220-230.
Wojakowski, et al., "Mobilization of CD34/CXCR4+, CD34/CD117+, c-met+ stem cells, and mononuclear cells expressing early cardiac, muscle, and endothelial markers into peripheral blood in patients with acute myocardial infarction", Circulation, Nov. 16, 2004, vol. 110, pp. 3213-3220.
Neufeld, et al., "Vascular endothelial growth factor (VEGF) and its receptors", The FASEB Journal, Jan. 1999, vol. 13, pp. 9-22, Dept. of Biloogy*, Technion, Israel Institute of Technology.
U.S. Appl. No. 60/189,674, filed Mar. 15, 2000, Kutryk, M. et al.
U.S. Appl. No. 60/201,789, filed May 4, 2000, Kutryk, M. et al.
U.S. Appl. No. 60/566,829, filed Apr. 30, 2004, Kutryk, M. et al.
Aoyagi, Masaru et al, Smooth muscle cell proliferation, elastin formation, and tropoelastin transcripts during the development of intimal thickening in rabbit carotid arteries after endothelial denudation 1997 Histochemistry and Cell Biology vol. 107, No. 1, 1997, pp. 11-17.
Canadian Search Report for CA 2,555,364 filed Mar. 10, 2005.
Drevs J., et al 2003 Receptor Tyrosine Kinases: the main targets for new anticancer therapy. Curr. Drug targets.4(2):113-21.
International Search Report PCT/US06/44423 filed Nov. 15, 2006.
International Search Report PCT/US07/082034 Jun. 17, 2008.
Karnik, Satyajit K, A critical role for elastin signaling in vascular morphogenesis and disease, 2003 2003 Development (Cambridge) vol. 130, No. 2, 411-423.
Kohn, et al. Retroviral-Mediated Gene Transfer into Mammalian Cells. Blood Cells, 1987, pp. 285-298, vol. 13, Springer-Verlag New York, Inc.
Kohn, Joachim; Expert Rev. Med. Devices 2 (6) (2005) 667-671.
Morigi, et al. Verotoxin-1 induced up-regulation of adhesive molecules renders microvascular endothelial cells thrombogenic at high shear stress. Blood, Sep. 15, 2001, pp. 1828-1835, vol. 98, No. 6.
Numaguchi Y. et al., "Catheter-Based Prostacyclin Synthase Gene Transfer Prevents in-Stent Restenosis in Rabbit Atheromatous Arteries", Cardiovascular Research, 2004, vol. 61(1), pp. 177-185.
Phillips, et al. Tachykinin NK3 and NK1 receptor activation elicits secretion from porcine airway submucosal glands. British Journal of Pharmacology, 2003, pp. 254-260, vol. 138, UK.
Robinet, Arnaud et al, Elastin-derived peptides enhance angiogenesis by promoting endothelial cell migration and tubulogenesis through upregulation of MT1-MMP, 2005 J. Cell Science 118, No. 2, 343-356.
Scholz, et al. Ultrastructure and molecular histology of rabbit hind-limb collateral artery growth (arteriogenesis). Virchows Arch., Mar. 2000, pp. 257-270. vol. 436(3).
Silha, et al. Angiogenic factors are elevated in overweight and obese individuals. International Journal of Obesity, 2005, pp. 1308-1314, vol. 29, Nature Publishing Group.Published Online Jun. 7, 2005.
Siviter et al. Expression and Functional Characterization of a *Drosophila* Neuropeptide Precursor with Homology to Mammalian Preprotachykinin A. Journal of Biological Chemistry, Jul. 28, 2000, pp. 23273-23280, vol. 275, No. 30. JBC Papers in Press.First published May 8, 2000.
Skowasch, et al. Pathogen Burden, Inflammation, Proliferation and Apoptosis in Human In-Stent Restenosis—Tissue Characteristics Compared to Primary Atherosclerosis. Journal of Vascular Research, Oct. 28, 2004, pp. 525-534, vol. 41.
Sluijter, et al. Increase in Collagen Turnover but Not in Collagen Fiber Content is Associated with Flow-Induced Arterial Remodeling. Journal of Vascular Research, Nov. 10, 2004, pp. 546-555. vol. 41.
Uurto, Iikka et al; J. Endovasc. Therapy 2005; 12:371-379.
Van Royen, et al. Design of the START-trial: Stimulation of ARTeriogenesis using subcutaneous application of GM-CSF as a new treatment for peripheral vascular disease—A randomized, double-blind, placebo-controlled trial. Vasc Med., 2003, pp. 191-196, vol. 8(3).
Wlenta, et al. In vitro differentiation characteristics of cultured human mononuclear cells—implications for endothelial progenitor cell biology. Biochemical and Biophysical Research Communications, Jun. 8, 2005, pp. 476-482, vol. 333.
Wissink, et al. Endothelial cell seeding of heparinized collagen matrices—effect of bFGF pre-loading on proliferation after low density seeding and pro-coagulant factors. J Control Release, Jul. 3, 2000, pp. 141-155, vol. 67(2-3).
U.S. Appl. No. 60/354,680, filed Feb. 6, 2002.
U.S. Appl. No. 60/382,095, filed May 20, 2002.
U.S. Appl. No. 60/551,978, filed Mar. 10, 2004.
U.S. Appl. No. 60/736,920, filed Nov. 15, 2005.
U.S. Appl. No. 60/822,451, filed Aug. 15, 2000.
U.S. Appl. No. 60/822,465, filed Aug. 15, 2006.
U.S. Appl. No. 60/822,471, filed Aug. 15, 2006.
Alamo, et al. Comorbidity indices in hematopoietic stem cell transplantation: a new report card. Bone Marrow Transplantation, Jul. 4. 2005. pp. 475-479, vol. 36, Nature Publishing Group. Presented Apr. 15, 2005.
Aoyagi, Masaru et al. Smooth muscle cell proliferation, elastin formation, and tropoelastin transcripts during the development of intimal thickening in rabbit carotid arteries after endothelial denudation 1997 Histochemistry and Cell Biology vol. 107, No. 1, 1997, pp. 11-17.
Bilboa, G. et al. Adenoviral/retroviral vector chimeras: a novel strategy to achieve high-efficiency stable transduction in vivo. FASEB J. 11, 624-634 (1997).
Belle et al. 1997. Stent Endothelization. Circulation 95: 438-448.
Canadian Search Report CA 2555364 filed Mar. 10, 2005.
Chaudhury, Endothelial Progenitor Cells, Neointimal Hyperplasia, and Hemodialysis Vascular Access Dysfunction. Circulation 2005: 112: 3-5.
Davis et al. Inorganica Chim. Acta 272 p. 261. 1998.
Di Stefano , et al. Modulation of arterial growth of the rabbit carotid artery associated with experimental elevation of blood flow. J Vasc Res., Jan.-Feb. 1998, pp. 1-7, vol. 35(1).
Egginton, et al. Unorthodox angiogenesis in skeletal muscle. Cardiovasc Res. Feb. 16, 2001, pp. 634-646, vol. 49(3).
Erne, P. et al: Cardiovascular Intervent Radiol (2006) 29:11-16.
Ginnanouckakis, N. and Trucco, M. Gene therapy technology applied to disorders of glucose metabolism: promise, achievements and prospects. Biotechniques 35, No. 1, 122-145, 2003.
Harrison's Principles of Internal Medicine, 14the Edition, 1998, pp. 1287 and 1375-1380.
International Search Report for PCT/US2006/44423 Nov. 15, 2006.
International Search Report for PCT/US2006/44423 completed May 8, 2007 by USPTO Patent Office , Mail Stop PCT, Attn: ISA/US, Commissioner for Patents, P.O. Box 1450. Alexandria, Virginia 22313-1450.
International Search Report, International Application No. PCT/US2006/006526, International Filing Date, Feb. 24, 2006.
Ishida, et al. Dynamic Changes of Smooth Muscle and Endothelial Markers in the Early Healing Process of Dacron Vascular Grafts in the Dog, Using RE-PCR. Int. J. Angiol, Mar. 2000, pp. 107-110, vol. 9(2).
Kanda, et al. Isolation and characterization of novel tachykinins from the posterior salivary gland of the common octopus *Octopus vulgaris*. Peptides, 2003, pp. 35-43, vol. 24.
Karnik, Satyajit K, A critical role for elastin signaling in vascular morphogenesis and disease 2003 2003 Development (camridge) vol. 130. No. 2, 411-423.

(56) References Cited

OTHER PUBLICATIONS

Kasai, et al. Efficacy of peroxisome proliferative activated receptor (PPAR)-α ligands, fenofibrate, on intimal hyperplasia and constrictive remodeling after coronary angioplasty in porcine models. Atherosclerosis, 2005.
Kerr et al. 1999 Novel Small molecule alpha v intergrin antagonists; comparative anti-cancer efficacy with known angiogenesis inhibitors. Anticancer Res. Mar-Apr: 19(2A):959-968.
Kerr, JU. Cell adhesion molecules in the pathogenesis of and host defence against microbial infection. J. Clin. Pathol: Mol Pathol, 1999. 52: 220-230, UK.
Kohn, et al. Retroviral-Mediated Gene Transfer into Mammalian Cells. Blood Cells, 1987, pp. 285-298. vol. 13, Springer-Verlag New York, Inc.
Kohn, Joachim: Expert Rev. Med. Devices 2 (6) (2005) 667-671.
Kong, et al. Enhanced Inhibition of Neointimal hyperplasia by Genetically Engineered Endothelial Progenitor Cells. Circulation Research. Apr. 5, 2004, pp. 1769-1775. vol. 109.
Korshunov, et al. Plasminogen Activator Expression Correlates with Genetic Differences in Vascular Remodeling. Journal of Vascular Research, Oct. 28, 2004, pp. 481-490, vol. 41.
Kurjiaka, D.T. The Conduction of Dilation along an Arteriole is Diminished in the Cremaster Muscle of Hypertensive Hamsters. Journal of Vascular Research, Oct. 28, 2004. pp. 517-524, vol. 41.
Kurjiaka, D.T. The Conduction of Dilation along an Arteriole is Diminished in the Cremaster Muscle of hypertensive Hamsters. Journal of Vascular Research, Oct. 28, 2004, pp. 517-524, vol. 41.
Lio et al. New Concepts and Materials in Microvascular Grafting. Microsurgery 18 pp. 263-265. 1998.
Maeda, et al. Progenitor endothelial cells on vascular grafts: an ultrastructural study. J Biomed Mater Res., 2000, pp. 55-60, vol. 51(1).
Mark, N. Drug Eluting Stents—Polymeric Drug Encapsulation on Stents. Brown University Web Page Project, 2004.
Morigi, et al. Verotoxin-1 induced up-regulation of adhesive molecules renders microvascular endothelial cells thrombogenic at high shear stress. Blood, Sep. 15, 2001. pp. 1828-1835, vol. 98, No. 6.
Nachman, et al. Endothelial cell culture: beginnings of modern vascular biology. The Journal of Clinical Investigation, Oct. 2004, pp. 1037-1039. vol. 114, No. 8.
Naiki, et al. Flow-dependent concentration polarization of plasma proteins at the luminal surface of a semipermeable membrane. Biorheology, 1999, pp. 243-256, vol. 36(3).
Phillips, et al. Tachykinin NK3 and NK1 receptor activation elicits secretion from porcine airway submucosal glands. British Journal of Pharmacology, 2003, pp. 254-260, vol. 138. UK.
Principles of Surgery, Schwartz et al. eds., chap 20, Arterial Diseases. 7$^{th}$ Edition, McGraw-Hill Health Professions Divisions, N.Y. 1999.
Roninet, Arnaud et al. Elastin-derived peptides enhance angiogenesis by promoting endothelial cell migration and tubulogenesis through upregulation of MT1-MMP, 2005 J. Cell Science 118, No. 2, 343-356.
Salzmann, et al. Inflammation and neovascularization associated with clinically used vascular prosthetic materials. Cardiovasc Pathol., Mar.-Apr. 1999, pp. 63-71, vol. 8(2).
Scholz, et al. Ultrastructure and molecular histology of rabbit hind-limb collateral artery growth (arteriogenesis). Virchows Arch., Mar. 2000, pp. 257 -270. vol. 436(3).
Six-month assessment of a phase 1 trial of angiogenic gene therapy for the treatment of coronary artery disease using direct intramyocardial administration of an adenovirus vector expressing the VEGF 121 cDNA. Ann. Surg. 230(4): 466-470 (1999).
Severini, et al. The Tachykinin Peptide Family. Pharmacological Reviews, Jun. 2002, vol. 54, Issue 2.
Silha, et al. Angiogenic factors are elevated in overweight and obese individuals. International Journal of Obesity, 2005. pp. 1308-1314, vol. 29, Nature Publishing Group.Published Online Jun. 7, 2005.
Siviter, et al. Expression and Functional Characterization of a Drosophila Neuropeptide Precursor with Homology to Mammalian Preprotachykinin A. Journal of Biological Chemistry, Jul. 28, 2000. pp. 23273-23280, vol. 275, No. 30. JBC Papers in Press.First published May 8, 2000.
Siviter, et al. Expression and Functional Characterization of a Drosophila Neuropeptide Precursor with Homology to Mammalian Preprotachykinin A. Journal of Biological Chemistry, Jul. 28, 2000, pp. 23273-23280, vol. 275, No. 30. JBC Papers in Press.First published May 8, 2000.
Skowasch, et al. Pathogen Burden, Inflammation, Proliferation and Apoptosis in Human In-Stent Restenosis—Tissue Characteristics Compared to Primary Atherosclerosis. Journal of Vascular Research. Oct. 28, 2004. pp. 525-534. vol. 41.
Sluijter, et al. Increase in Collagen Turnover but Not in Collagen Fiber Content is Associated with Flow-Induced Arterial Remodeling. Journal of Vascular Research, Nov. 10, 2004. pp. 546-555. vol. 41.
Teebken, et al. Tissue engineering of vascular grafts: human cell seeding of decellularised porcine matrix. Eur J Vasc Endovasc Surg., Apr. 2000, pp. 381-386, vol. 19(4).
Urbich, et al. Endothelial Progenitor Cells—Characterization and Role in Vascular Biology. Circulation Research, Aug. 20, 2004. pp. 343-353, vol. 95.
Uurto, Iikka et al; J. Endovasc. Therapy 2005: 12:371-379.
Vendartran, S. S.; Biomaterials 27 (206) 1573-1578.
Van Royen, et al. Design of the START-trial: Stimulation of ARTeriogenesis using subcutaneous application of GM-CSF as a new treatment for peripheral vascular disease—A randomized, double-blind, placebo-controlled trial. Vase Med., 2003, pp. 191-196, vol. 8(3).
Van Royen, et al. Local Monocyte Chemoattractant Protein-1 Therapy Increases Collateral Artery Formation in Apolipoprotein E-Deficient Mice but Induces Systemic Monocytic CD11b Expression, Neointimal Formation, and Plaque Progression. Circulation Research, 2003, vol. 92.
Walenta, et al. In vitro differentiation characteristics of cultured human mononuclear cells—implications for endothelial progenitor cell biology. Biochemical and Biophysical Research Communications, Jun. 8, 2005, pp. 476-482, vol. 333.
Wickenhauser, et al. Structural, antigenetic and transcriptional characteristics in peripheral blood CD34+ progenitor cells from polycythemia vera patients: Evidence for delayed determination. International Journal of Oncology, 2003, pp. 437-443, vol. 23.
Wissink, et al. Endothelial cell seeding of heparinized collagen matrices—effecg of bFGF pre-loading on proliferation after low density seeding and pro-coagulant factors. J Control Release. Jul. 3, 2000, pp. 141-155, vol. 67(2-3).
Zisch, A.H. Tissue engineering of angiogenesis with autologous endothelial progenitor cells. Current Opinion in Biotechnology, 2004, pp. 424-429, vol. 15.
Liu et al. Fullerene Pipes. Science 280 pp. 1253-1256, 1998.
Asahara et al. Isolation of putative progenitor endothelial cells fro angiogenesis. Science 275: 964-967, 1997.
Van Belle et al. Stent Endothelialization. Circulation 95: 438-448, 1997.
Dekker A. et al, Improved adhesion and proliferation of human endothelial cells on polyethylene precoated with monoclonal antibodies directed against cell membrane antigens and extracellular matrix proteins, Thrombosis and Haemostasis, 66: 715-724, 1991; ISSN: 0340-6245.
Schatz et al. 2000 Human endometrial endothelial cells: Biol. Reprod. 62: 691-697.
Mendel et al. 2003 In Vivo antitumor activity of SU11248, a novel tyrosine kinase inhibitor targeting vascular endothelial growth factor . . . Clin. Cancer Res. Jan. 9(1): 327-337.
Davis et al. The immobilisation of proteins in carbon nanotubes. Inorganica Chim. Acta 272: 261, 1998.
Takahashi et al. Ischemia- and cytokine-induced mobilization of bone marrow-derived endothelial progenitor cells for neovascularization. Nat. Med. 1999;5 pp. 434-438.
Kalka et al. VEGF Gene Transfer Mobilizes Endothelial Progenitor Cells in Patients with Inoperable Coronary Disease. ANN Thorac. Surg. 2000;70: 829-834.

(56) References Cited

OTHER PUBLICATIONS

Harrison's Principles of Internal Medicine, 13th Edition, 1994, pp. 939-946 and 1375-1380.
Rosengart et al. Six-month assessment of phase I trial of angiogenic gene therapy for the treatment of coronary artery disease using direct intramyocardial administration of an adenovirus vector expressing the VEGF 121 cDNA. Ann. Surg. 230(4): 466-470, 1999.
Lio et al. New concepts and Materials in Microvascular Grafting. Microsurgery 18:263-256, 1998.
Laird et al. 2002 SU6668 inhibits FLK-1/KDR and PDGFR beta in Vivo, resulting in rapid apoptosis of tumor vasculature and tumor regression in mice. FASEB J. May; 16(7): 681-690.
Hardhammar et al. Reduction in thrombonic events with heparin-coated Palmaz-Schatz stents in normal porcine coronary arteries, Circulation 93: 423-430, 1996.
Van Beusekom et al. Cardiovasc. Pathol. 5: 69-76, 1996.
Suryapranata et al., 1998. Randomized comparison of coronary stenting with balloon angioplasty in selected patients with acute myocardial infarction. Circulation 97: 2502.
Weimer et al., Influence of a poly-ethyleneglycol spacer on antigen capture by immobilized antibodies. J. Biochem. Biophys. Methods 45: 211-219, 2000.
Yamago et al., Chemical Derivatization of Organofullerenes through Oxidation, Reduction and C—O and C—C Bond Forming Reactions. J.Org. Chem., 58: 4796-798, 1998.
Rodgers, GM. Hematopoietic properties of normal and perturbed vascular cells. FASEB J. 1988; 2:116-123.
Yin et al. AC133, a novel marker for human hematopoietic stem and progenitor cells. Blood 1997; 90: 5002-5012.
Shi et al. Evidence for circulating bone marrow-derived endothelial cells. Blood 1998; 92: 362-367.
Gehling et al. In vitro differentiation of endothelial cells from AC133 progenitor cells. Blood 2000, 5:31-3112.
Lin et al. Origins of circulating endothelial cells and endothelial outgrowth from blood. J. Clin. Invest. 2000; 105: 71-77.
Di Campli et al. 2003 A medicine based on cell transplantation—Is there a future for treating liver diseases? *Aliment. Pharmacol. Ther.* Sep. 1; 18(5): 473-480 (Abstract).
Slavin et al. 2002 Adoptive cellular gene therapy of autoimmune disease. *Autoimmun. Rev.* Aug; 1(4): 213-219.
Herder et al. 2003 Sustained Expansion and Transgene Expression of Coagulation Factor VIII—Transduced Cord Blood-Derived Endothelial Progenitor Cells, *Hypertension*. 23: 2266-2272.
Griese et al. 2003 Isolation and Transplantation of Autologous Circulating Endothelial Cells into Denuded Vessels and Prosthetic Grafts . . . *Circulation* 108:2710-2715.
Pearson, D. 2000 Using Endothelial Cells for Gene Therapy. *Atrheroscler. Thromb Vasc. Biol.* 23:2117-2118.

\* cited by examiner

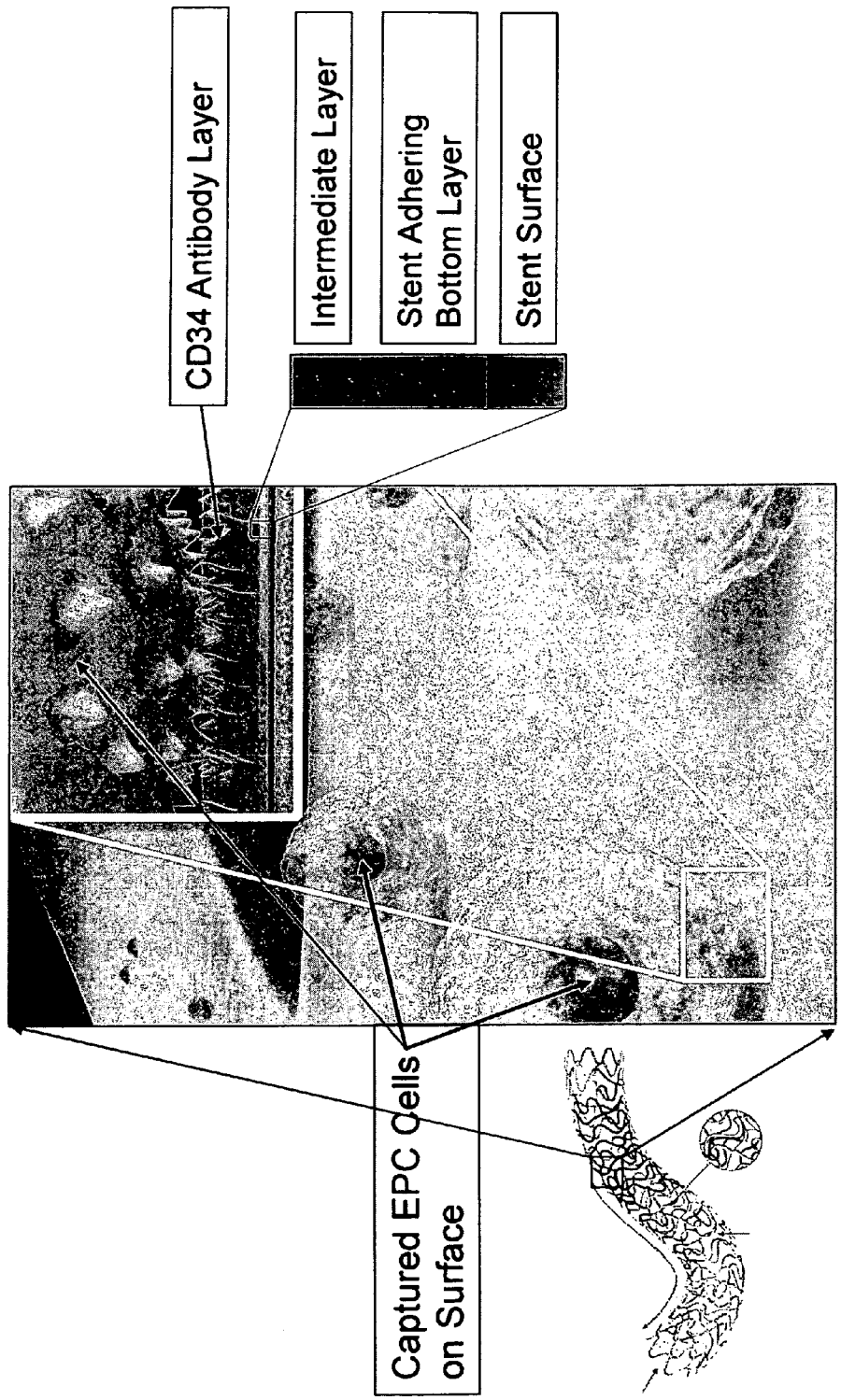

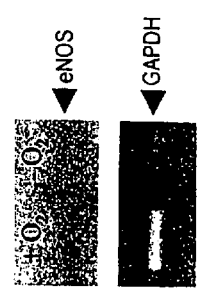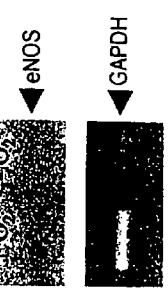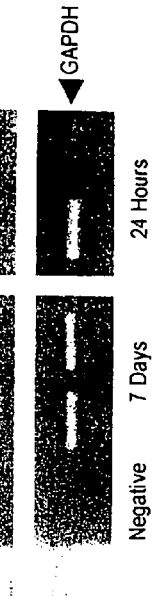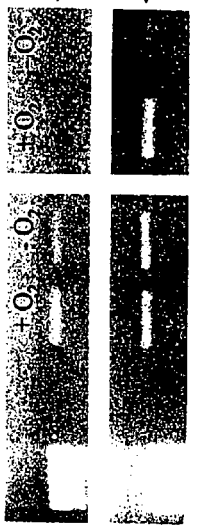

Bare SST

All images at 20X

HUVEC Staining

Gelatin + Ab

Gelatin

CMDx + Ab

CMDX

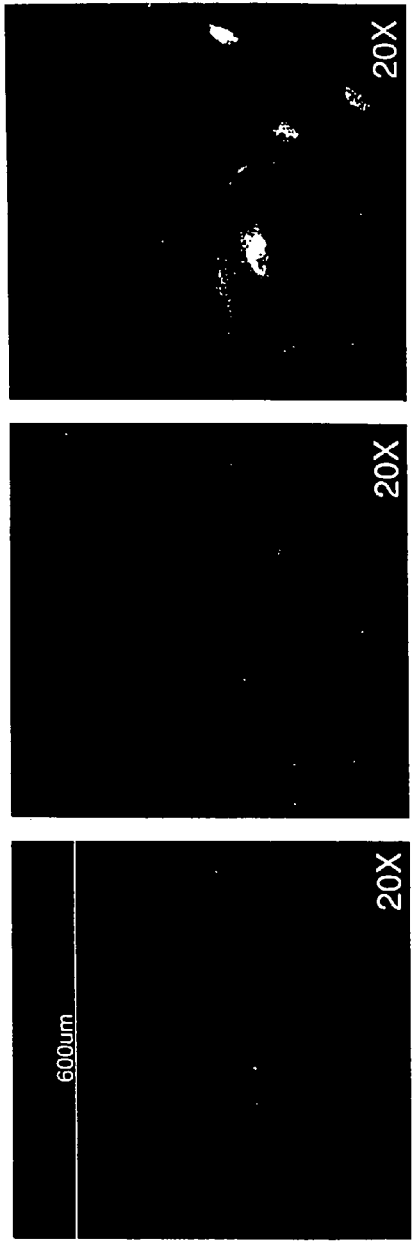

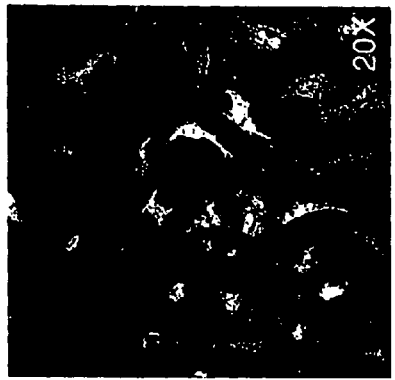
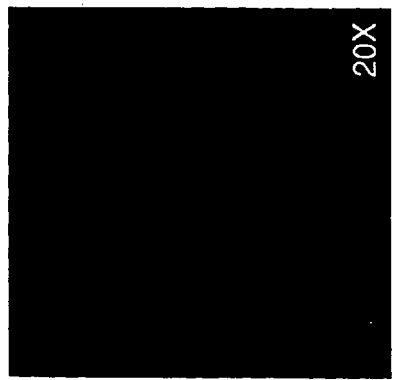
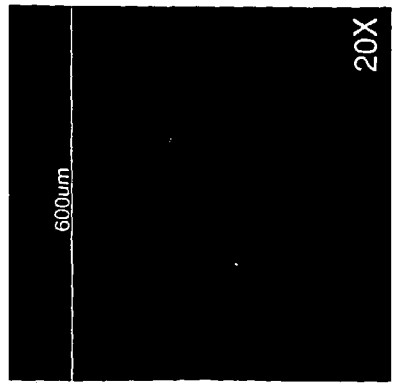
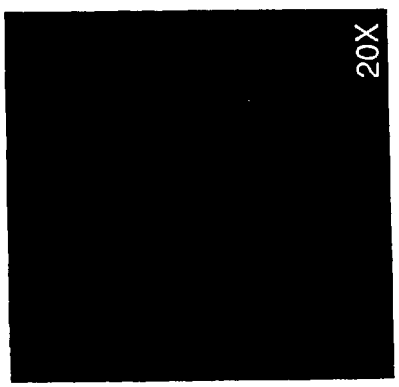
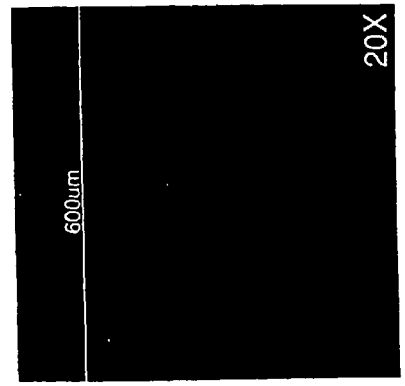

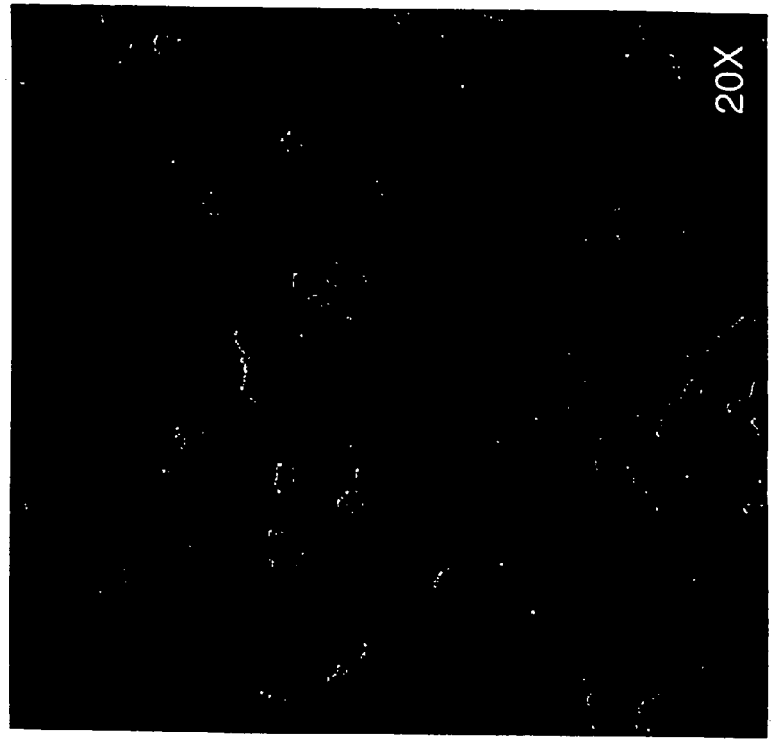
PEC Staining - 7 day (KDR)
FIG. 8B KDR with FITC secondary
FIG. 8A PI Nuclear Staining

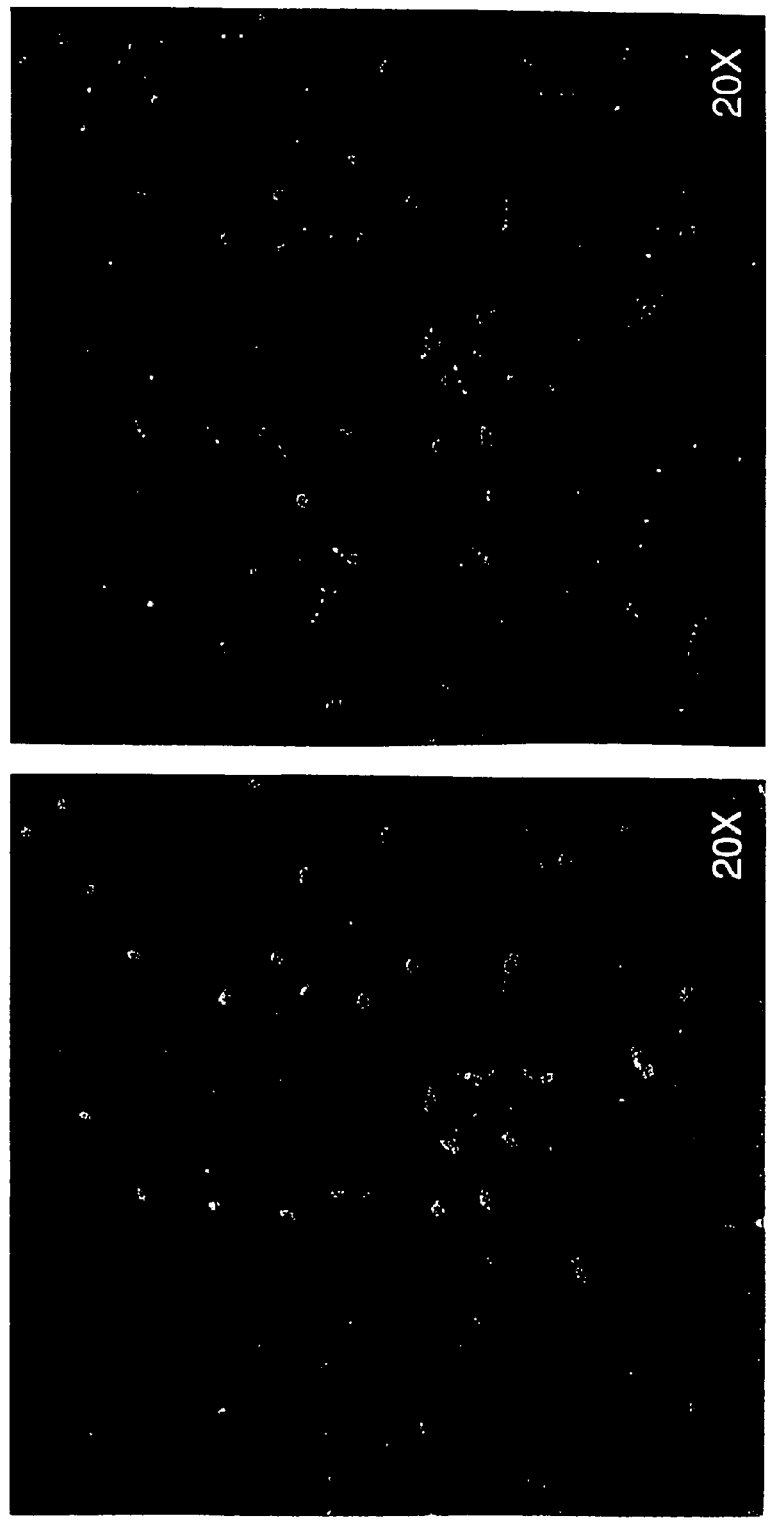

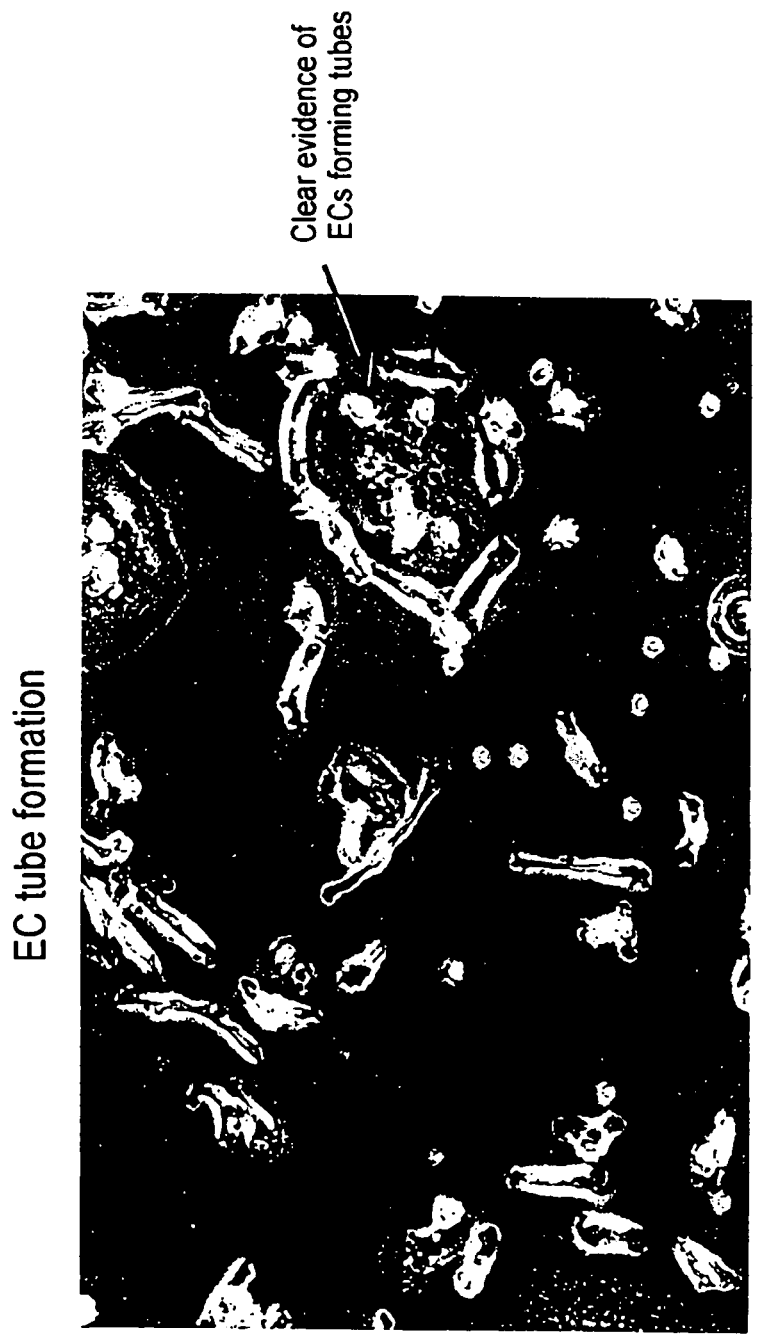

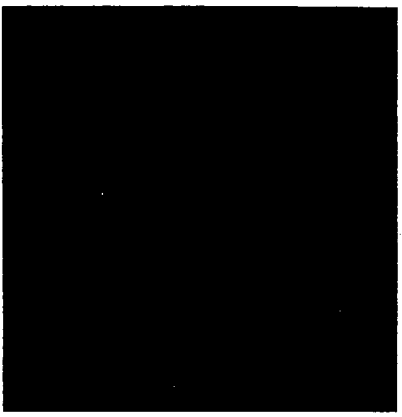
FIG. 12A
FIG. 12B
FIG. 12C
FIG. 12D

Intimal Hyperplasia in Stented Artery Segments
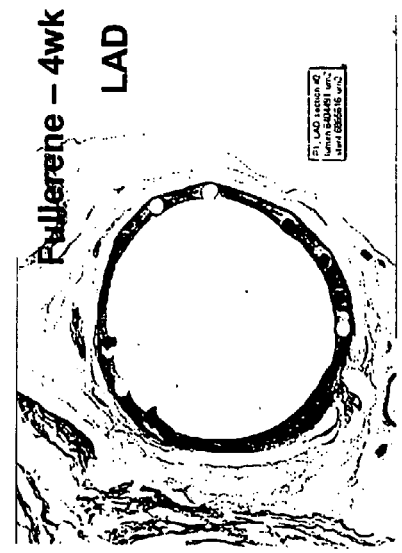
FIG. 13A Control – 4wk LAD
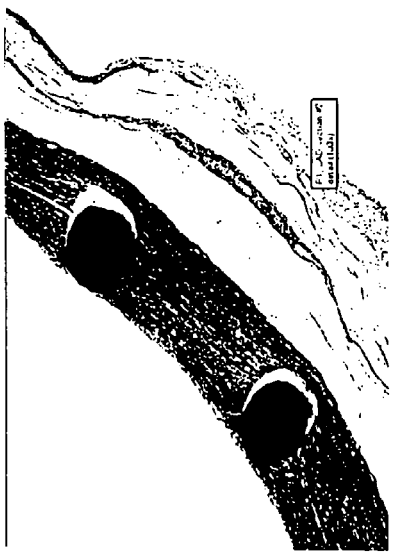
FIG. 13B Fullerene – 4wk LAD
FIG. 13C
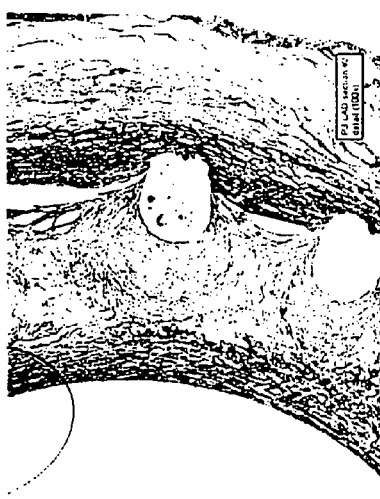
FIG. 13D In Vivo EPC Capture - 1 Hour Explant
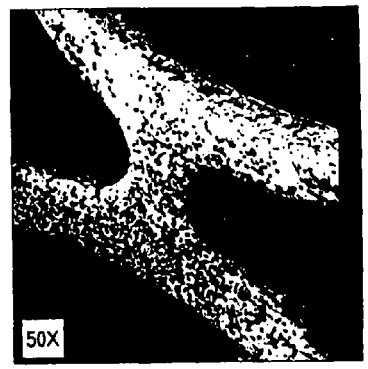
Dextran coated
FIG. 14A
Dextran + Ab coated
FIG. 14B
In Vivo EPC Capture - 48 hours
FIG. 14C   FIG. 14D
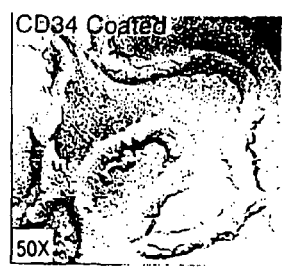 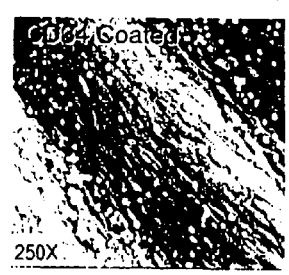 
FIG. 14E      FIG. 14F      FIG. 14G

Bare SST
Control – 4wk

Dextran Base Coating –
4wk

Dextran w / CD34 Ab – 4wk

In Vivo EPC Capture - 28 Day Histology

Bare SST
Control – 4wk

Dextran Base Coating –

Dextran w / CD34 Ab – 4wk

FIG. 15A
FIG. 15B
FIG. 15C
In Vivo EPC Capture
3.0 mm R stents with Antibody
48 hours post implant
Stained with anti VEGFR-2

MEDICAL DEVICE WITH COATING FOR CAPTURING GENETICALLY-ALTERED CELLS AND METHODS FOR USING SAME

This application is a continuation-in-part of U.S. patent application Ser. No. 10/360,567, filed on Feb. 6, 2003 now abandoned, and U.S. patent application Ser. No. 09/808,867, filed on Mar. 15, 2001 now U.S. Pat. No. 7,037,332, which claims benefit of U.S. provisional application No. 60/189,674, filed on Mar. 15, 2000 and U.S. provisional application No. 60/201,789, filed on May 4, 2000.

FIELD OF INVENTION

The invention relates to medical devices for implantation into vessels or hollowed organs of patients such as coated stents, stent grafts, synthetic vascular grafts, heart valves, catheters and vascular prosthetic filters for treating various diseases. In particular, the invention relates to medical devices comprising a coating on the surface that contacts blood, which coating is engineered to capture cells on the surface of the device. The captured cells form a monolayer on the surface of the device and are useful in many therapeutic applications, such as a drug delivery system or in the treatment of vascular disease. For example, the cells binding to the implanted medical device may be native, progenitor endothelial cells from the circulating blood or genetically modified in vitro to express and secrete molecules or substances in vivo having a local or generalized therapeutic effect in the patient.

BACKGROUND OF INVENTION

Diseases such as atherosclerosis and cancer are two of the leading causes of death and disability in the world. Atherosclerosis involves the development of fatty plaques on the luminal surface of arteries. These fatty plaques causes narrowing of the cross-sectional area of the artery. Ultimately, blood flow distal to the lesion is reduced causing ischemic damage to the tissues supplied by the artery.

Coronary arteries supply the heart with blood. Coronary artherosclerosis or coronary artery disease (CAD) is the most common, serious, chronic, life-threatening illness in the United States, affecting more than 11 million persons. The social and economic costs of coronary atherosclerosis vastly exceed those of most other diseases. Narrowing of the coronary artery lumen affects heart muscle resulting first in angina, followed by myocardial infarction and finally death, and more than three hundred thousand of those patients die before reaching the hospital. (*Harrison's Principles of Internal Medicine,* 14th Edition, 1998).

CAD can be treated using percutaneous translumenal coronary angioplasty (PTCA). More than 400,000 PTCA procedures are performed each year in the United States. In PTCA, a balloon catheter is inserted into a peripheral artery and threaded through the arterial system into the blocked coronary artery. The balloon is then inflated, the artery stretched, and the obstructing fatty plaque flattened, thereby increasing the cross-sectional flow of blood through the affected artery. The therapy, however, does not usually result in a permanent opening of the affected coronary artery. As many as 50% of the patients who are treated by PTCA require a repeat procedure within six months to correct a re-narrowing of the coronary artery. Medically, this re-narrowing of the artery after treatment by PTCA is called restenosis. Acutely, restenosis involves recoil and shrinkage of the vessel. Subsequently, recoil and shrinkage of the vessel are followed by proliferation of medial smooth muscle cells in response to injury of the artery from PTCA. In part, proliferation of smooth muscle cells is mediated by release of various inflammatory factors from the injured area including thromboxane $A_2$, platelet derived growth factor (PDGF) and fibroblast growth factor (FGF). A number of different techniques have been used to overcome the problem of restenosis, including treatment of patients with various pharmacological agents or mechanically holding the artery open with a stent. (*Harrison's Principles of Internal Medicine,* 14th Edition, 1998).

Of the various procedures used to overcome restenosis, stents have proven to be the most effective. Stents are metal scaffolds that are positioned in the diseased vessel segment to create a normal vessel lumen. Placement of the stent in the affected arterial segment prevents recoil and subsequent closing of the artery. Stents can also prevent local dissection of the artery along the medial layer of the artery. By maintaining a larger lumen than that created using PTCA alone, stents reduce restenosis by as much as 30%. Despite their success, stents have not eliminated restenosis entirely. (Suryapranata et al. 1998. Randomized comparison of coronary stenting with balloon angioplasty in selected patients with acute myocardial infarction. *Circulation* 97:2502-2502).

Narrowing of the arteries can occur in vessels other than the coronary arteries, including the aortoiliac, infrainguinal, distal profunda femoris, distal popliteal, tibial, subclavian and mesenteric arteries. The prevalence of peripheral artery atherosclerosis disease (PAD) depends on the particular anatomic site affected as well as the criteria used for diagnosis of the occlusion. Traditionally, physicians have used the test of intermittent claudication to determine whether PAD is present. However, this measure may vastly underestimate the actual incidence of the disease in the population. Rates of PAD appear to vary with age, with an increasing incidence of PAD in older individuals. Data from the National Hospital Discharge Survey estimate that every year, 55,000 men and 44,000 women had a first-listed diagnosis of chronic PAD and 60,000 men and 50,000 women had a first-listed diagnosis of acute PAD. Ninety-one percent of the acute PAD cases involved the lower extremity. The prevalence of comorbid CAD in patients with PAD can exceed 50%. In addition, there is an increased prevalence of cerebrovascular disease among patients with PAD.

PAD can be treated using percutaneous translumenal balloon angioplasty (PTA). The use of stents in conjunction with PTA decreases the incidence of restenosis. However, the post-operative results obtained with medical devices such as stents do not match the results obtained using standard operative revascularization procedures, i.e., those using a venous or prosthetic bypass material. (*Principles of Surgery,* Schwartz et al. eds., Chapter 20, *Arterial Disease,* 7th Edition, McGraw-Hill Health Professions Division, New York 1999).

Preferably, PAD is treated using bypass procedures where the blocked section of the artery is bypassed using a graft. (*Principles of Surgery,* Schwartz et al. eds., Chapter 20, *Arterial Disease,* 7th Edition, McGraw-Hill Health Professions Division, New York 1999). The graft can consist of an autologous venous segment such as the saphenous vein or a synthetic graft such as one made of polyester, polytetrafluoroethylene (PTFE), or expanded polytetrafluoroethylene (ePTFE), or other polymeric materials. The post-operative patency rates depend on a number of different factors, including the lumenal dimensions of the bypass graft, the type of synthetic material used for the graft and the site of outflow. Excessive intimal hyperplasia and thrombosis, however, remain significant problems even with the use of bypass grafts. For example, the patency of infrainguinal bypass procedures at 3 years using an ePTFE bypass graft is 54% for a femoral-popliteal bypass and only 12% for a femoral-tibial bypass.

Consequently, there is a significant need to improve the performance of stents, synthetic bypass grafts, and other chronic blood contacting surfaces and or devices, in order to further reduce the morbidity and mortality of CAD and PAD.

With stents, the approach has been to coat the stents with various anti-thrombotic or anti-restenotic agents in order to reduce thrombosis and restenosis. For example, impregnating stents with radioactive material appears to inhibit restenosis by inhibiting migration and proliferation of myofibroblasts. (U.S. Pat. Nos. 5,059,166, 5,199,939 and 5,302,168). Irradiation of the treated vessel can cause severe edge restenosis problems for the patient. In addition, irradiation does not permit uniform treatment of the affected vessel.

Alternatively, stents have also been coated with chemical agents such as heparin, phosphorylcholine, rapamycin, and taxol, all of which appear to decrease thrombosis and/or restenosis. Although heparin and phosphorylcholine appear to markedly reduce thrombosis in animal models in the short term, treatment with these agents appears to have no long-term effect on preventing restenosis. Additionally, heparin can induce thrombocytopenia, leading to severe thromboembolic complications such as stroke. Therefore, it is not feasible to load stents with sufficient therapeutically effective quantities of either heparin or phosphorylcholine to make treatment of restenosis in this manner practical.

Synthetic grafts have been treated in a variety of ways to reduce postoperative restenosis and thrombosis. (Bos et al. 1998. Small-Diameter Vascular Graft Prostheses: Current Status *Archives Physio. Biochem.* 106:100-115). For example, composites of polyurethane such as meshed polycarbonate urethane have been reported to reduce restenosis as compared with ePTFE grafts. The surface of the graft has also been modified using radiofrequency glow discharge to fluorinate the polyterephthalate graft. Synthetic grafts have also been impregnated with biomolecules such as collagen. However, none of these approaches has significantly reduced the incidence of thrombosis or restenosis over an extended period of time.

The endothelial cell (EC) layer is a crucial component of the normal vascular wall, providing an interface between the bloodstream and the surrounding tissue of the blood vessel wall. Endothelial cells are also involved in physiological events including angiogenesis, inflammation and the prevention of thrombosis (Rodgers G M. FASEB J 1988; 2:116-123.). In addition to the endothelial cells that compose the vasculature, recent studies have revealed that ECs and endothelial progenitor cells (EPCs) circulate postnatally in the peripheral blood (Asahara T, et al. Science 1997; 275: 964-7; Yin A H, et al. Blood 1997; 90:5002-5012; Shi Q, et al. Blood 1998; 92:362-367; Gehling U M, et al. Blood 2000; 95:3106-3112; Lin Y, et al. J Clin Invest 2000; 105:71-77). EPCs are believed to migrate to regions of the circulatory system with an injured endothelial lining, including sites of traumatic and ischemic injury (Takahashi T, et al. Nat Med 1999; 5:434-438). In normal adults, the concentration of EPCs in peripheral blood is 3-10 cells/mm$^3$ (Takahashi T, et al. Nat Med 1999; 5:434-438; Kalka C, et al. Ann Thorac Surg. 2000; 70:829-834). It is now evident that each phase of the vascular response to injury is influenced (if not controlled) by the endothelium. It is believed that the rapid re-establishment of a functional endothelial layer on damaged stented vascular segments may help to prevent these potentially serious complications by providing a barrier to circulating cytokines, preventing the adverse effects of a thrombus, and by their ability to produce substances that passivate the underlying smooth muscle cell layer. (Van Belle et al. 1997. Stent Endothelialization. *Circulation* 95:438-448; Bos et al. 1998. Small-Diameter Vascular Graft Prostheses: Current Status *Archives Physio. Biochem.* 106:100-115).

Endothelial cells have been encouraged to grow on the surface of stents by local delivery of vascular endothelial growth factor (VEGF), an endothelial cell mitogen, after implantation of the stent (Van Belle et al. 1997. Stent Endothelialization. *Circulation* 95:438-448.). While the application of a recombinant protein growth factor VEGF in saline solution at the site of injury induces desirable effects, the VEGF is delivered after stent implantation using a channel balloon catheter. This technique is not desirable since it has demonstrated that the efficiency of a single dose delivery is low and produces inconsistent results. Therefore, this procedure cannot be reproduced accurately every time.

Synthetic grafts have also been seeded with endothelial cells, but the clinical results with endothelial seeding have been generally poor, i.e., low post-operative patency rates (Lio et al. 1998. New concepts and Materials in Microvascular Grafting: Prosthetic Graft Endothelial Cell Seeding and Gene Therapy. *Microsurgery* 18:263-256) due most likely to the fact the cells did not adhere properly to the graft and/or lost their EC function due to ex-vivo manipulation.

Endothelial cell growth factors and environmental conditions in situ are therefore essential in modulating endothelial cell adherence, growth and differentiation at the site of blood vessel injury. Accordingly, with respect to restenosis and other blood vessel diseases, there is a need for the development of new methods and compositions for coating medical devices, including stents and synthetic grafts, which would promote and accelerate the formation of a functional endothelium on the surface of implanted devices so that a confluent EC monolayer is formed on the target blood vessel segment or grafted lumen thereby inhibiting neo-intimal hyperplasia.

In regard to diseases such as cancer, most therapeutic agents used to date have generalized systemic effects on the patient, not only affecting the cancer cells, but any dividing cell in the body due to the use of drugs in conventional oral or intravenous formulations. Yet in many cases, systemic administration is not effective due to the nature of the disease that is in need of treatment and the properties of the drug such as solubility, in vivo stability, bioavailability, etc. Upon systemic administration, the drug is conveyed by blood circulation and distributed into body areas including normal tissues. At diseased sites, the drug concentration is first low and ineffective which frequently increases to toxic levels, while in non-diseased areas, the presence of the drug causes undesired side effect. In certain instances, drugs are readily susceptible to metabolic degradation after being administered. Therefore, drug dose is often increased to achieve pharmacological efficacy and prolong duration, which causes increased systemic burden to normal tissues as well as cost concern for the patient. In other instances, the therapeutic potential of some potent drugs cannot be fulfilled due to their toxic side effects.

Therefore, much effort has been made to improve efficacy and targeting of drug delivery systems. For example, the use of liposomes to deliver drugs has been advantageous in that, in general, they increase the drug circulation time in blood, reduce side effects by limiting the concentration of free drug in the bloodstream, decrease drug degradation, prolong the therapeutic effect after each administration, reduce the need for frequent administration, and reduce the amount of drug needed. However, liposome systems that are currently available show limited efficiency of delivering drugs to target sites in vivo. See Kaye et al., 1979, Poznansky et al. 1984, U.S. Pat. Nos. 5,043,165, and 4,920,016.

To yield highly efficient delivery of therapeutic compounds, viral vectors able to incorporate transgenic DNA have been developed, yet the number of successful clinical applications has been limited. Despite the number of successes in vitro and in animal models, gene transfer technology is therefore proposed to marry with cell therapy. The ex vivo transfer of gene combinations into a variety of cell types will likely prove more therapeutically feasible than direct in vivo vector transfer. See Kohn et al., 1987, Bilbao et al., 1997, and Giannoukakis et al. 2003.

More recently local drug delivery vehicles such as drug eluting stents (DES) have been developed. See U.S. Pat. Nos. 6,273,913, 6,258,121, and 6,231,600. However, drug eluting stents of the prior art are limited by many factors such as, the type of drug, the amount of drug to be released and the amount of time it takes to release the drug. Other factors which need to be considered in regards to drug eluting stents are the drug interactions with other stent coating components, such as polymer matrices, and individual drug properties including hydrophobicity, molecular weight, intactness and activity after sterilization, as well as efficacy and toxicity. With respect to polymer matrices of drug eluting stents, one must consider the polymer type, polymer ratio, drug loading capability, and biocompatibility of the polymer and the drug-polymer compatibility such as drug pharmacokinetics.

Additionally, the drug dose in a drug eluting stent is pre-loaded and an adjustment of drug dose upon individual conditions and need cannot be achieved. In regard to drug release time, drug eluting stents instantly start to release the drug upon implantation and an ideal real-time release cannot be achieved.

It is therefore a long-felt need to develop an efficient systemic and local drug delivery system to overcome limitations of current available techniques. The present invention provides a system for the delivery of therapeutic agents locally or systemically in a safe and controlled manner.

SUMMARY OF INVENTION

It is an object of the invention to provide a therapeutic, drug delivery system and method for treating diseases in a patient. The therapeutic or drug delivery system comprises a medical device with a coating composed of a matrix comprising at least one type of ligand for recognizing and binding target cells such as progenitor endothelial cells or genetically-altered mammalian cells and genetically-altered mammalian cells which have been at least singly or dually-transfected.

The medical device of the invention can be any device that is implantable into a patient. For example, in one embodiment the device is for insertion into the lumen of a blood vessels or a hollowed organ, such as stents, stent grafts, heart valves, catheters, vascular prosthetic filters, artificial heart, external and internal left ventricular assist devices (LVADs), and synthetic vascular grafts, for the treatment of diseases such as cancer, vascular diseases, including, restenosis, artherosclerosis, thrombosis, blood vessel obstruction, or any other applications additionally covered by these devices.

In one embodiment, the coating on the present medical device comprises a biocompatible matrix and at least one type of substance or ligand, which specifically recognize and bind target cells such as progenitor endothelial cells such as in the prevention or treatment of restenosis, or genetically-altered mammalian cells, onto the surface of the device, such as in the treatment of blood vessel remodeling and cancer.

Additionally, the coating of the medical device may optionally comprise at least an activating compound for regulating the expression and secretion of the engineered genes of the genetically-altered cells. Examples of activator stimulatory compounds, include but is not limited to chemical moieties, and peptides, such as growth factors. In embodiments of the invention when the coating comprises at least one compound, the activator molecule or compound may function to stimulate the cells to express and/or secrete at least one therapeutic substance for the treatment of disease.

In one embodiment, the coating on the medical device comprises a biocompatible matrix which comprises an outer surface for attaching a therapeutically effective amount of at least one type of ligand such as an antibody, antibody fragment, or a combination of the antibody and the antibody fragment, or at least one type of molecule for binding the engineered marker on the surface of the genetically-modified cell. The present antibody or antibody fragment recognizes and binds an antigen or the specific genetically-engineered cell surface marker on the cell membrane or surface of target cells so that the cells are immobilized on the surface of the device. In one embodiment, the coating may optionally comprise an effective amount of at least one compound for stimulating the immobilized progenitor endothelial cells to either accelerate the formation of a mature, functional endothelium if the target cells are circulating progenitor cells, or to stimulate the bound cells to express and secrete the desired gene products if the target are genetically-altered cells on the surface of the medical device.

The medical device of the invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a suture, a vascular anastomosis clip, an indwelling venous or arterial catheter, a vascular sheath and a drug delivery port. The medical device can be made of numerous materials depending on the device. For example, a stent of the invention can be made of stainless steel, Nitinol (NiTi), or chromium alloy and biodegradable materials. Synthetic vascular grafts can be made of a cross-linked PVA hydrogel, polytetrafluoroethylene (PTFE), expanded polytetrafluoroethylene (ePTFE), porous high density polyethylene (HDPE), polyurethane, and polyethylene terephthalate, or biodegradable materials.

The biocompatible matrix forming the coating of the present medical device comprises without limitation a synthetic material such as polyurethanes, segmented polyurethane-urea/heparin, poly-L-lactic acid, cellulose ester, polyethylene glycol, polyvinyl acetate, dextran and gelatin, and/or naturally-occurring material such as basement membrane components such as collagen, elastin, laminin, fibronectin, vitronectin, heparin, fibrin, cellulose, and amorphous carbon, or fullerenes.

In an embodiment of the invention, the medical device comprises a biocompatible matrix comprising fullerenes. In this embodiment, the fullerene can range from about $C_{20}$ to about $C_{150}$ in the number of carbon atoms, and more particularly, the fullerene is $C_{60}$ or $C_{70}$. The fullerene of the invention can also be arranged as nanotubes on the surface of the medical device.

In one embodiment of the invention, the ligand is applied to the blood contacting surface of the medical device and the ligand specifically recognizes and binds a desired component or epitope on the surface of target cells in the circulating blood. In one embodiment, the ligand is specifically designed to recognize and bind only the genetically-altered mammalian cell by recognizing only the genetically-engineered marker molecule on the cell membrane of the genetically-altered cells. The binding of the target cells immobilizes the cells on the surface of the device.

In one embodiment, the ligand on the surface of the medical device for binding the genetically-altered cell is selected depending on the genetically engineered cell membrane marker molecule. That is, the ligand binds only to the cell membrane marker which is expressed by the cell from the extrachromosomal genetic material so that only the genetically-modified cells bind to the surface of the medical device. For example, if the mammalian cell is an endothelial cell, the ligand can be at least one type of antibody specifically raised against a specific target epitope or marker molecule on the surface of the target cell. In this aspect of the invention, the antibody can be a monoclonal antibody, a polyclonal antibody, a chimeric antibody, or a humanized antibody which recognizes and binds only to the genetically-altered endothelial cell by interacting with the surface marker molecule and, thereby modulating the adherence of the cells onto the surface of the medical device. The antibody or antibody fragment of the invention can be covalently or noncovalently attached to the surface of the matrix, or tethered covalently by a linker molecule to the outermost layer of the matrix coating the medical device. In this embodiment of the invention, for example, the monoclonal antibodies can further comprises Fab or $F(ab')_2$ fragments. The antibody fragment of the invention comprises any fragment size, such as large and small molecules which retain the characteristic to recognize and bind the target antigen as the antibody.

In another embodiment, the antibody or antibody fragment of the invention recognize and bind antigens with specificity for the mammal being treated and their specificity is not dependent on cell lineage. In one embodiment, for example, in treating restenosis wherein the cells may not be genetically modified to contain specific cell membrane marker molecules, the antibody or fragment is specific for selecting and binding circulating progenitor endothelial cell surface antigen such as CD133, CD34, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2 and HAD-DR.

In another embodiment, the coating of the medical device comprises at least one layer of a biocompatible matrix as described above, the matrix comprising an outer surface for attaching a therapeutically effective amount of at least one type of small molecule of natural or synthetic origin. The small molecule recognizes and interacts with, for example, progenitor endothelial cells in the treatment of restenosis, to immobilize the cells on the surface of the device to form an endothelial layer. The small molecules can be used in conjunction with the medical device for the treatment of various diseases, and can be derived from a variety of sources such as cellular components such as fatty acids, proteins, nucleic acids, saccharides and the like and can interact with an antigen on the surface of a progenitor endothelial cell with the same results or effects as an antibody. In this aspect of the invention, the coating on the medical device can further comprise a compound such as a growth factor as described herewith in conjunction with the coating comprising an antibody or antibody fragment.

In one embodiment, the compound of the coating of the invention, for example in treating restenosis, comprises any compound which stimulates or accelerates the growth and differentiation of the progenitor cell into mature, functional endothelial cells. In another embodiment, the compound is for stimulating the genetically modified cells to express and secrete the desired gene product. For example, a compound for use in the invention may be a growth factor such as vascular endothelial growth factor (VEGF), basic fibroblast growth factor, platelet-induced growth factor, transforming growth factor beta 1, acidic fibroblast growth factor, osteonectin, angiopoietin 1 (Ang-1), angiopoietin 2 (Ang-2), insulin-like growth factor, granulocyte-macrophage colony-stimulating factor, platelet-derived growth factor AA, platelet-derived growth factor BB, platelet-derived growth factor AB and endothelial PAS protein 1.

In another embodiment, for example when using genetically-altered mammalian cells, the activating agents or compounds useful for stimulating the cells to express and secrete the genetically-engineered gene products include, but are not limited to estrogen, tetracycline and other antibiotics, tamoxiphen, etc., and can be provided to the patient via various routes of administration, such as through the skin via a patch and subcutaneously.

The invention also provides methods for treating a variety of diseases, such as vascular disease, cancer, blood vessel remodeling, severe coronary artery disease. artherosclerosis, restenosis, thrombosis, aneurysm and blood vessel obstruction. In one embodiment, the method provides an improvement over prior art methods as far as retaining or sealing the medical device insert to the vessel wall, such as a stent or synthetic vascular graft, heart valve, abdominal aortic aneurysm devices and components thereof, for establishing vascular homeostasis, and thereby preventing excessive intimal hyperplasia as in restenosis. In the present method of treating atherosclerosis, the artery may be either a coronary artery or a peripheral artery such as the femoral artery. Veins can also be treated using the techniques and medical device of the invention.

With respect to the treatment of restenosis, the invention also provides an engineered method for inducing a healing response. In one embodiment, a method is provided for rapidly inducing the formation of a confluent layer of endothelium in the luminal surface of an implanted device in a target lesion of an implanted vessel, in which the endothelial cells express nitric oxide synthase and other anti-inflammatory and inflammation-modulating factors. The invention also provides a medical device which has increased biocompatibility over prior art devices, and decreases or inhibits tissue-based excessive intimal hyperplasia and restenosis by decreasing or inhibiting smooth muscle cell migration, smooth muscle cell differentiation, and collagen deposition along the inner luminal surface at the site of implantation of the medical device.

In an embodiment of the invention, a method for coating a medical device comprises the steps of: applying at least one layer of a biocompatible matrix to the surface of the medical device, wherein the biocompatible matrix comprises at least one component selected from the group consisting of a polyurethane, a segmented polyurethane-urea/heparin, a poly-L-lactic acid, a cellulose ester, a polyethylene glycol, a polyvinyl acetate, a dextran, gelatin, collagen, elastin, laminin, fibronectin, vitronectin, heparin, fibrin, cellulose and carbon and fullerene, and applying to the biocompatible matrix, simultaneously or sequentially, a therapeutically effective amounts of at least one type of antibody, antibody fragment or a combination thereof, and at least one compound which stimulates endothelial cell growth and differentiation.

The invention further provides a method for treating vascular disease in a mammal comprises implanting a medical device into a vessel or tubular organ of the mammal, wherein the medical device is coated with (a) a biocompatible matrix, (b) therapeutically effective amounts of at least one type of antibody, antibody fragment or a combination thereof, and (c) at least one compound; wherein the antibody or antibody fragment recognizes and binds an antigen on a progenitor endothelial cell surface so that the progenitor endothelial cell is immobilized on the surface of the matrix, and the compound is for stimulating the immobilized progenitor endothelial cells to form an endothelium on the surface of the medical device.

In one embodiment of the invention, a therapeutic/drug delivery system for treating a disease in a patient is also provided. The therapeutic or drug delivery system comprises genetically-altered mammalian cells, comprising exogenous nucleic acid encoding a genetically-engineered cell membrane marker and at least one therapeutic gene product, and a medical device for implantation into a patient. In one embodiment, the genetic engineered cells are transfected in vitro with an appropriate transfection vector comprising the exogenous genetic material for providing the desired genes to the cells. In this embodiment of the invention the cells can be any mammalian cell, either autologous, allogenic or xenogenic, such as endothelial cells, fibroblasts, myoblasts and the like. In this embodiment of the invention, the medical device is coated with a biocompatible matrix comprising a ligand which binds only to the genetically-altered mammalian cells by way binding the genetically-engineered cell membrane marker on the surface of the cells.

In the therapeutic and/or drug delivery system of this embodiment, the genetically-altered cells are provided with exogenous genetic material to introduce at least one desired gene which encodes a cell surface marker and at least one gene which encodes a therapeutic gene product. The system optionally comprises a signal system, such as an activating compound or molecule for stimulating the genetically-altered mammalian cells to express and/or secrete the desired gene product and/or the marker gene.

Thus, in one embodiment of the invention, the exogenous genetic material for introducing into mammalian cells is engineered to encode a cell membrane marker which specifically binds to the ligand on the device. For example, if the device is for implantation in a blood vessel lumen, the exogenous genetic material encodes a cell membrane marker not found in any cell circulating in the blood stream, other than the genetically-engineered cells provided to the patient.

It is an object of the invention to provide a coated medical devices and methods for the treatment of a variety of diseases such as vascular disease including but not limited to atherosclerosis, cancer, and rheumatoid arthritis. The medical device of the invention comprises a coating for the specific in vivo capturing and immobilization of genetically-altered mammalian cells which are introduced, simultaneously or sequentially, into the patient upon implantation of the coated medical device.

It is an object of the invention to provide the immobilized genetically-altered cells which express and/or secrete at least one type of substance or therapeutic agent for the treatment of a specific disease. In this aspect of the invention, for example in the treatment of cancer, the cells, e.g., endothelial cells are genetically-altered by introducing exogenous genetic material into the cells. In one embodiment, the genetic material is introduced into the nucleus of the cells and is DNA, such as extrachromosomal DNA. The extrachromosomal DNA may be a vector such an adenoviral vector, a plasmid such as a naked plasmid, linear or short DNA, and the like. In one embodiment, the DNA comprises regulatory/expression cassette for controlling the expression of the desired marker and/or therapeutic genes. In one embodiment, the regulatory cassette may comprise regulatory elements for constitutive expression of the therapeutic genes or may comprise elements that can be controlled or expressed as needed by the patient.

In one embodiment, the medical device for implantation into the patient comprises a coating; the coating comprises a matrix bearing at least one type of ligand, which recognizes and binds target cells. In the embodiment where the cells are genetically-altered, the ligand only recognizes a specific cell membrane marker which is engineered into the cells. Thus in this embodiment of the invention, such ligand only recognizes the genetically-altered mammalian cells introduced into the patient, and the genetically-altered mammalian cells bind to said medical device and express and secrete said at least one therapeutic gene product.

In another embodiment, the therapeutic or drug delivery system may further comprise an activating molecule for stimulating said genetically-altered mammalian cells to express and/or secrete the desired therapeutic gene products. In this aspect of the invention, a compound such as a chemical stimulus or a peptide can be provided to the patient via an oral route, a thermal patch, intravenously, intradermally and the like. In this embodiment, the genetically-altered mammalian cells may be autogenic or xenogenic, such as mature endothelial cells, fibroblasts, muscle cells, epithelial cells, etc. exogenous nucleic acid is extrachromosomal DNA. In one embodiment, the DNA is provided in the form of a vector, such as an adenovirus vector, naked plasmid DNA, linear DNA and the like. In one embodiment, the extrachromosomal DNA comprises a regulatory cassette, a gene which encodes a cell membrane antigen and at least one gene which encodes a peptide for treating a disease. In one aspect of the invention, the cell membrane specific gene encodes, for example, an osteogenic or a prostatic cell membrane protein.

In one embodiment of the invention, the extrachromosomal genetic material comprises a gene which encodes the therapeutic/drug product, such as vascular endothelial growth factor and angiogenin for use in blood vessel remodeling, anti-angiogenic factor in the treatment of cancer.

In another embodiment of the invention, a method for treating disease in a patient is provided. The method comprises:

providing genetically-altered mammalian cells to the patient; comprising exogenous nucleic acid encoding a genetically-engineered cell membrane marker and at least one therapeutic gene product;

implanting a medical device comprising a coating into the patient; the coating comprising a matrix bearing at least one ligand, wherein the ligand recognizes and binds the genetically-engineered cell membrane marker on the genetically-altered mammalian cells, and wherein the genetically-altered mammalian cells bind to the medical device and express and secrete the therapeutic gene product. In an embodiment of the invention, the therapeutic gene and gene product comprises, for example, vascular endothelial growth factor, angiogenin, anti-angiogenic factor, fibroblast growth factor.

The invention also provides a method for treating disease in a patient, the method comprises: providing genetically-altered mammalian cells to the patient; implanting a medical device into the patient; wherein the medical device comprises a coating which comprises a matrix bearing at least one ligand, wherein the ligand specifically recognizes and binds at least one receptor on the genetically-altered mammalian cells, and wherein the genetically-altered mammalian cells bind to the medical device and comprise exogenous nucleic acid for expressing and secreting a therapeutic gene product.

In another embodiment, a method for recruiting cells to a blood contacting surface in vivo is provided. The method comprises providing a blood contacting surface positioned in the blood stream of a subject, said blood contacting surface configured to recruit target cells circulating in the blood stream of the subject to the blood contacting surface; and recruiting the target cells to the blood contacting surface. In this embodiment, the blood contacting surface comprises the luminal surface of a medical device implanted into the subject. In this embodiment of the invention, The recruited target cells on the blood contacting surface, for example, a stent or graft, can self-endothelialize the surface of the device in restoring normal endothelium at a site of blood vessel injury. The blood contacting surface can be a biodegradable scaffolding or can be coated with a biodegradable, biocompatible material. In this aspect of the invention, the biodegradable scaffolding when implanted into a blood vessel undergoes in situ degradation and the neo-endothelium formed on the luminal surface of the device restores the blood vessel continuity through the injured site so as to form a functional neo-vessel.

In another embodiment, the invention comprises prosthesis, comprising: (a) a support member having an exterior surface and a blood contacting surface; (b) a first layer of a cross-linked polymeric compound coated onto said blood contacting surface of said support member; and, (c) a second layer coated on said first layer, said second layer comprising at least one ligand having an affinity for a targeted cell in vivo.

In another embodiment, a method for generating a self-endothelializing graft in vivo, the method comprising: (a) providing a scaffolding configured to function as a vascular graft, said scaffolding having a lumen surface and exterior surface, said lumen surface comprising ligands specific for binding to endothelial progenitor cells; (b) implanting said scaffolding into a blood vessel of a subject; and (c) recruiting circulating endothelial progenitor cells to said lumen surface of said scaffolding to form a neo-endothelium.

In yet another embodiment, a method for generating a self-endothelializing graft in situ, the method comprising: (a) providing a prosthetic structure having a surface exposed to circulating blood; (b) implanting the prosthetic structure into a subject; and (c) recruiting circulating endothelial progenitor cells from the blood to the surface of the prosthetic structure to form a neo-endothelium thereon.

In another embodiment, a method for generating a self-endothelializing graft in situ, the method comprising: (a) providing a biodegradable scaffolding configured to function as a temporary vascular graft, the scaffolding having a lumen surface and exterior surface; (b) implanting the biodegradable scaffolding into a blood vessel; (c) recruiting circulating progenitor endothelial cells to the lumen surface of the biodegradable scaffolding to form a neo-endothelium; (d) encapsulating the exterior surface of the scaffolding by vascular tissue to form an exterior hemostatic vascular structure; and (e) degrading the biodegradable scaffolding under in vivo conditions within a time frame which allows the neo-endothelium and the exterior vascular structure to form a functional neo-vessel.

In an embodiment, a biodegradable scaffolding for forming an endothelialized vascular graft in situ, the scaffolding comprising: (a) a porous biodegradable support member having a lumen and an exterior surface; and (b) the lumen surface comprising a first layer of at least one species of a polymeric compound coated to the support member, and wherein the compound is cross-linked to itself with a cross-linking agent that forms covalent bonds that are subject to enzymatic cleavage or non-enzymatic hydrolysis under in vivo conditions.

In another embodiment, a method for generating a self-endothelializing graft in situ, the method comprising: (a) providing a prosthetic structure, having a surface exposed to circulating blood; (b) implanting the prosthetic structure into a subject; and (c) recruiting circulating progenitor endothelial cells from the blood to the surface of the prosthetic structure to form a neo-endothelium.

BRIEF DESCRIPTION OF DRAWINGS

FIG. 1C depicts a schematic representation of a stent coated with the matrix of the invention showing how cells interact with ligands on the surface of a device.

FIG. 2A is a phase contrast micrograph of progenitor endothelial cells adhered to a fibronectin-coated slide containing cells isolated by enriched medium. FIG. 2B is a phase contrast micrograph of progenitor endothelial cells adhered to a fibronectin-coated slide containing cells isolated by anti-CD34 antibody coated magnetic beads. FIGS. 2D and 2F are micrographs of the progenitor endothelial cells which had been incubated for 7 days and stained with PI nuclear stain. As seen in these figures, the cells express mature endothelial cell markers as shown by the antibody fluorescence for Tie-2 (FIGS. 2E and 2G) and VEGFR-2 (FIG. 2C) antibody reactivity.

FIGS. 3A and 3B are photographs of a 2% agarose gel stained with ethidium bromide of a semiquantitative RT-PCR for endothelial nitric oxide synthatase, eNOS and glyceraldehyde phosphate dehydrogenase, GAPDH. After 3 days (FIG. 3B) and 7 days (FIG. 3A) in culture on fibronectin-coated slides, the progenitor endothelial cells begin to express eNOS mRNA.

FIGS. 5A-5C are photomicrographs of a control, coated with CMDx without antibody which were incubated with the white cell fraction of human blood. The cells were stained with propidium iodide and FITC labeled anti-KDR antibody. FIGS. 5D-5F are photomicrographs of control stainless steel discs coated with gelatin without antibody bound to its surface which were incubated with the white cell fraction of human blood. The cells were stained with propidium iodide and FITC labeled anti-KDR antibody.

FIGS. 6A-6C are photomicrographs of stainless steel discs coated with CMDx matrix with anti-CD34 antibody bound to its surface which were incubated with the HUVECs. The cells were stained with propidium iodide and FITC labeled anti-KDR antibody. FIGS. 6D-6F are photomicrographs of stainless steel discs coated with gelatin matrix with antibody bound to its surface, which were incubated with HUVECS. The cells were stained with propidium iodide and FITC labeled anti-KDR antibody.

FIGS. 8A and 8B are photomicrographs of a stainless steel disc coated with CMDx matrix containing anti-CD34 antibody bound to its surface incubated with progenitor cells for 7 days. The cells were stained with propidium iodide and FITC labeled anti-KDR antibody.

FIGS. 9A and 9B photomicrograph of a stainless steel disc coated with CMDx matrix containing anti-CD34 antibody bound to its surface incubated with progenitor cells for 7 days. The cells were stained with propidium iodide and FITC labeled anti-Tie-2 antibody.

FIGS. 10A-10C are phase contrast photomicrographs of stainless steel CMDx coated discs incubated with progenitor cells for 3 weeks in endothelial growth medium which show mature endothelial cells.

FIGS. 12A-12D are photomicrographs of fullerene-coated samples without or with anti-CD34 antibody. The samples were incubated with a human white blood cell fraction and stained with Propidium iodide and FITC labeled anti-VEGFR-2 antibody.

FIGS. 13A-13D are photomicrographs of histological cross-sections of coronary artery explants which had been implanted for 4 weeks with a bare stainless steel stent (FIGS. 13A and 13C) and a fullerene-coated sample (FIGS. 13B and 13D) taken at low and high magnification. The sections were stained with hematoxylin-eosin stain.

FIGS. 14A-14G are scanning electron micrographs of stent explants 1 and 48 hours after implantation in male Yorkshire swine. Explants of dextran-coated (FIG. 14A) and dextran/anti-CD34 antibody-coated (14B) stents at 1 hour after implantation. FIGS. 14C and 14D show explants of control samples and FIGS. 14E-G are dextran/anti-CD34 antibody-coated stents at 48 hours after implantation.

FIGS. 15A, 15B and 15C are, respectively, fluorescent photomicrographs of 48 hours explants of a dextran-plasma-coated stent without antibody on its surface, and a dextran-plasma-coated/anti-CD34 antibody-coated stent of 18 mm in length.

DETAILED DESCRIPTION

Figure 1A:
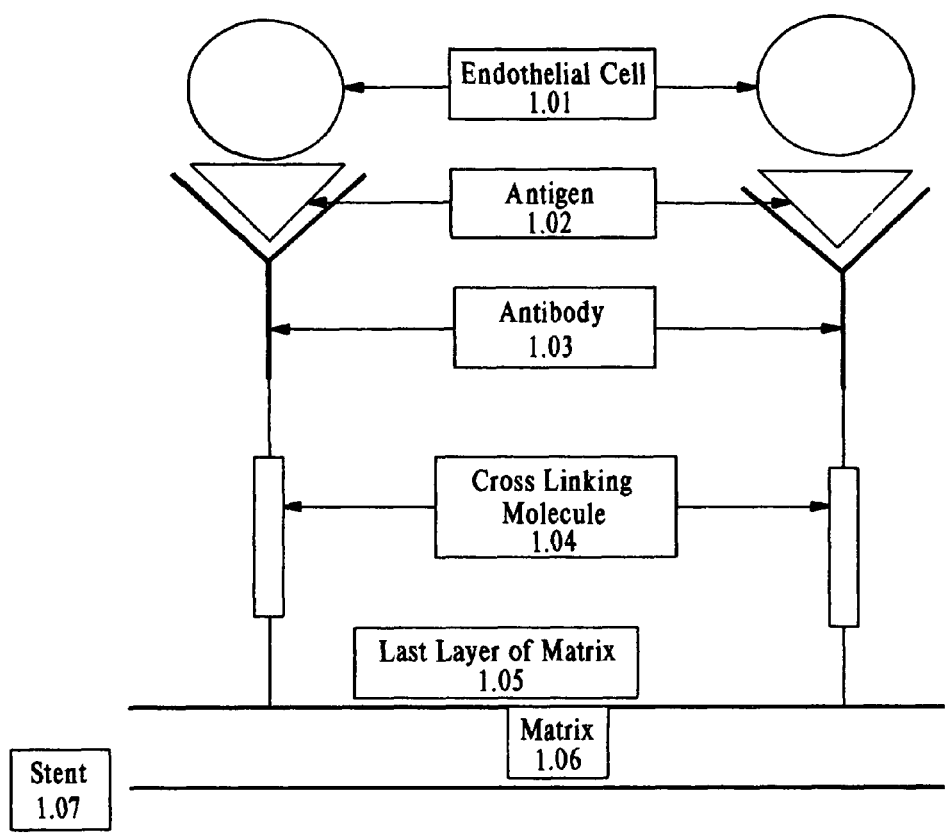
FIG. 1A is a schematic representation of an antibody tethered covalently to the matrix by a cross-linking molecule.
Figure 1B:
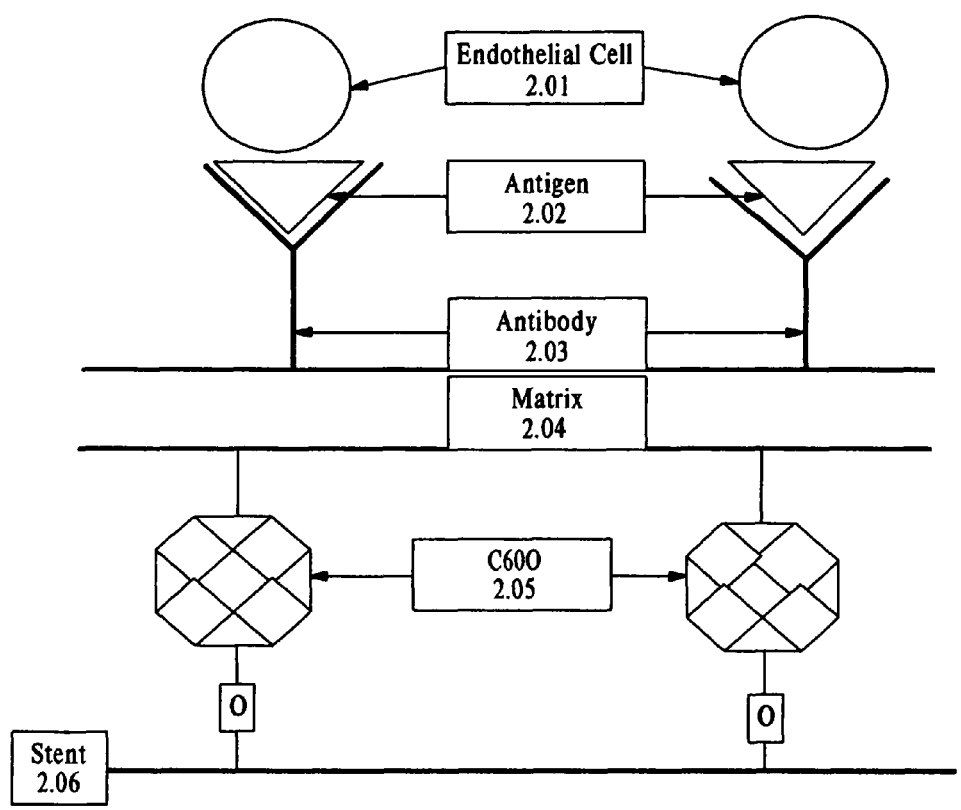
FIG. 1B shows a diagram of the $C_{60}O$ molecule anchoring the matrix.

The present invention provides a coated, implantable medical device such as a stent, methods and compositions for coating the medical device, and methods of treating vascular disease with the coated medical device. FIGS. 1A-1C show a schematic representation of the surface coat of a medical device of the invention. The coat on the medical device comprises a biocompatible matrix for promoting the formation of a confluent layer of endothelial cells on the surface of the device to inhibit excessive intimal hyperplasia, and thereby preventing restenosis and thrombosis. In one embodiment, the matrix comprises a synthetic or naturally-occurring material in which a therapeutically effective amount of at least one type of antibody that promotes adherence of endothelial, progenitor or stem cells to the medical device, and at least one compound such as a growth factor, which stimulates endothelial cell growth and differentiation. Upon implantation of the device, the cells that adhere to the surface of the device transform into a mature, confluent, functional layer of endothelium on the luminal surface of the medical device. The presence of a confluent layer of endothelial cells on the medical device reduces the occurrence of restenosis and thrombosis at the site of implantation.

As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen of an organ, such as an artery, vein, ventricle, or atrium of the heart. Medical devices may include stents, stent grafts, covered stents such as those covered with polytetrafluoroethylene (PTFE), expanded polytetrafluoroethylene (ePTFE), or other natural or synthetic coverings, or synthetic vascular grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., cross-linked PVA hydrogel), vascular sutures, vascular anastomosis fixtures, transmyocardial revascularization stents and/or other conduits.

Coating of the medical device with the compositions and methods of this invention stimulates the development of a confluent mammalian cell layer such as an endothelial cell layer on the surface of the medical device, thereby preventing restenosis as well as modulating the local chronic inflammatory response and thromboembolic complications that result from implantation of the medical device.

The matrix coating the medical device can be composed of synthetic material, such as polymeric gel foams, such as hydrogels made from polyvinyl alcohol (PVA), polyurethane, poly-L-lactic acid, cellulose ester or polyethylene glycol. In one embodiment, very hydrophilic compounds such as dextran compounds can comprise the synthetic material for making the matrix. In another embodiment, the matrix is composed of naturally occurring materials, such as collagen, fibrin, elastin, or amorphous carbon. The matrix may comprise several layers with a first layer being composed of synthetic or naturally occurring materials and a second layer composed of antibodies. The layers may be ordered sequentially, with the first layer directly in contact with the stent or synthetic graft surface and the second layer having one surface in contact with the first layer and the opposite surface in contact with the vessel lumen.

The matrix further comprises at least a growth factor, cytokine or the like, which stimulates endothelial cell proliferation and differentiation. For example, vascular endothelial cell growth factor (VEGF) and isoforms, basic fibroblast growth factor (bFGF), platelet-induced growth factor (PlGF), transforming growth factor beta 1 (TGF. b1), acidic fibroblast growth factor (aFGF), osteonectin, angiopoietin 1, angiopoietin 2, insulin-like growth factor (ILGF), platelet-derived growth factor AA (PDGF-AA), platelet-derived growth factor BB (PDGF-BB), platelet-derived growth factor AB (PDGF-AB), granulocyte-macrophage colony-stimulating factor (GM-CSF), and the like, or functional fragments thereof can be used in the invention.

In another embodiment, the matrix may comprise fullerenes, where the fullerenes range from about $C_{20}$ to about $C_{150}$ in carbon number. The fullerenes can also be arranged as nanotubes, that incorporate molecules or proteins. The fullerene matrix can also be applied to the surface of stainless steel, PTFE, or ePTFE medical devices, which layer is then functionalized and coated with antibodies and growth factor on its surface. Alternatively, the PTFE or ePTFE can be layered first on, for example, a stainless steel medical device followed by a second layer of fullerenes and then the antibodies and the growth factor are added.

The matrix may be noncovalently or covalently attached to the medical device. Antibodies and growth factors can be covalently attached to the matrix using hetero- or homobifunctional cross-linking reagents. The growth factor can be added to the matrix using standard techniques with the antibodies or after antibody binding.

As used herein, the term "antibody" refers to one type of monoclonal, polyclonal, humanized, or chimeric antibody or a combination thereof, wherein the monoclonal, polyclonal, humanized or chimeric antibody binds to one antigen or a functional equivalent of that antigen. The term antibody fragment encompasses any fragment of an antibody such as Fab, $F(ab')_2$, and can be of any size, i.e., large or small molecules, which have the same results or effects as the antibody. (An antibody encompasses a plurality of individual antibody molecules equal to $6.022 \times 10^{23}$ molecules per mole of antibody).

In an aspect of the invention, a stent or synthetic graft of the invention is coated with a biocompatible matrix comprising antibodies that modulate adherence of circulating progenitor endothelial cells to the medical device. The antibodies of the invention recognize and bind the target mammalian cells such as therapeutic cells or progenitor endothelial cells by their specific surface antigens which cells are circulating in the blood stream so that the cells are immobilized on the surface of the device. In one embodiment, for example, the antibodies comprise monoclonal antibodies reactive (recognize and bind) with progenitor endothelial cell surface antigens, or a progenitor or stem cell surface antigen, such as vascular endothelial growth factor receptor-1, -2 and -3 (VEGFR-1, VEGFR-2 and VEGFR-3 and VEGFR receptor family isoforms), Tie-1, Tie2, CD34, Thy-1, Thy-2, Muc-18 (CD146), CD30, stem cell antigen-1 (Sca-1), stem cell factor (SCF or c-Kit ligand), CD133 antigen, VE-cadherin, P1H12, TEK, CD31, Ang-1, Ang-2, or an antigen expressed on the surface of progenitor endothelial cells.

In one embodiment, a single type of antibody that reacts with one antigen can be used as the ligand for binding the target cells. Alternatively, a plurality of different antibodies directed against various surface antigens can be mixed together and added to the matrix. In another embodiment, a cocktail of monoclonal antibodies is used to increase the rate of a cell monolayer, such as endothelium formation, by targeting specific cell surface antigens. In this aspect of the invention, for example, anti-CD34 and anti-CD133 are used in combination and attached to the surface of the matrix on a stent.

As used herein, a "therapeutically effective amount of the antibody" means the amount of an antibody that promotes adherence of endothelial, progenitor or stem cells to the medical device. The amount of an antibody needed to practice the invention varies with the nature of the antibody used. For example, the amount of an antibody used depends on the binding constant between the antibody and the antigen against which it reacts. It is well known to those of ordinary skill in the art how to determine therapeutically effective amounts of an antibody to use with a particular antigen.

As used herein, the term "compound" refers to any substance which stimulates cells such as genetically-altered mammalian cells to express and/or secrete the therapeutic gene product.

As used herein, the term "growth factor" refers to a peptide, protein, glycoprotein, lipoprotein, or a fragment or modification thereof, or a synthetic molecule, which stimulates endothelial, stem or progenitor cells to grow and differentiate into mature, functional endothelial cells. Mature endothelial cells express nitric oxide synthetase, thereby releasing nitric oxide into the tissues. Table 1 below lists some of the growth factors that can be used for coating the medical device.

TABLE 1

| Growth Factor | Endothelial cell specific |
| --- | --- |
| Acidic fibroblast growth factor (aFGF) | No |
| Basic fibroblast growth factor (bFGF) | No |
| Fibroblast growth factor 3 (FGF-3) | No |
| Fibroblast growth factor 4 (FGF-4) | No |
| Fibroblast growth factor 5 (FGF-5) | No |
| Fibroblast growth factor 6 (FGF-6) | No |
| Fibroblast growth factor 7 (FGF-7) | No |
| Fibroblast growth factor 8 (FGF-8) | No |
| Fibroblast growth factor 9 (FGF-9) | No |
| Angiogenin 1 | Yes |
| Angiogenin 2 | Yes |
| Hepatocyte growth factor/scatter factor (HGF/SF) | No |
| Platelet-derived growth factor (PDE-CGF) | Yes |
| Transforming growth factor-α (TGF-α) | No |
| Transforming growth factor-β (TGF-β) | No |
| Tumor necrosis factor-α (TNF-α) | No |
| Vascular endothelial growth factor 121 (VEGF 121) | Yes |
| Vascular endothelial growth factor 145 (VEGF 145) | Yes |
| Vascular endothelial growth factor 165 (VEGF 165) | Yes |
| Vascular endothelial growth factor 189 (VEGF 189) | Yes |
| Vascular endothelial growth factor 206 (VEGF 206) | Yes |
| Vascular endothelial growth factor B (VEGF-B) | Yes |
| Vascular endothelial growth factor C (VEGF-C) | Yes |
| Vascular endothelial growth factor D (VEGF-D) | Yes |
| Vascular endothelial growth factor E (VEGF-E) | Yes |
| Vascular endothelial growth factor F (VEGF-F) | Yes |
| Placental growth factor | Yes |
| Angiopoietin-1 | No |
| Angiopoietin-2 | No |
| Thrombospondin (TSP) | No |
| Proliferin | Yes |
| Ephrin-A1 (B61) | Yes |
| E-selectin | Yes |
| Chicken chemotactic and angiogenic factor (cCAF) | No |
| Leptin | Yes |
| Heparin affinity regulatory peptide (HARP) | No |
| Heparin | No |
| Granulocyte colony stimulating factor | No |
| Insulin-like growth factor | No |
| Interleukin 8 | No |
| Thyroxine | No |
| Sphingosine 1-phosphate | No |

As used herein, the term "VEGF" means any of the isoforms of the vascular endothelium growth factor listed in Table 1 above unless the isoform is specifically identified with its numerical or alphabetical abbreviation.

As used herein, the term "therapeutically effective amounts of growth factor" means the amount of a growth factor that stimulates or induces endothelial, progenitor or stem cells to grow and differentiate, thereby forming a confluent layer of mature and functional endothelial cells on the luminal surface of the medical device. The amount of a growth factor needed to practice the invention varies with the nature of the growth factor used and binding kinetics between the growth factor and its receptor. For example, 100 μg of VEGF has been shown to stimulate the adherence of endothelial cells on a medical device and form a confluent layer of epithelium. It is well known to those of ordinary skill in the art how to determine therapeutically effective amounts of a growth factor to use to stimulate cell growth and differentiation of endothelial cells.

As used herein, "intimal hyperplasia" is the undesirable increased in smooth muscle cell proliferation and/or matrix deposition in the vessel wall. As used herein "restenosis" refers to the recurrent narrowing of the blood vessel lumen. Vessels may become obstructed because of restenosis. After PTCA or PTA, smooth muscle cells from the media and adventitia, which are not normally present in the intima, proliferate and migrate to the intima and secrete proteins, forming an accumulation of smooth muscle cells and matrix protein within the intima. This accumulation causes a narrowing of the lumen of the artery, reducing blood flow distal to the narrowing. As used herein, "inhibition of restenosis" refers to the inhibition of migration and proliferation of smooth muscle cells accompanied by prevention of protein secretion so as to prevent restenosis and the complications arising therefrom.

The subjects that can be treated using the medical device, methods and compositions of this invention are mammals, or more specifically, a human, dog, cat, pig, rodent or monkey.

The methods of the present invention may be practiced in vivo or in vitro.

The term "progenitor endothelial cell" refers to endothelial cells at any developmental stage, from progenitor or stem cells to mature, functional endothelial cells from bone marrow, blood or local tissue origin and which are non-malignant.

For in vitro studies or use of the coated medical device, fully differentiated endothelial cells may be isolated from an artery or vein such as a human umbilical vein, while progenitor endothelial cells are isolated from peripheral blood or bone marrow. The endothelial cells are bound to the medical devices by incubation of the endothelial cells with a medical device coated with the matrix that incorporates an antibody, a growth factor, or other agent that adheres to endothelial cells. In another embodiment, the endothelial cells can be transformed endothelial cells. The transfected endothelial cells contain vectors which express growth factors or proteins which directly or indirectly inhibit thrombogenesis, restenosis, or any other therapeutic end.

In another embodiment, endothelial or any other type of stable mammalian cells are transfected with any mammalian expression vector that contains any cloned genes encoding proteins or peptides suitable for specific applications. For example, the vector can be constructed consisting an expression cassette comprising a gene encoding platelet derived growth factor (PDGF), fibroblast growth factor (FGF), or nitric oxide synthase (NOS) and the expression cassette can be constructed using conventional methods, and supplies from commercially available sources. (See, for example, mammalian expression vectors and transfection kits commercially available from Stratagene, San Diego, Calif.). For example, purified porcine progenitor endothelial cells are transfected with vascular endothelial growth factor (VEGF) using an adenoviral expression vector expressing the VEGF cDNA according to the methods of Rosengart et al. (Six-month assessment of a phase I trial of angiogenic gene therapy for the treatment of coronary artery disease using direct intramyocardial administration of an adenovirus vector expressing the VEGF121 cDNA. Ann. Surg. 230(4):466-470, 1999, incorporated herein by reference). In this embodiment of the invention, the mammalian cells can be autologous, allogenic or xenogenic in origin. Once the cells are genetically-altered by transfection of exogenous DNA or RNA expression cassettes comprising the desired genes, the cells can be grown using standard tissue culture techniques. Samples of cells which express and secrete desired genes can be stored frozen in liquid nitrogen using standard techniques. Frozen are regrown using standard tissue culture techniques prior to use. The genetically-altered cells are administered to the patient at the time of implantation of the device either locally at the implant site, or intravenously or intra-arterially into the patient, preferably after the coated medical device is implanted. Transformed cells for use in the invention can further comprise a marker or reporter gene for the accurate detection and identification of the cells prior to cell administration to the patient.

The methods of treatment of vascular disease of the invention can be practiced on any artery or vein. Included within the scope of this invention is atherosclerosis of any artery including coronary, infrainguinal, aortoiliac, subclavian, mesenteric and renal arteries. Other types of vessel obstructions, such as those resulting from a dissecting aneurysm are also encompassed by the invention.

The method of treating a mammal with vascular disease comprises implanting a coated medical device into the patient's organ or vessel, for example, in the case of a coated stent during angioplasty. Once in situ, progenitor endothelial cells are captured on the surface of the coated stent by the recognition and binding of antigens on the progenitor cell surface by the antibody present on the coating. Once the progenitor cell is adhered to the matrix, the growth factor on the coating promotes the newly-bound progenitor endothelial cells to grow and differentiate and form a confluent, mature and functional endothelium on the luminal surface of the stent. Alternatively, the medical device is coated with the endothelial cells in vitro before implantation of the medical device using progenitor, stem cells, or mature endothelial cells isolated from the patient's blood, bone marrow, or blood vessel. In either case, the presence of endothelial cells on the luminal surface of the medical device inhibits or prevents excessive intimal hyperplasia and thrombosis.

Endothelial Cells

Human umbilical vein endothelial cells (HUVEC) are obtained from umbilical cords according to the methods of Jaffe, et al., *J. Clin. Invest.*, 52:2745-2757, 1973, incorporated herein by reference and were used in the experiments. Briefly, cells are stripped from the blood vessel walls by treatment with collagenase and cultured in gelatin-coated tissue culture flasks in M199 medium containing 10% low endotoxin fetal calf serum, 90 ug/ml preservative-free porcine heparin, 20 ug/ml endothelial cell growth supplement (ECGS) and glutamine.

Progenitor endothelial cells (EPC) are isolated from human peripheral blood according to the methods of Asahara et al. (Isolation of putative progenitor endothelial cells for angiogenesis. *Science* 275:964-967, 1997, incorporated herein by reference). Magnetic beads coated with antibody to CD34 are incubated with fractionated human peripheral blood. After incubation, bound cells are eluted and can be cultured in EBM-2 culture medium. (Clonetics, San Diego, Calif.). Alternatively enriched medium isolation can be used to isolate these cells. Briefly, peripheral venous blood is taken from volunteers and the mononuclear cell fraction is isolated by density gradient centrifugation, and the cells are plated on fibronectin coated culture slides (Becton Dickinson) in EC basal medium-2 (EBM-2) (Clonetics) supplemented with 5% fetal bovine serum, human VEGF-A, human fibroblast growth factor-2, human epidermal growth factor, insulin-like growth factor-1, and ascorbic acid. EPCs are grown for 7-days, with culture media changes every 48 hours. Cells are characterized by fluorescent antibodies to CD45, CD34, CD31, VEGFR-2, Tie-2, and E-selectin.

In another embodiment, mammalian cells are transfected with any expression cassette that contains any cloned gene that encodes proteins such as platelet derived growth factor (PDGF), fibroblast growth factor (FGF), or nitric oxide synthase (NOS) using conventional methods. (See, for example, mammalian expression vectors and transfection kits commercially available from Stratagene, San Diego, Calif.). For example, purified porcine progenitor endothelial cells are transfected with vascular endothelial growth factor (VEGF) using an mammalian expression cassette expressing the VEGF cDNA according to the methods of Rosengart et al. (Six-month assessment of a phase I trial of angiogenic gene therapy for the treatment of coronary artery disease using direct intramyocardial administration of an adenovirus vector expressing the VEGF121 cDNA. *Ann. Surg.* 230(4): 466-470 (1999), incorporated herein by reference).

Antibodies

Monoclonal antibodies useful in the method of the invention may be produced according to the standard techniques of Kohler and Milstein (Continuous cultures of fused cells secreting antibody of predefined specificity. *Nature* 265: 495-497, 1975, incorporated herein by reference), or can be obtained from commercial sources. Endothelial cells can be used as the immunogen to produce monoclonal antibodies directed against endothelial cell surface antigens.

Monoclonal antibodies directed against endothelial cells are prepared by injecting HUVEC or purified progenitor endothelial cells into a mouse or rat. After a sufficient time, the mouse is sacrificed and spleen cells are obtained. The spleen cells are immortalized by fusing them with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity, i.e., reactivity with endothelial cell antigens.

Various techniques exist for enhancing yields of monoclonal antibodies such as injection of the hybridoma cells into the peritoneal cavity of a mammalian host which accepts the cells and then harvesting the ascitic fluid. Where an insufficient amount of monoclonal antibody collects in the ascitic fluid, the antibody is harvested from the blood of the host. Various conventional ways exist for isolation and purification of monoclonal antibodies so as to free the monoclonal antibodies from other proteins and other contaminants.

Also included within the scope of the invention are useful binding fragments of anti-endothelial cell monoclonal antibodies such as the Fab, $F(ab')_2$ of these monoclonal antibodies. The antibody fragments are obtained by conventional techniques. For example, useful binding fragments may be prepared by peptidase digestion of the antibody using papain or pepsin.

Antibodies of the invention are directed to an antibody of the IgG class from a murine source; however, this is not meant to be a limitation. The above antibody and those antibodies having functional equivalency with the above antibody, whether from a murine source, mammalian source including human, or other sources, or combinations thereof are included within the scope of this invention, as well as other classes such as IgM, IgA, IgE, and the like, including isotypes within such classes. In the case of antibodies, the term "functional equivalency" means that two different antibodies each bind to the same antigenic site on an antigen, in other words, the antibodies compete for binding to the same antigen. The antigen may be on the same or different molecule.

In one embodiment, monoclonal antibodies reacting with the endothelial cell surface antigen CD34 are used. Anti-CD34 monoclonal antibodies attached to a solid support have been shown to capture progenitor endothelial cells from human peripheral blood. After capture, these progenitor cells are capable of differentiating into endothelial cells. (Asahara et al. 1997. Isolation of putative progenitor endothelial cells for angiogenesis. *Science* 275:964-967.) Hybridomas producing monoclonal antibodies directed against CD34 can be obtained from the American Type Tissue Collection. (Rockville, Md.). In another embodiment, monoclonal antibodies reactive with endothelial cell surface antigens such as VEGFR-1 and VEGFR-2, CD133, or Tie-2 are used. In the embodiment using genetically-altered cell, antibodies are produced against the genetically engineered gene product using standard techniques in the same manner as described above, and then applied to the blood contacting surface of the medical device following matrix application.

Polyclonal antibodies reactive against endothelial cells isolated from the same species as the one receiving the medical device implant may also be used.

Stent

The term "stent" herein means any medical device which when inserted or implanted into the lumen of a vessel expands the cross-sectional lumen of a vessel. The term "stent" includes, stents commercially available manufactured from stainless steel or other alloys which have been coated by the methods of the invention; covered stents such as those covered with PTFE or ePTFE. In one embodiment, this includes stents delivered percutaneously to treat coronary artery occlusions or to seal dissections or aneurysms of the splenic, carotid, iliac and popliteal vessels. In another embodiment, the stent is delivered into a venous vessel. The stent can be composed of polymeric or metallic structural elements onto which the matrix comprising the antibodies and the compound, such as growth factors, is applied or the stent can be a composite of the matrix intermixed with a polymer. For example, a deformable metal wire stent can be used, such as that disclosed in U.S. Pat. No. 4,886,062 to Wiktor, incorporated herein by reference. A self-expanding stent of resilient polymeric material such as that disclosed in published international patent application WO91/12779 "Intraluminal Drug Eluting Prosthesis", incorporated herein by reference, can also be used. Stents may also be manufactured using stainless steel, polymers, nickel-titanium, tantalum, gold, platinum-iridium, cobalt-based alloys or Elgiloy and MP35N and other ferrous materials. Stents are delivered through the body lumen on a catheter to the treatment site where the stent is released from the catheter, allowing the stent to expand into direct contact with the luminal wall of the vessel. In another embodiment, the stent comprises a biodegradable stent (H. Tamai, pp 297 in Handbook of Coronary Stents, 3rd Edition, Eds. P W Serruys and M J B Kutryk, Martin Dunitz (2000). It will be apparent to those skilled in the art that other self-expanding stent designs (such as resilient metal stent designs) could be used with the antibodies, growth factors and matrices of this invention.

Synthetic Graft

The term "synthetic graft" means any artificial prosthesis having biocompatible characteristics. In one embodiment, the synthetic grafts can be made of polyethylene terephthalate (Dacron®, PET) or polytetrafluoroehtylene (Teflon®, ePTFE). In another embodiment, synthetic grafts are composed of polyurethane, cross-linked PVA hydrogel, and/or biocompatible foams of hydrogels. In yet a third embodiment, a synthetic graft is composed of an inner layer of meshed polycarbonate urethane and an outer layer of meshed polyethylene terephthalate. It will be apparent to those skilled in the art that any biocompatible synthetic graft can be used with the antibodies, growth factors, and matrices of this invention. (Bos et al. 1998. Small-Diameter Vascular Prostheses: Current Status. *Archives Physio Biochem.* 106: 100-115, incorporated herein by reference). Synthetic grafts can be used for end-to-end, end to side, side to end, side to side or intraluminal and in anastomosis of vessels or for bypass of a diseased vessel segments, for example, as abdominal aortic aneurysm devices.

Matrix (A) Synthetic Materials—

The matrix that is used to coat the stent or synthetic graft may be selected from synthetic materials such as polyurethane, segmented polyurethane-urea/heparin, poly-L-lactic acid, cellulose ester, polyethylene glycol, cross-linked PVA hydrogel, biocompatible foams of hydrogels, or hydrophilic dextrans, such as carboxymethyl dextran.

(B) Naturally Occurring Material—

The matrix may be selected from naturally occurring substances such as collagen, fibronectin, vitronectin, elastin, laminin, heparin, fibrin, cellulose or carbon. A primary requirement for the matrix is that it be sufficiently elastic and flexible to remain unruptured on the exposed surfaces of the stent or synthetic graft.

(C) Fullerenes—

The matrix may also comprise a fullerene (the term "fullerene" encompasses a plurality of fullerene molecules). Fullerenes are carbon-cage molecules. The number of carbon (C) molecules in a fullerene species varies from about $C_{20}$ to about $C_{150}$. Fullerenes are produced by high temperature reactions of elemental carbon or of carbon-containing species by processes well known to those skilled in the art; for example, by laser vaporization of carbon, heating carbon in an electric arc or burning of hydrocarbons in sooting flames. (U.S. Pat. No. 5,292,813, to Patel et al., incorporated herein by reference; U.S. Pat. No. 5,558,903 to Bhushan et al., incorporated herein by reference). In each case, a carbonaceous deposit or soot is produced. From this soot, various fullerenes are obtained by extraction with appropriate solvents, such as toluene. The fullerenes are separated by known methods, in particular by high performance liquid chromatography (HPLC). Fullerenes may be synthesized or obtained commercially from Dynamic Enterprises, Ltd., Berkshire, England or Southern Chemical Group, LLC, Tucker, Ga., or Bucky USA, Houston Tex.

Fullerenes may be deposited on surfaces in a variety of different ways, including, sublimation, laser vaporization, sputtering, ion beam, spray coating, dip coating, roll-on brush coating as disclosed in U.S. Pat. No. 5,558,903, or by derivatization of the surface of the stent.

An important feature of fullerenes is their ability to form "activated carbon." The fullerene electronic structure is a system of overlapping pi-orbitals, such that a multitude of bonding electrons are cooperatively presented around the surface of the molecule. (*Chemical and Engineering News*, Apr. 8, 1991, page 59, incorporated herein by reference). As forms of activated carbon, fullerenes exhibit substantial van der Waals forces for weak interactions. The adsorptive nature of the fullerene surface may lend itself to additional modifications for the purpose of directing specific cell membrane interactions. For example, specific molecules that possess chemical properties that selectively bind to cell membranes of particular cell types or to particular components of cell membranes, e.g., lectins or antibodies, can be adsorbed to the fullerene surface. Attachment of different molecules to the fullerene surface may be manipulated to create surfaces that selectively bind various cell types, e.g., progenitor endothelial cells, epithelial cells, fibroblasts, primary explants, or T-cell subpopulations. U.S. Pat. No. 5,310,669 to Richmond et al., incorporated herein by reference; Stephen R. Wilson, Biological Aspects of Fullerenes, *Fullerenes:Chemistry, Physics and Technology*, Kadish et al. eds., John Wiley & Sons, New York 2000, incorporated herein by reference.

Fullerenes may also form nanotubes that incorporate other atoms or molecules. (Liu et al. Science 280:1253-1256 (1998), incorporated herein by reference). The synthesis and preparation of carbon nanotubes is well known in the art. (U.S. Pat. No. 5,753,088 to Olk et al., and U.S. Pat. No. 5,641,466 to Ebbsen et al., both incorporated herein by reference). Molecules such as proteins can also be incorporated inside carbon nanotubes. For example, nanotubes may be filled with the enzymes, e.g., $Zn_2Cd_2$-metallothionein, cytochromes C and C3, and beta-lactamase after cutting the ends of the nanotube. (Davis et al. *Inorganica Chim. Acta* 272:261 (1998); Cook et al. *Full Sci. Tech.* 5(4):695 (1997), both incorporated herein by reference).

Three dimensional fullerene structures can also be used. U.S. Pat. No. 5,338,571 to Mirkin et al., incorporated herein by reference, discloses three-dimensional, multilayer fullerene structures that are formed on a substrate surface by (i) chemically modifying fullerenes to provide a bond-forming species; (ii) chemically treating a surface of the substrate to provide a bond-forming species effective to covalently bond with the bond-forming species of the fullerenes in solution; and, (iii) contacting a solution of modified fullerenes with the treated substrate surface to form a fullerene layer covalently bonded to the treated substrate surface.

(D) Application of the Matrix to the Medical Device

The matrix should adhere tightly to the surface of the stent or synthetic graft. Preferably, this is accomplished by applying the matrix in successive thin layers. Alternatively, antibodies and growth factors are applied only to the surface of the outer layer in direct contact with the vessel lumen. Different types of matrices may be applied successively in succeeding layers. The antibodies may be covalently or noncovalently coated on the matrix after application of the matrix to the stent.

In order to coat a medical device such as a stent, the stent is dipped or sprayed with a liquid solution of the matrix of moderate viscosity. After each layer is applied, the stent is dried before application of the next layer. In one embodiment, a thin, paint-like matrix coating does not exceed an overall thickness of 100 microns.

In one embodiment, the stent surface is first functionalized, followed by the addition of a matrix layer. Thereafter, the antibodies and the growth factor are coupled to the surface of the matrix. In this aspect of the invention, the techniques of the stent surface creates chemical groups which are functional. The chemical groups such as amines, are then used to immobilize an intermediate layer of matrix, which serves as support for the antibodies and the growth factor.

In another embodiment, a suitable matrix coating solution is prepared by dissolving 480 milligrams (mg) of a drug carrier, such as poly-D, L-lactid (available as R203 of Boehringer Inc., Ingelheim, Germany) in 3 milliliters (ml) of chloroform under aseptic conditions. In principle, however, any biodegradable (or non-biodegradable) matrix that is blood- and tissue-compatible (biocompatible) and can be dissolved, dispersed or emulsified may be used as the matrix if, after application, it undergoes relatively rapid drying to a self-adhesive lacquer- or paint-like coating on the medical device.

For example, coating a stent with fibrin is well known to one of ordinary skill in the art. In U.S. Pat. No. 4,548,736 issued to Muller et al., incorporated herein by reference, fibrin is clotted by contacting fibrinogen with thrombin. Preferably, the fibrin in the fibrin-containing stent of the present invention has Factor XIII and calcium present during clotting, as described in U.S. Pat. No. 3,523,807 issued to Gerendas, incorporated herein by reference, or as described in published European Pat. Application 0366564, incorporated herein by reference, in order to improve the mechanical properties and biostability of the implanted device. Preferably, the fibrinogen and thrombin used to make fibrin in the present invention are from the same animal or human species as that in which the stent will be implanted in order to avoid any inter-species immune reactions, e.g., human anti-cow. The fibrin product can be in the form of a fine, fibrin film produced by casting the combined fibrinogen and thrombin in a film and then removing moisture from the film osmotically through a semipermeable membrane. In the European Pat. Application 0366564, a substrate (preferably having high porosity or high affinity for either thrombin or fibrinogen) is contacted with a fibrinogen solution and with a thrombin solution. The result is a fibrin layer formed by polymerization of fibrinogen on the surface of the medical device. Multiple layers of fibrin applied by this method could provide a fibrin layer of any desired thickness. Alternatively, the fibrin can first be clotted and then ground into a powder which is mixed with water and stamped into a desired shape in a heated mold (U.S. Pat. No. 3,523,807). Increased stability can also be achieved in the shaped fibrin by contacting the fibrin with a fixing agent such as glutaraldehyde or formaldehyde. These and other methods known by those skilled in the art for making and forming fibrin may be used in the present invention.

If a synthetic graft is coated with collagen, the methods for preparing collagen and forming it on synthetic graft devices are well known as set forth in U.S. Pat. No. 5,851,230 to Weadock et al., incorporated herein by reference. This patent describes methods for coating a synthetic graft with collagen. Methods for adhering collagen to a porous graft substrate typically include applying a collagen dispersion to the substrate, allowing it to dry and repeating the process. Collagen dispersions are typically made by blending insoluble collagen (approximately 1-2% by weight) in a dispersion at acidic pH (a pH in a range of 2 to 4). The dispersion is typically injected via syringe into the lumen of a graft and massaged manually to cover the entire inner surface area with the collagen slurry. Excess collagen slurry is removed through one of the open ends of the graft. Coating and drying steps are repeated several times to provide sufficient treatment.

In yet another embodiment, the stent or synthetic graft is coated with amorphous carbon. In U.S. Pat. No. 5,198,263, incorporated herein by reference, a method for producing a high-rate, low-temperature deposition of amorphous carbon films in the presence of a fluorinated or other halide gas is described. Deposition according to the methods of this invention can be performed at less than 100° C., including ambient room temperature, with a radio-frequency, plasma-assisted, chemical-vapor deposition process. The amorphous carbon film produced using the methods of this invention adheres well to many types of substrates, including for example glasses, metals, semiconductors, and plastics.

Attachment of a fullerene moiety to reactive amino group sites of an amine-containing polymer to form the fullerene-graft, amine-containing polymers may be performed as described in U.S. Pat. No. 5,292,813. Chemical modification in this manner allows for direct incorporation of the fullerenes into the stent. In another embodiment, the fullerenes may be deposited on the surface of the stent or synthetic grafts as described above. (see, WO 99/32184 to Leone et al., incorporated by reference). Fullerenes (e.g., $C_{60}$) may also be attached through an epoxide bond to the surface of stainless steel (Yamago et al., Chemical Derivatization of Organofullerenes through Oxidation, Reduction and C—O and C—C Bond Forming Reactions. *J. Org. Chem.*, 58 4796-4798 (1998), incorporated herein by reference). The attachment is through a covalent linkage to the oxygen. This compound and the protocols for coupling are commercially available from BuckyUSA. (BuckyUSA, Houston, Tex.).

(E) Addition of Antibodies and Growth Factor to the Matrix—

Antibodies that promote adherence of progenitor endothelial cells, and growth factors for promoting cell growth and differentiation are incorporated into the matrix, either covalently or noncovalently. Antibodies and growth factor may be incorporated into the matrix layer by mixing the antibodies and growth factor with the matrix coating solution and then applied to the surface of the device. Usually, antibodies and growth factors are attached to the surface of the outermost layer of matrix that is applied on the luminal surface of the device, so that the antibodies and growth factor are projecting on the surface that is in contact with the circulating blood. Antibodies and growth factors are applied to the surface matrix using standard techniques.

In one embodiment, the antibodies are added to a solution containing the matrix. For example, Fab fragments on anti-CD34 monoclonal antibody are incubated with a solution containing human fibrinogen at a concentration of between 500 and 800 mg/dl. It will be appreciated that the concentration of anti-CD34 Fab fragment will vary and that one of ordinary skill in the art could determine the optimal concentration without undue experimentation. The stent is added to the Fab/fibrin mixture and the fibrin activated by addition of concentrated thrombin (at a concentration of at least 1000 U/ml). The resulting polymerized fibrin mixture containing the Fab fragments incorporated directly into the matrix is pressed into a thin film (less than 100 μm) on the surface of the stent or synthetic graft. Virtually any type of antibody or antibody fragment can be incorporated in this manner into a matrix solution prior to coating of a stent or synthetic graft.

For example, in another embodiment, whole antibodies with or without antibody fragments and growth factors are covalently coupled to the matrix. In one embodiment, the antibodies and growth factor(s) are tethered covalently the matrix through the use of hetero- or homobifunctional linker molecules. As used herein the term "tethered" refers to a covalent coupling of the antibody to the matrix by a linker molecule. The use of linker molecules in connection with the present invention typically involves covalently coupling the linker molecules to the matrix after it is adhered to the stent. After covalent coupling to the matrix, the linker molecules provide the matrix with a number of functionally active groups that can be used to covalently couple one or more types of antibody. FIG. 1A provides an illustration of coupling via a cross-linking molecule. An endothelial cell, 1.01, binds to an antibody, 1.03, by a cell surface antigen, 1.02. The antibody is tethered to the matrix, 1.05-1.06, by a cross-linking molecule, 1.04. The matrix, 1.05-1.06, adheres to the stent, 1.07. The linker molecules may be coupled to the matrix directly (i.e., through the carboxyl groups), or through well-known coupling chemistries, such as, esterification, amidation, and acylation. The linker molecule may be a di- or tri-amine functional compound that is coupled to the matrix through the direct formation of amide bonds, and provides amine-functional groups that are available for reaction with the antibodies. For example, the linker molecule could be a polyamine functional polymer such as polyethyleneimine (PEI), polyallylamine (PALLA) or polyethyleneglycol (PEG). A variety of PEG derivatives, e.g., mPEG-succinimidyl propionate or mPEG-N-hydroxysuccinimide, together with protocols for covalent coupling, are commercially available from Shearwater Corporation, Birmingham, Ala. (See also, Weiner et al., Influence of a poly-ethyleneglycol spacer on antigen capture by immobilized antibodies. *J. Biochem. Biophys. Methods* 45:211-219 (2000), incorporated herein by reference). It will be appreciated that the selection of the particular coupling agent may depend on the type of antibody used and that such selection may be made without undue experimentation. Mixtures of these polymers can also be used. These molecules contain a plurality of pendant amine-functional groups that can be used to surface-immobilize one or more antibodies.

Antibodies may be attached to $C_{60}$ fullerene layers that have been deposited directly on the surface of the stent. Cross linking agents may be covalently attached to the fullerenes. The antibodies are then attached to the cross-linking agent, which in turn is attached to the stent. FIG. 1B provides an illustration of coupling by $C_{60}$. The endothelial cell, 2.01, is bound via a cell surface antigen, 2.02, to an antibody, 2.03, which in turn is bound, covalently or non-covalently to the matrix, 2.04. The matrix, 2.04, is coupled covalently via $C_{60}$, 2.05, to the stent, 2.06.

Small molecules of the invention comprise synthetic or naturally occurring molecules or peptides which can be used in place of antibodies, growth factors or fragments thereof. For example, lectin is a sugar-binding peptide of non-immune origin which occurs naturally. The endothelial cell specific Lectin antigen (Ulex Europaeus Uea 1) (Schatz et al. 2000 Human Endometrial Endothelial Cells: Isolation, Characterization, and Inflammatory-Mediated Expression of Tissue Factor and Type 1 Plasminogen Activator Inhibitor. *Biol Reprod* 62: 691-697) can selectively bind the cell surface of progenitor endothelial cells.

Synthetic "small molecules" have been created to target various cell surface, proteins, glucoproteins, polysaccharides and receptors. These molecules selectively bind a specific surface moieties and can target specific cell types such as progenitor endothelial cells. Small molecules can be synthesized to recognize endothelial cell surface markers such as VEGF. SU11248 (Sugen Inc.) (Mendel et al. 2003 In vivo antitumor activity of SU11248, a novel tyrosine kinase inhibitor targeting vascular endothelial growth factor and platelet-derived growth factor receptors: determination of a pharmacokinetic/pharmacodynamic relationship. *Clin Cancer Res.* January; 9(1):327-37), PTK787/ZK222584 (Drevs J. et al. 2003 Receptor tyrosine kinases: the main targets for new anticancer therapy. *Curr Drug Targets*. February; 4(2): 113-21) and SU6668 (Laird, A D et al. 2002 SU6668 inhibits Flk-1/KDR and PDGFRbeta in vivo, resulting in rapid apoptosis of tumor vasculature and tumor regression in mice. *FASEB J*. May; 16(7):681-90) are small molecules which bind to VEGFR-2.

Another subset of synthetic small molecules which target the endothelial cell surface are the alpha(v)beta(3) integrin inhibitors. SM256 and SD983 (Kerr J S. et al. 1999 Novel small molecule alpha v integrin antagonists: comparative anti-cancer efficacy with known angiogenesis inhibitors. *Anticancer Res* March-April; 19(2A):959-68) are both synthetic molecules which target and bind to alpha(v)beta(3) present on the surface of endothelial cells.

The present invention provides a drug delivery system comprising: coated medical devices such as stents, stent grafts, heart valves, catheters, vascular prosthetic filters, artificial heart, external and internal left ventricular assist devices (LVADs), and synthetic vascular grafts, for the treatment of diseases, including tumor and vascular diseases, such as restenosis, artherosclerosis, thrombosis, blood vessel obstruction, and the like. In one embodiment, the coating on the present medical device comprises a biocompatible matrix, at least one antibody, and at least one compound such as a ligand.

Transgenic cells incorporating at least one transgene that is introduced into the cells by viral or non-viral based genetic procedures. The transgene codes for at least one therapeutic drug and is expressed continuously or upon induction. In one embodiment, the therapeutic drug is a protein. The transgenic cells also present at least one antigen on its cell surface that can be recognized and bound by the antibody that is coated on the surface of the medical device.

Figure 11:
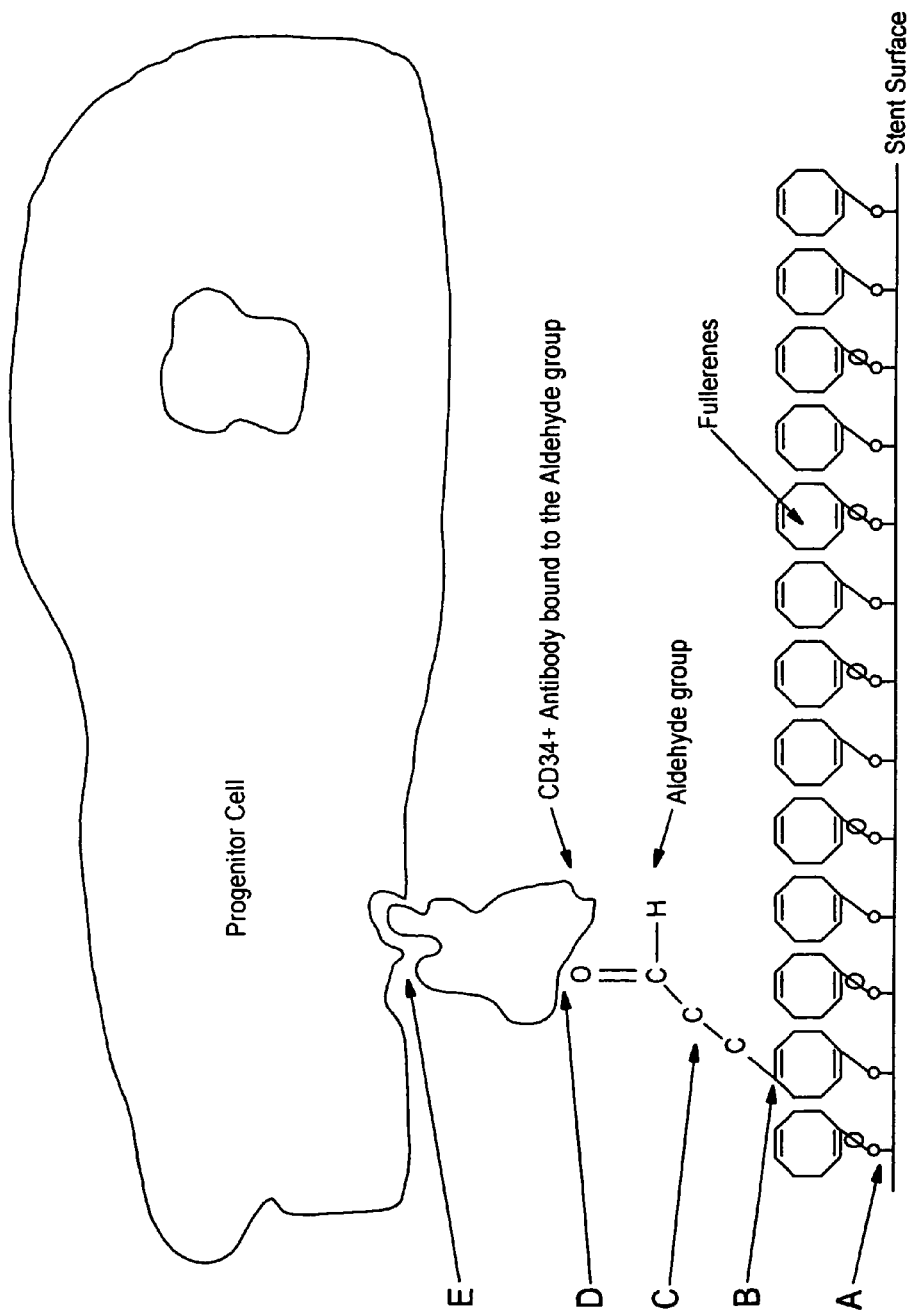
FIG. 11 is schematic diagram of a functional fullerene coated stent surface of the invention binding a progenitor cell.
Figure 14H:
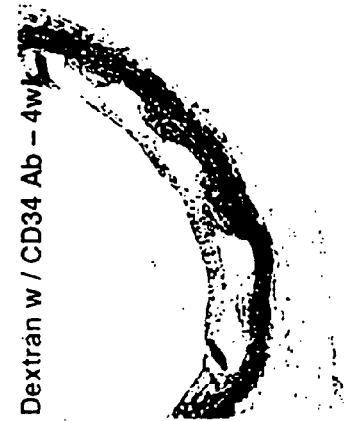
FIGS. 14H-14M are histological photomicrographs of cross-sections through coronary arteries of explants from male Yorkshire swine which were implanted for 4 weeks: uncoated (Bare stainless steel) (14H and 14I), dextran-coated control (14J and 14K), and dextran/anti-CD34 antibody-coated (14L and 14M).
Figure 14J:
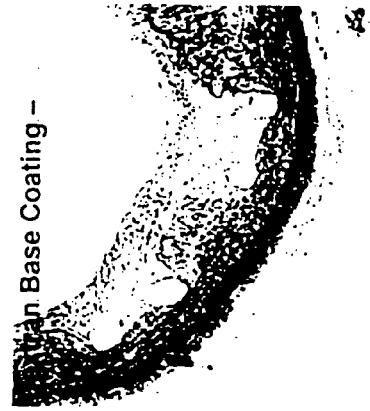
Figure 14L:
Figure 14I:
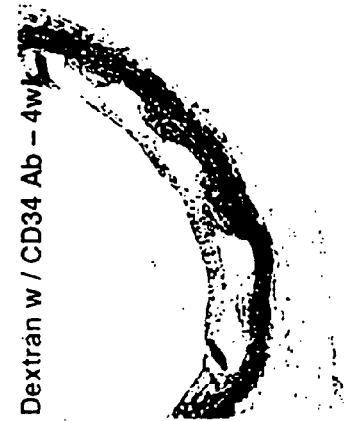
Figure 14K:
Figure 14M:
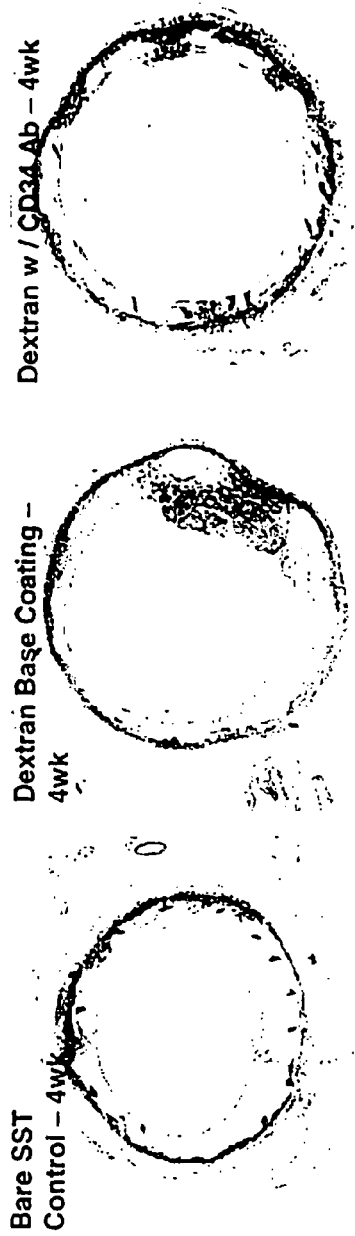

As used herein "antibody" refers to antibody or antibody fragment, or a combination of antibody and fragments, which can be a monoclonal antibody, a polyclonal antibody, a chimeric antibody, or a humanized antibody. The antibody fragment of the invention comprises any fragment size, such as large and small molecules which retain the characteristic to recognize and bind the target antigen as the antibody (FIGS. 1A, 1B, and 11).

As used herein "ligand" refers to a molecule that binds a receptor on the mammalian cell. For example, the ligand can be an antibody, antibody fragment (FIGS. 1A, 1B, 11, and 17), cell adhesion molecule, basement membrane component which recognizes and binds a specific epitope or structure on the membrane of the cell. In the embodiment of the invention which uses genetically altered cells, the ligand can be specifically selected to recognize and bind to a gene product produced by the exogenous DNA introduced into the cells.

As used herein "protein" refers to a polymer of amino acids of any length. The polymer may be linear or branched, may comprise modified amino acids, and may be interrupted by non-amino acids. The polymer may be naturally occurring peptides, proteins, or modified and synthetic forms thereof including biologically active fragments, derivatives, analogues, mimetics, and non-functional or dominant negative mutants.

The medical device of this invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a suture, a vascular anastomosis clip, an indwelling venous or arterial catheter, a vascular sheath and a drug delivery port. The medical device can be made of numerous materials depending on the device. For example, a stent of the invention can be made of stainless steel, Nitinol (NiTi), or chromium alloy. Synthetic vascular grafts can be made of a cross-linked PVA hydrogel, polytetrafluoroethylene (PTFE), expanded polytetrafluoroethylene (ePTFE), porous high density polyethylene (HDPE), polyurethane, and polyethylene terephthalate.

The biocompatible matrix forming the coating of the present device comprises a synthetic material such as polyurethanes, segmented polyurethane-urea/heparin, poly-L-lactic acid, cellulose ester, polyethylene glycol, polyvinyl acetate, dextran and gelatin, a naturally-occurring material such as basement membrane components such as collagen, elastin, laminin, fibronectin, vitronectin; heparin, fibrin, cellulose, and amorphous carbon, or fullerenes.

In one embodiment, the medical device comprises a biocompatible matrix comprising fullerenes. In this embodiment, the fullerene can range from about $C_{20}$ to about $C_{150}$ in the number of carbon atoms, and more particularly, the fullerene is $C_{60}$ or $C_{70}$. The fullerene of the invention can also be arranged as nanotubes on the surface of the medical device.

The antibody for providing to the coating of the medical device comprises at least one antibody that recognizes and binds a transgenic cell surface antigen which can be expressed by an endogenous gene or by a transgene and modulates the adherence of the cells onto the surface of the medical device. The antibody can be covalently or noncovalently attached to the surface of the matrix, or tethered covalently by a linker molecule to the outermost layer of the matrix coating the medical device. In this aspect of the invention, for example, the monoclonal antibodies can further comprises Fab or F (ab') 2 fragments.

The antibody of the invention recognizes and binds antigens with specificity for the mammal being treated and their specificity is not dependent on cell lineage. In one embodiment, the antibody is specific for a human progenitor endothelial cell surface antigen such as CD133, CD14, CD34, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, HAD-DR and others.

In another embodiment, the coating of the medical device comprises at least one layer of a biocompatible matrix as described above, the matrix comprising an outer surface for attaching a therapeutically effective amount of at least one type of small molecule of natural or synthetic origin. The small molecule recognizes and interacts with an antigen on a transgenic cell surface to immobilize the transgenic cell on the surface of the device and to induce transgene expression. The small molecules can be derived from a variety of sources such as cellular components such as fatty acids, proteins, nucleic acids, saccharides and the like and can interact with a receptor on the surface of a transgenic cell. In this embodiment of the invention, the coating on the medical device can further comprise a compound such as a ligand in conjunction with the coating comprising an antibody.

Both viral and non-viral based genetic procedures can be used to introduce transgenes for generating transgenic cells. Transgenic cells of the invention express and secrete therapeutic drugs coded by transgenes that are either transiently or stably incorporated. Additional transgenes can be incorporated to confer survival, selection and/or growth advantage. Various cells such as endothelial cells or leukocytes including neutrophil, eosinophil, basophil, monocyte and lymphocytes or somatic cells, or a combination of these cells can be modified to produce transgenic cells, which may be either non-repopulating or repopulating. Transgenic cells can be cultured in vitro, collected, and stored. Transgenic cells producing a variety of therapeutic drugs can be generated by incorporating different transgenes to serve different therapeutic purposes. Transgenic cells can be administered as a single or mixed populations via systemic or local routes. Various amounts of transgenic cells can be administered to release different amount of therapeutic drugs upon individual conditions. In one embodiment, transgenic cells are repopulating progenitor endothelial cells. In a further embodiment, transgenic progenitor endothelial cells are administered locally with catheter based delivery or dual balloon inflation method.

In one embodiment, transgenic cells further comprise an additional transgene that expresses an exogenous cell surface antigen, which can be specifically recognized and bound by the antibody that is coated in the matrix of the medical device. Transgene expression and product secretion can be continuous or contingent upon the activation of an inducible promoter via exogenous excitation.

The therapeutic compounds coded by the transgenes of the invention can be any molecule with a desired physiological effect, and can be, but is not limited to, proteins as defined including growth factors, chemokines and cytokines, ligands and receptors, and other functional proteins and non-protein excretable compounds. In one embodiment, a therapeutic compound is a protein selected from the group consisting of endothelial nitric oxide synthase (eNOS), vascular endothelial growth factor (VEGF), an anti-inflammatory factor, and an inflammation-modulating factor.

The exciting drug for transgene expression and product secretion of the invention can be a ligand that binds the transgenic cell surface antigen and triggers downstream signaling pathway activation, or can be taken up by the transgenic cell and stimulate gene expression through an inducible promoter. In one embodiment, the ligand or drug is administered systemically. In another embodiment, the ligand or drug is coated in the matrix of the implanted device and administered locally.

The invention provides methods for treating a variety of diseases, which can be, but not limited to, tumors, vascular diseases, and healing response. The methods provide improvement over prior art in terms of target site delivery of a variety of drugs of desired amount upon demand.

The invention provides a method for treating tumors and their metastases. In this embodiment, the transgene can code for (1) an antiangiogenic factor, such as interferons (IFNs), thrombospondin (TSP), angiostatin, endostatin, oncostatin M (OSM), and Rho, which inhibits neovascularization that is a prerequisite for tumor progressive growth; or (2) an tumor suppressive protein, such as p53, Rb, E1, BRCA1, antibody or dominant negative mutant of a cell growth activator such as a growth factor, a cyclin dependent kinase (CDK) or a cyclin, E2F, NFκB; or a combination of these genes.

As used herein the phrase "anti-angiogenic factor" refers to a molecule that is capable of inhibiting angiogenesis.

The invention also provides methods for treating vascular disease. In one embodiment, the invention is used to treat ischemic conditions, in which the transgene codes for an angiogenic factor such as pleiotrophin, angiogenin, angiopoietin, an integrin stimulating factor, or an antibody or dominant negative mutant of an anti-angiogenic factor.

As used herein the phrase "angiogenic factor" refers to a molecule that is capable of stimulating angiogenesis.

In another embodiment, the invention is used to treat atherosclerosis, restenosis, thrombosis, aneurysm or blood vessel obstruction. In this embodiment of the invention, transgene can code for (a) eNOS or VEGF that promotes re-endothelialization; or (b) an anti-inflammatory or inflammation-modulating factor such as IFN-β, IFN-α, TGF-β, or interleukin-10 (IL-10); or (c) an inhibitor of smooth muscle cell growth, migration, or differentiation that inhibits intimal hyperplasia; or a combination of these genes.

The invention also provides an engineered method for inducing a healing response. In one embodiment, a method is provided for rapidly inducing the formation of a confluent layer of endothelium in the luminal surface of an implanted device in a target lesion of an implanted vessel, in which transgenic cells are progenitor endothelial cells that express eNOS, VEGF, or an anti-inflammatory or inflammation-modulating factor. In this embodiment of the invention, a medical device is provided of increased biocompatibility over prior art devices, and decreases or inhibits tissue-based excessive intimal hyperplasia and restenosis by decreasing or inhibiting smooth muscle cell migration, smooth muscle cell differentiation, and collagen deposition along the inner luminal surface at the site of implantation of the medical device.

In one embodiment of the invention, a method for coating a medical device comprises the steps of: applying at least one layer of a biocompatible matrix to the surface of the medical device, wherein the biocompatible matrix comprises at least one component selected from the group consisting of a polyurethane, a segmented polyurethane-urea/heparin, a poly-L-lactic acid, a cellulose ester, a polyethylene glycol, a polyvinyl acetate, a dextran, gelatin, collagen, elastin, laminin, fibronectin, vitronectin, heparin, fibrin, cellulose and carbon and fullerene, and applying to the biocompatible matrix, simultaneously or sequentially, at least one antibody, and optionally one compound which induces transgene expression.

The invention further provides a method for treating diseases such as tumor, vascular disease, and wound healing in a mammal comprises implanting a medical device into a vessel or tubular organ of the mammal, wherein the medical device is coated with (a) a biocompatible matrix; (b) at least one antibody; and optionally (c) one compound, introducing transgenic cells into the mammal that is need of the treatment, and optionally administering a compound, wherein the antibody coated in the matrix of the medical device recognizes and binds an antigen expressed on the transgenic cell surface, so that the transgenic cells are immobilized on the surface of the matrix, and at least one therapeutic drug coded by a transgene is expressed upon the compound excitation and secreted at a designated site.

The invention further provides a method for treating vascular disease in a mammal comprises implanting a medical device into a vessel or tubular organ of the mammal, wherein the medical device is coated with (a) a biocompatible matrix, (b) at least one antibody, and optionally (c) one compound, and introducing transgenic cells into the mammal that is in need of the treatment, and optionally administering a compound, wherein the antibody coated in the matrix of the medical device recognizes and binds an antigen expressed only on the transgenic cell surface so that the transgenic cells are immobilized on the surface of the matrix. The transgenic (genetically-altered) cells contain genetic material which encodes at least one therapeutic drug constitutively or upon activation by a signal such as a compound.

The present transgenic cells contain at least one expressible transgene that can code for, but not limited to (1) growth factors including family members such as platelet derived growth factor (PDGF), transforming growth factor (TGF), epidermal growth factor (EGF), fibroblast growth factor (FGF), insulin like growth factors (IGF), vascular endothelial growth factor (VEGF), heparin binding growth factors, hepatoma-derived growth factor (HDGF), hepatocyte growth factor/scatter factor (HGF), placental growth factor (PIGF), platelet derived endothelial cell growth factor (PD-ECGF), stem cell factor (SCF), and their other protein forms; (2) Chemokines such as CXC families, CC families, C families, and their other protein forms; (3) cytokines such as a disintegrin and metalloprotease (ADAM), annexin V, B7 & CD28/CTLA-4 receptor families, bone morphogenetic protein (BMP), caspase, CD44, CD44H, endothelin-1 (ET-1), eph, erythropoietin (Epo), intercellular adhesion molecule-3/CD50 (ICAM-3), macrophage stimulating protein (MSP), matrix metalloproteinase (MMP), neurotrophic factors, endothelial nitric oxide synthase (eNOS), NKG2D, platelet endothelial cell adhesion molecule-1 (PECAM-1/CD31), pleiotrophin/midkine (PTN/MK), transferrin receptor (sTfR), hedgehog, STAT, stem cell marker, Th1/Th2, thrombopoietin (Tpo), tumor necrosis factor family, VCAM-1/CD16, monoclonal non-specific suppressor factor beta (MNSFbeta), 6Ckine (SLC), B-lymphocyte chemoattractant (BCA-1/BLC), leukemia inhibitory factor, monocyte-derived neutrophil-activating peptide (GRO), and their other protein forms; (4) other functional proteins involved in the regulation of signal transduction, cell cycle regulation, cell division, and/or cell differentiation, such as ligands, receptors, phosphorylases, kinases, transcriptional factors, and their other protein forms.

In one embodiment, antiangiogenic factors for use in the invention are, for example, interferons (IFNs), thrombospondin (TSP), angiostatin, and endostatin, oncostatin M (OSM), blockers of integrin engagement, metalloproteinases inhibitors, inhibitors of endothelial cell phosphorylation, dominant negative receptors for angiogenesis inducers, antibodies of angiogenesis inducers, other proteins acting by other means, and their other protein forms. Other angiogenic factors include angiogenin, angiopoietins, integrin stimulating factors such as Del-1, and their other protein forms.

Additional growth factors for use in the invention are, for example, pleiotrophin, midkines, VEGF family including VEGF-2, VEGF-C, and VEGF-D, FGF family, including FGF-1, FGF-2, FGF-5, and FGF-18, hepatoma-derived growth factor (HDGF), hepatocyte growth factor/scatter factor (HGF), members of the epidermal growth factor (EGF) family, including transforming growth factor alpha, EGF, and TGF-alpha-HIII, and platelet derived growth factor (PDGF), including AA, AB, and BB isoforms.

EXPERIMENTAL EXAMPLES

This invention is illustrated in the experimental details section which follows. These sections set forth below the understanding of the invention, but are not intended to, and should not be construed to, limit in any way the invention as set forth in the claims which follow thereafter.

Example 1

Endothelial Progenitor Cell Phenotyping

Endothelial Progenitor Cells (EPC) were isolated either by CD34+ Magnetic Bead Isolation (Dynal Biotech) or enriched medium isolation as described recently (Asahara T, Murohara T, Sullivan A, et al. Isolation of putative progenitor endothelial cells for angiogenesis. Science 1997; 275: 964-7). Briefly, peripheral venous blood was taken from healthy male volunteers and the mononuclear cell fraction was isolated by density gradient centrifugation, and the cells were plated on human fibronectin coated culture slides (Becton Dickinson) in EC basal medium-2 (EBM-2) (Clonetics) supplemented with 5% fetal bovine serum, human VEGF-A, human fibroblast growth factor-2, human epidermal growth factor, insulin-like growth factor-1, and ascorbic acid. EPCs were grown up to seven days with culture media changes every 48 hours. The results of these experiments are shown in FIGS. 2A and 2B. FIGS. 2A and 2B show that the anti-CD34 isolated cell appear more spindle-like, which indicates that the cells are differentiating into endothelial cells.

EC phenotype was determined by immunohistochemistry. Briefly, EPC were fixed in 2% Paraformaldehyde (PFA) (Sigma) in Phosphate buffered saline (PBS) (Sigma) for 10 minutes, washed 3× with PBS and stained with various EC specific markers; rabbit anti-human VEGFR-2 (Alpha Diagnostics Intl. Inc.), mouse anti-human Tie-2 (Clone Ab33, Upstate Biotechnology), mouse anti-human CD34 (Becton Dickinson), EC-Lectin (Ulex Europaeus Uea 1) (Sigma) and mouse anti-human Factor 8 (Sigma). The presence of antibody was confirmed by exposure of the cells to a fluorescein isothiocyanate-conjugated (FITC) secondary antibody. Propidium Iodine (PI) was used as a nuclear marker. The results of these experiments are shown in FIGS. 2C-2G. FIG. 2C shows that VEGFR-2 is expressed after 24 hours in culture, confirming that the cells are endothelial cells. FIGS. 2D and 2F show the nuclear staining of the bound cells after 7 days of incubation and FIGS. 2E and 2G the same field of cells stained with an FITC conjugated anti-Tie-2 antibody.

Figure 3B:
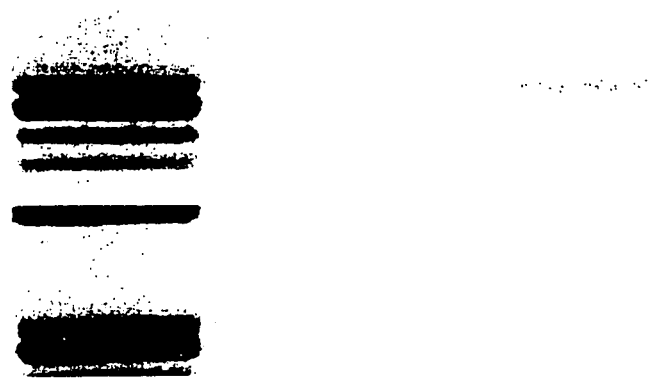

EPCs ability to express endothelial nitric oxide synthase (eNOS), a hallmark of EC function, was determined by Reverse Transcriptase-Polymerase Chain Reaction (rt-PCR) for eNOS mRNA. EPCs were grown up to seven days in EBM-2 medium after which total RNA was isolated using the GenElute Mammalian total RNA kit (Sigma) and quantified by absorbance at 260 nm. Total RNA was reverse transcribed in 20 µL volumes using Omniscript RT kit (Qiagen) with 1 µg of random primers. For each RT product, aliquots (2-10 µL) of the final reaction volume were amplified in two parallel PCR reactions using eNOS (299 bp product, sense 5'-TTCCGGGGATTCTGGCAGGAG-3' SEQ ID NO: 1, antisense 5'-GCCATGGTAACATCGC-CGCAG-3' SEQ ID NO: 2) or GAPDH (343 bp product, sense 5'-CTCTAAGGCTGTGGGCAAGGTCAT-3' SEQ ID NO: 3, antisense 5'-GAGATCCACCACCCTGTTGCT-GTA-3' SEQ ID NO: 4) specific primers and Taq polymerase (Pharmacia Biotech Amersham). PCR cycles were as follows: 94° C. for 5 minutes, 65° C. for 45 seconds, 72° C. for 30 seconds (35 cycles for eNOS and 25 cycles for GAPDH). rt-PCR products were analyzed by 2% agarose gel electrophoresis, visualized using ethidium bromide and quantified by densitometry. The results of this experiment are shown in FIGS. 3A and 3B. As seen in FIGS. 3A and 3B, nitric oxide synthetase (eNOS) is expressed after the cells have been incubated in medium for 3 days in culture in the presence or absence of oxygen. eNOS mRNA expression continues to be present after 7-days in culture. The presence of eNOS mRNA indicates that the cells have differentiated into mature endothelial cells by day 3 and have begun to function like fully differentiated endothelial cells.

Example 2

Endothelial Cell Capture by Anti-CD34 Coated Stainless Steel Disks

Human Umbilical Vein Endothelial Cells (HUVEC) (American Type Culture Collection) are grown in endothelial cell growth medium for the duration of the experiments. Cells are incubated with CMDX and gelatin coated samples with or without bound antibody on their surface or bare stainless steel (SST) samples. After incubation, the growth medium is removed and the samples are washed twice in PBS. Cells are fixed in 2% paraformaldehyde (PFA) for 10 minutes and washed three times, 10 minutes each wash, in PBS, to ensure all the fixing agent is removed. Each sample is incubated with blocking solution for 30 minutes at room temperature, to block all non-specific binding. The samples are washed once with PBS and the exposed to 1:100 dilution of VEGFR-2 antibody and incubated overnight. The samples are subsequently washed three times with PBS to ensure all primary antibody has been removed. FITC-conjugated secondary antibody in blocking solution is added to each respective sample at a dilution of 1:100 and incubated for 45 minutes at room temperature on a Belly Dancer apparatus. After incubation, the samples are washed three times in PBS, once with PBS containing 0.1% Tween 20, and then again in PBS. The samples are mounted with Propidium Iodine (PI) and visualized under confocal microscopy.

Figure 4C:
FIGS. 4A-4E are photomicrographs of HUVECs attached to the CMDx and anti-CD34 antibody (4A); gelatin and anti-CD34 antibody (4B); bare stainless steel disc (4C); CMDx coated (4D) and gelatin coated (4E) stainless steel disc which were incubated with HUVEC cell and stained with propidium iodide.
Figure 4B:
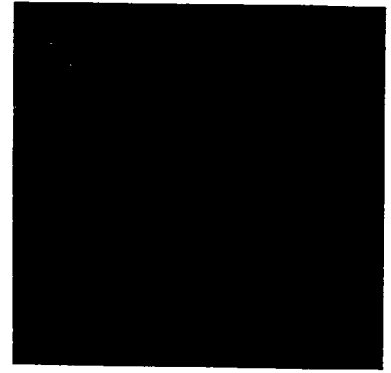
Figure 4E:
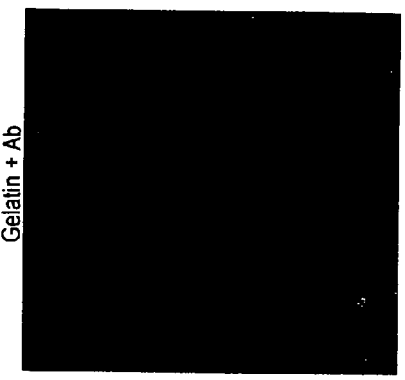
Figure 4A:
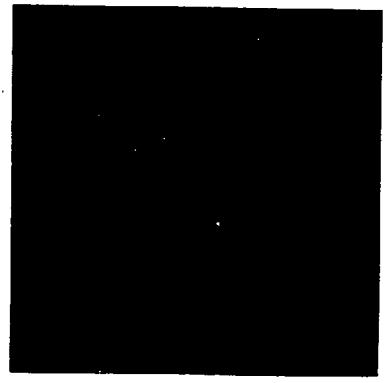
Figure 4D:
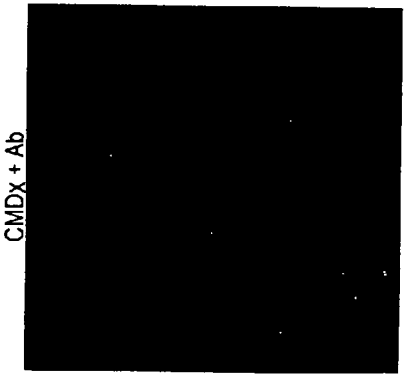

FIGS. 4A-4E are photomicrographs of SST samples coated with CMDX and anti-CD34 antibody (FIG. 4A), gelatin and anti-CD34 antibody coated (FIG. 4B), bare SST (FIG. 4C), CMDX coated and no antibody (FIG. 4D) and gelatin-coated and no antibody (FIG. 4E). The figures show that only the antibody coated samples contain numerous cells attached to the surface of the sample as shown by PI staining. The bare SST control disk shows few cells attached to its surface.

FIGS. 5A-5C are photomicrographs of control samples CMDX-coated without antibody bound to its surface. FIG. 5A shows very few cells as seen by PI staining adhered to the surface of the sample. FIG. 5B shows that the adherent cells are VEGFR-2 positive indicating that they are endothelial cells and FIG. 5C shows a combination of the stained nuclei and the VEGFR-2 positive green fluorescence. FIGS. 5D-F are photomicrographs of control samples coated with gelatin without antibody on its surface. FIG. 5D shows no cells are present since PI staining is not present in the sample and there is no green fluorescence emitted by the samples (see FIGS. 5E and 5F).

FIGS. 6A-6C are photomicrographs of CMDX coated SST samples having anti-CD34 antibody bound on its surface. The figures show that the samples contain numerous adherent cells which have established a near confluent monolayer (FIG. 6A) and which are VEGFR-2 positive (FIGS. 6B and 6C) as shown by the green fluorescence. Similarly, FIGS. 6D-6F are photomicrographs of a gelatin-coated sample with anti-CD34 antibody bound to its surface.

These figures also show that HUVECs attached to the surface of the sample as shown by the numerous red-stained nuclei and green fluorescence from the VEGFR-2/FITC antibody (FIGS. 6E and 6F).

Example 3

VEGFR-2 and Tie-2 Staining of Progenitor Endothelial Cells

Progenitor cell are isolated from human blood as described in the in Example 1 and incubated in growth medium for 24 hours, 7 days, and 3 weeks in vitro. After incubation, the growth medium is removed and the samples are washed twice in PBS. Cells are fixed in 2% paraformaldehyde (PFA) for 10 minutes and washed three times, 10 minutes each wash, in PBS, to ensure all the fixing agent is removed. Each sample is incubated with 440 µl of Goat (for VEGFR-2) or Horse (for Tie-2) blocking solution for 30 minutes at room temperature, to block all non-specific binding. The samples are washed once with PBS and the VEGFR-2 or Tie-2 antibody was added at a dilution of 1:100 in blocking solution and the samples are incubated overnight. The samples are then washed three times with PBS to ensure all primary antibody has been washed away. FITC-conjugated secondary antibody (200 µl) in horse or goat blocking solution is added to each respective sample at a dilution of 1:100 and incubated for 45 minutes at room temperature on a Belly Dancer apparatus. After incubation, the samples are washed three times in PBS, once with PBS containing 0.1% Tween 20, and then again in PBS. The samples are mounted with Propidium Iodine (PI) and visualized under confocal microscopy.

Figure 7:
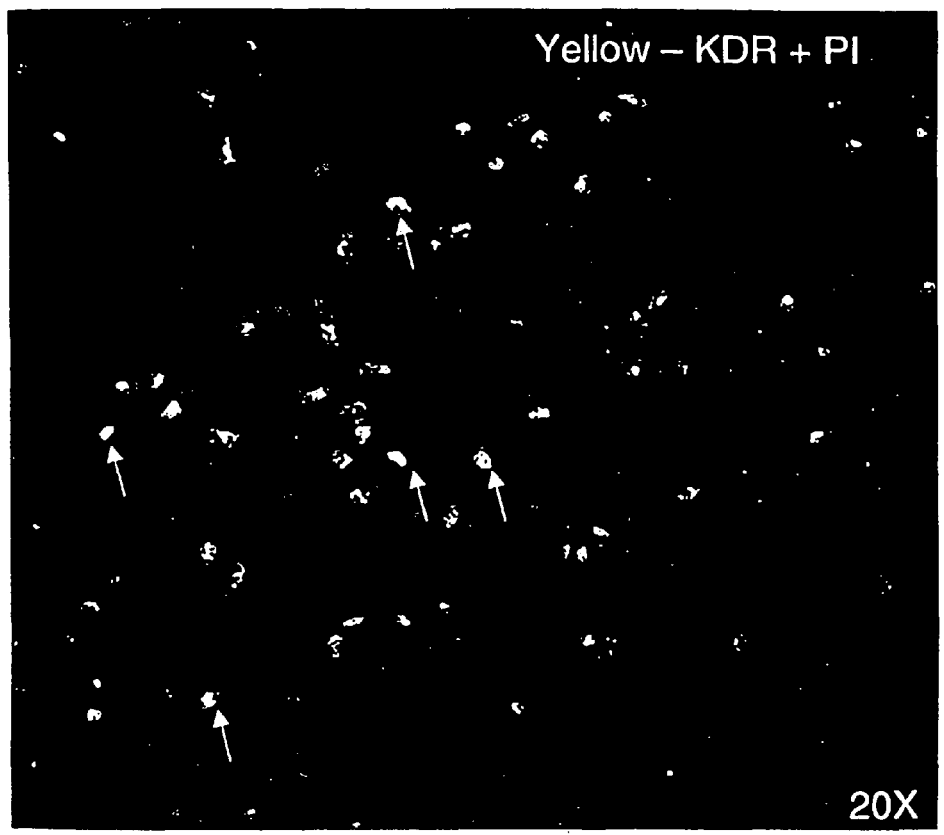
FIG. 7 is a photomicrograph of stainless steel discs coated with CMDx matrix with antibody bound to its surface, which was incubated with progenitor cells for 24 hours. The cells were stained with propidium iodide and FITC labeled anti-KDR antibody.

FIG. 7 is a photomicrograph of a CMDX-coated sample containing CD34 antibody on its surface which was incubated with the cells for 24 hours, and shows that progenitor cells were captured on the surface of the sample and as demonstrated by the red-stained nuclei present on the surface of the sample. The figure also shows that about 75% of the cells are VEGFR-2 positive with a round morphology.

FIGS. 8A and 8B are from a sample which was incubated with the cells for 7 days. As seen in FIG. 8A, there are cells present on the sample as shown by the red-stained nuclei, which are VEGFR-2 positive (FIG. 8B, 100%) and are more endothelial in structure as shown by the spindle shape of the cells. FIGS. 9A and 9B are photomicrographs of CMDX-coated sample containing CD34 antibody on its surface, which was incubated for 7 days with the cells and after incubation, the sample was exposed to Tie-2 antibody. As seen in FIG. 9A, there are numerous cells attached to the surface of the samples as shown by the red-stained nuclei. The cells adhered to the sample are also Tie-2 positive (100%) as seen by the green fluorescence emitted from the cells (FIG. 9B). In summary, after 7 days of incubation of the cells with the samples, the CD34 antibody-coated samples are able to capture endothelial cells on their surface as seen by the numerous cells attached to the surface of the samples and the presence of VEGFR-2 and Tie-2 receptors on the surface of the adhered cells. In addition, the presence of 100% endothelial cells on the surface of the samples at 7 days indicates that the non-endothelial cells may have detached or that all adherent cells have begun to express endothelial cell markers by day 7.

Figure 10B:
Figure 10C:
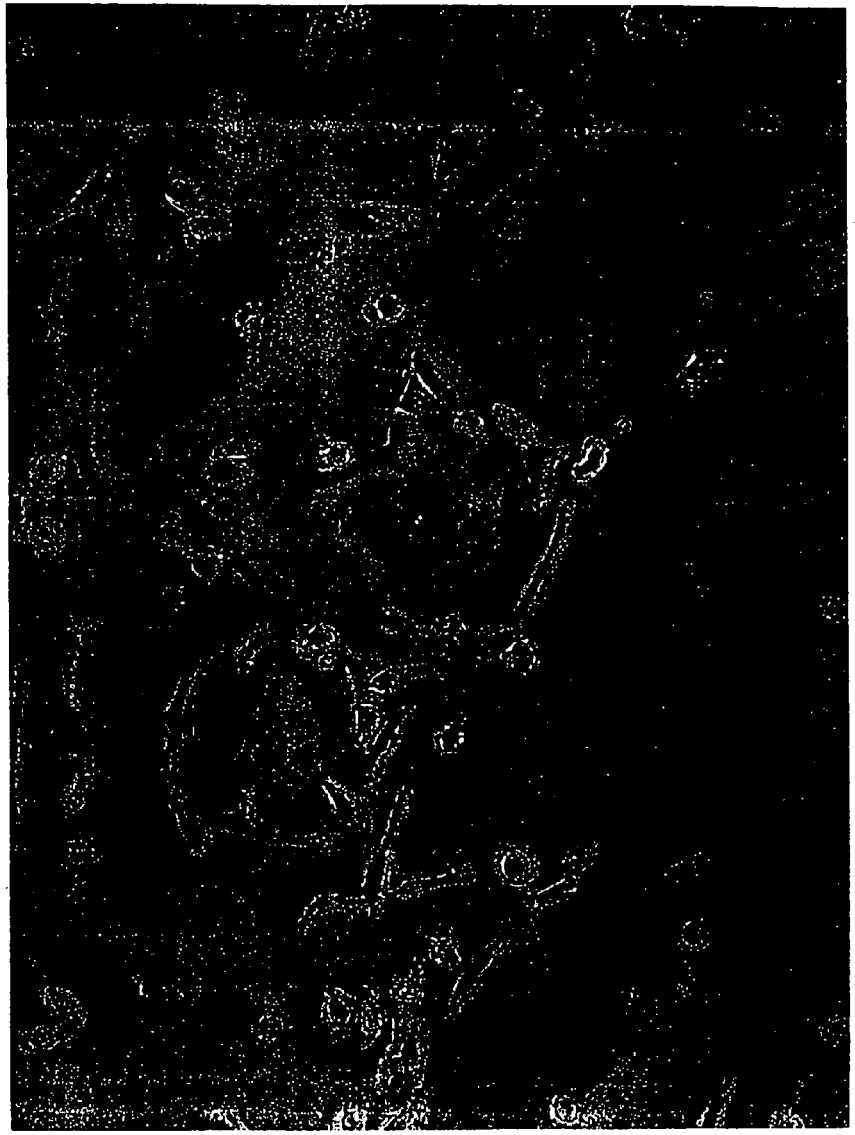

FIGS. 10A-10C are phase contrast photomicrographs of the progenitor endothelial cells grown for 3 weeks in endothelial cell growth medium. FIG. 10A demonstrates the cells have differentiated into matured endothelial cells as shown by the two-dimensional tube-like structures (arrow) reminiscent of a lumen of a blood vessel at the arrow. FIG. 10B shows that there is a three-dimensional build-up of cells in multiple layers; i.e.; one on top of the other, which confirms reports that endothelial cells grown for prolonged periods of time begin to form layers one on top of the other. FIG. 10C shows progenitor cells growing in culture 3 weeks after plating which have the appearance of endothelial cells, and the figure confirms that the cells are endothelial cells as demonstrated by the green fluorescence of the CD34/FITC antibodies present on their surface.

The above data demonstrate that white blood cells isolated from human blood have CD34 positive progenitor cells and that these cells can develop into mature endothelial cells and readily express endothelial cell surface antigens. (VEGFR-2 and Tie-2) The data also show that antibodies against progenitor or stem cell surface antigens can be used to capture these cells on the surface of a coated medical device of the invention.

Example 4

Fullerene Coated and Fullerene Coated with Anti-CD34 Antibody and/or an Endothelial Cell Growth Factor (Ang-2, VEGF) Stainless Steel Stainless steel stents and disks are derivatized with a functional fullerene layer for attaching antibodies and/or growth factors (i.e., VEGF or Ang-2) using the following procedure:

In the first step, the surface of the SST stent or disk is activated with 0.5M HCL which also cleans the surface of any passivating contaminants. The metal samples are removed from the activation bath, rinsed with distilled water, dried with methanol and oven-dried at 75° C. The stents are then immersed in the toluene derivative solution with fullerene oxide ($C_{60}$—O), for a period of up to 24 hours. The fullerene oxide binds to the stent via Fe—O, Cr—O and Ni—O found on the stent. The stents are removed from the derivatizing bath, rinsed with toluene, and placed in a Soxhlet Extractor for 16 hours with fresh toluene to remove any physisorbed $C_{60}$. The stents are removed and oven-dried at 105° C. overnight. This reaction yields a fully derivatized stent or disk with a monolayer of fullerenes.

In step 2 a di-aldehyde molecule is formed in solution by reacting sebacic acid with thionyl chloride or sulfur oxychloride ($SOCl_2$) to form Sebacoyl chloride. The resultant Sebacoyl chloride is reacted with $LiAl[t-OButyl]_3$ H and diglyme to yield 1,10-decanediol as shown below:

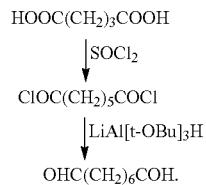

In step 3, an N-methyl pyrolidine derivate is formed on the surface of the stent or disk (from step 1). The fullerene molecule is further derivatized by reacting equimolar amounts of fullerene and N-methylglycine with the 1,10-decanediol product of the reaction of step 2, in refluxing toluene solution under nitrogen for 48 hours to yield N-methyl pyrolidine-derivatized fullerene-stainless steel stent or disk as depicted below.

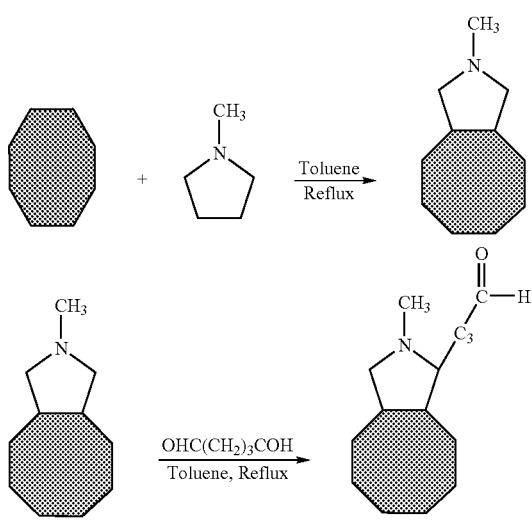

The derivatized stainless steel stent or disk is washed to remove any chemical residue and used to bind the antibodies and/or (VEGF or Ang-2) using standard procedures. Progenitor cell are isolated from human blood as described in Example 1 and exposed to the anti-CD34 antibody coated fullerene disks. After incubation, the growth medium is removed and the samples are washed twice in PBS. Cells are fixed in 2% paraformaldehyde (PFA) for 10 minutes and washed three times, 10 minutes each wash, in PBS, to ensure all the fixing agent is removed. Each sample is incubated with blocking solution for 30 minutes at room temperature, to block all non-specific binding. The samples are washed once with PBS and the exposed to 1:100 dilution of VEGFR-2 antibody and incubated overnight. The samples are subsequently washed three times with PBS to ensure all primary antibody has been removed. FITC-conjugated secondary antibody in blocking solution is added to each respective sample at a dilution of 1:100 and incubated for 45 minutes at room temperature on a Belly Dancer apparatus. After incubation, the samples are washed three times in PBS, once with PBS containing 0.1% Tween 20, and then again in PBS. The samples are mounted with Propidium Iodine (PI) and visualized under confocal microscopy. FIG. 11 shows a schematic representation of a functional fullerene coated stent surface of the invention binding a progenitor cell. FIGS. 12A-12B are, respectively, photomicrographs of fullerene-coated control sample without antibody stained with PI (12A) and anti-VEGFR-2/FITC-conjugated antibody stained. FIGS. 12C and 12D are photomicrographs of a sample coated with a fullerene/anti-CD34 antibody coating. As shown in the figures, the anti-CD34 antibody coated sample contains more cells attached to the surface which are VEGFR-2 positive.

Fullerene-coated samples with and without antibodies are implanted into Yorkshire pigs as described in Example 5. The stents are explanted for histology and the stented segments are flushed with 10% buffered Formalin for 30 seconds followed by fixation with 10% buffered Formalin until processed. Five sections are cut from each stent; 1 mm proximal to the stent, 1 mm from the proximal end of the stent, mid stent, 1 mm from the distal edge of the stent and 1 mm distal to the stent. Sections are stained with Hematoxylin & Eosin (HE) and Elastin Trichrome. FIGS. 13A-13D are photomicrographs of cross-sections through coronary artery explants of stents which had been implanted for 4 weeks. The data show that the fullerene-coated (FIGS. 13B and 13D) stents inhibit excessive intimal hyperplasia at the stent site over the control (bare stent, FIGS. 13A and 13C).

Example 5

Porcine Balloon Injury Studies

Implantation of antibody-covered stents is performed in juvenile Yorkshire pigs weighing between 25 and 30 kg. Animal care complies with the "Guide for the Care and Use of Laboratory Animals" (NIH publication No. 80-23, revised 1985). After an overnight fast, animals are sedated with ketamine hydrochloride (20 mg/kg). Following the induction of anesthesia with thiopental (12 mg/kg) the animals are intubated and connected to a ventilator that administers a mixture of oxygen and nitrous oxide (1:2 [vol/vol]). Anesthesia is maintained with 0.5-2.5 vol % isoflurane. Antibiotic prophylaxis is provided by an intramuscular injection of 1,000 mg of a mixture of procaine penicillin-G and benzathine penicillin-G (streptomycin).

Under sterile conditions, an arteriotomy of the left carotid artery is performed and a 8F-introducer sheath is placed in the left carotid artery. All animals are given 100 IU of heparin per kilogram of body weight. Additional 2,500 IU boluses of heparin are administered periodically throughout the procedure in order to maintain an activated clotting time above 300 seconds. A 6F guiding catheter is introduced through the carotid sheath and passed to the ostia of the coronary arteries. Angiography is performed after the administration of 200 ug of intra coronary nitro glycerin and images analyzed using a quantitative coronary angiography system. A 3F-embolectomy catheter is inserted into the proximal portion of the coronary artery and passed distal to the segment selected for stent implantation and the endothelium is denuded. A coated R stent incorporating an anti-CD34 antibody is inserted through the guiding catheter and deployed in the denuded segment of the coronary artery. Bare stainless steel stents or stents coated with the matrix but without antibodies are used as controls. Stents are implanted into either the Left Anterior Descending (LAD) coronary artery or the Right Coronary Artery (RCA) or the Circumflex coronary artery (Cx) at a stent to artery ration of 1.1. The sizing and placement of the stents is evaluated angiographically and the introducer sheath was removed and the skin closed in two layers. Animals are placed on 300 mg of ASA for the duration of the experiment.

Animals are sacrificed at 1, 3, 7, 14, and 28 days after stent implantation. The animals are first sedated and anesthetized as described above. The stented coronary arteries are explanted with 1 cm of non-stented vessel proximal and distal to the stent. The stented arteries are processed in three ways, histology, immunohistochemistry or by Scanning Electron Microscopy.

For immunohistochemistry the dissected stents are gently flushed with 10% Formalin for 30 seconds and the placed in a 10% Formalin/PBS solution until processing. Stents destined for immunohistochemistry are flushed with 2% Paraformaldehyde (PFA) in PBS for 30 seconds and then placed in a 2% PFA solution for 15 min, washed and stored in PBS until immunohistochemistry with rabbit anti-human VEGFR-2 or mouse anti-human Tie-2 antibodies is performed.

Stents are prepared for SEM by flushing with 10% buffered Formalin for 30 seconds followed by fixation with 2% PFA with 2.5% glutaraldehyde in 0.1 M sodium cacodylate buffer overnight. Samples are then washed 3× with cacodylate buffer and left to wash overnight. Post-fixation was completed with 1% osmium tetroxide (Sigma) in 0.1M cacodylate buffer which is followed by dehydration with ethanol (30% ethanol, 50%, 70%, 85%, 95%, 100%, 100%) and subsequent critical point drying with $CO_2$. After drying, samples are gold sputtered and visualized under SEM. (Reduction in thrombotic events with heparin-coated Palmaz-Schatz stents in normal porcine coronary arteries, *Circulation* 93:423-430, incorporated herein by reference).

For histology the stented segments are flushed with 10% buffered Formalin for 30 seconds followed by fixation with 10% buffered Formalin until processed. Five sections are cut from each stent; 1 mm proximal to the stent, 1 mm from the proximal end of the stent, mid stent, 1 mm from the distal edge of the stent and 1 mm distal to the stent. Sections are stained with Hematoxylin & Eosin (HE) and Elastin Trichrome.

FIGS. 14A-14G show explants taken 1 (FIGS. 14A and 14B) and 48 hours (FIGS. 14C-14G) after implantation and observed under scanning electron microscope. The photomicrographs clearly show that the dextran/anti-CD34 antibody-coated stents (14B, 14E-G) have capture progenitor endothelial cells as shown by the spindle-shaped appearance of the cells at higher magnification (400×) at 48 hours compared to the dextran-coated control (14A, 14C and 14D).

Cross-sections of the explants from the swine coronary arteries also showed that the dextran-anti-CD34 antibody-coated (14L, 14M) caused a pronounced inhibition of intimal hyperplasia (thickness of the arterial smooth muscle layer) compared to the controls (bare stainless steel 14H and 14I; dextran-coated 14J and 14K). Fullerene-coated stent implants also inhibit intimal hyperplasia better than bare, control stainless steel stents as shown in FIGS. 13B-13D.

FIGS. 15A and 15B show, respectively, confocal photomicrographs of 48 hours explants of a dextran-plasma coated stent without antibody on is surface, and a dextran-plasma coated anti-CD34 antibody-stent of 18 mm in length. The stents had been implanted into the coronary artery of juvenile male Yorkshire swine. The explants were immunohistochemically processed and stained for VEGFR-2, followed by FITC-conjugated secondary antibody treatment and studied under confocal microscopy. FIGS. 15B and 15C show that the antibody containing stent is covered with endothelial cells as demonstrated by the green fluorescence of the section compared to the complete lack of endothelium on the stent without antibody (FIG. 15A).

Example 6

Incorporation of an Endothelial Growth Factor into Immobilized Antibody Matrices Applied to Stents The following describes the steps for immobilizing an antibody directed toward endothelial progenitor cells cell surface antigens to a biocompatible matrix applied to an intravascular stent to which an endothelial growth factor is then absorbed for the enhanced attachment of circulating endothelial progenitor cells and their maturation to functional endothelium when in contact with blood.

Matrix Deposition: Using methods know to those skilled in the art, stainless steel stents are treated with a plasma deposition to introduce amine functionality on the stent surface. A layer of carboxy functional dextran (CMDX) will be bound to the amine functional layer deposited on the stent through the activation of the CMDX carboxyl groups using standard procedures, known as water soluble carbodiimide coupling chemistry, under aqueous conditions to which the amine groups on the plasma deposited layer to form an amide bond between the plasma layer and the functional CDMX.

Antibody Immobilization: Antibodies directed toward endothelial progenitor cells cell surface antigens, e.g., murine monoclonal anti-humanCD34, will be covalently coupled with the CDMX coated stents by incubation in aqueous water soluble carbodiimide chemistry in a buffered, acidic solution.

Absorption of Growth Factor: Subsequent to the immobilization of the monoclonal anti-humanCD34 to a CMDX matrix applied to a stent, the device is incubated in an aqueous solution of an endothelial growth factor, e.g. Angiopoietin-2, at an appropriate concentration such that the growth factor is absorbed into the CMDX matrix. The treated devices are rinsed in physiologic buffered saline solution and stored in a sodium azide preservative solution.

Using standard angiographic techniques, the above described devices when implanted in porcine coronary arteries and exposure to human blood produce an enhanced uptake and attachment of circulating endothelial progenitor cells on to the treated stent surface and accelerate their maturation into functional endothelium. The rapid establishment of functional endothelium is expected to decrease device thrombogenicity and modulate the extent of intimal hyperplasia.

Example 7

Immobilization of an Endothelial Growth Factor and an Antibody on to Stents

The following describes the steps for immobilizing an antibody directed toward endothelial progenitor cells cell surface antigens and an endothelial growth factor to a biocompatible matrix applied to an intravascular stent for the enhanced attachment of circulating endothelial progenitor cells and their maturation to functional endothelium when in contact with blood.

Matrix Deposition: Matrix Deposition: Using methods know to those skilled in the art, stainless steel stents are treated with a plasma deposition to introduce amine functionality on the stent surface. A layer of carboxy functional dextran (CMDX) is bound to the amine functional layer deposited on the stent through the activation of the CMDX carboxyl groups using standard procedures, known as water soluble carbodiimide coupling chemistry, under aqueous conditions to which the amine groups on the plasma deposited layer to form an amide bond between the plasma layer and the functional CDMX.

Antibody and Growth Factor Immobilization: Antibodies directed toward endothelial progenitor cells cell surface antigens, e.g. murine monoclonal anti-human CD34, and an endothelial growth factor, e.g. Angiopoietin-2, is covalently coupled with the CDMX coated stents by incubation at equimolar concentrations in a water soluble carbodiimide solution under acidic conditions. The treated devices are rinsed in physiologic buffered saline solution and stored in a sodium azide preservative solution.

Using standard angiographic techniques, the above described devices when implanted in porcine coronary arteries and exposure to human blood produce an enhanced uptake and attachment of circulating endothelial progenitor cells on to the treated stent surface and accelerate their maturation into functional endothelium. The rapid establishment of functional endothelium is expected to decrease device thrombogenicity and modulate the extent of intimal hyperplasia.

Example 8

Small Molecule Functionalization of a Stent

Figure 16B:
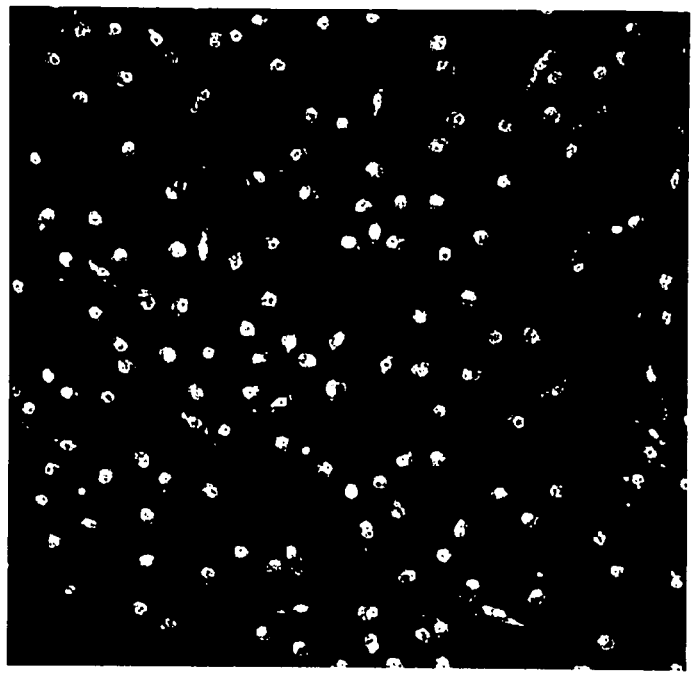
FIGS. 16A and 16B are photomicrographs of a Propidium iodide and anti-lectin/FITC-conjugated sample.
Figure 16A:
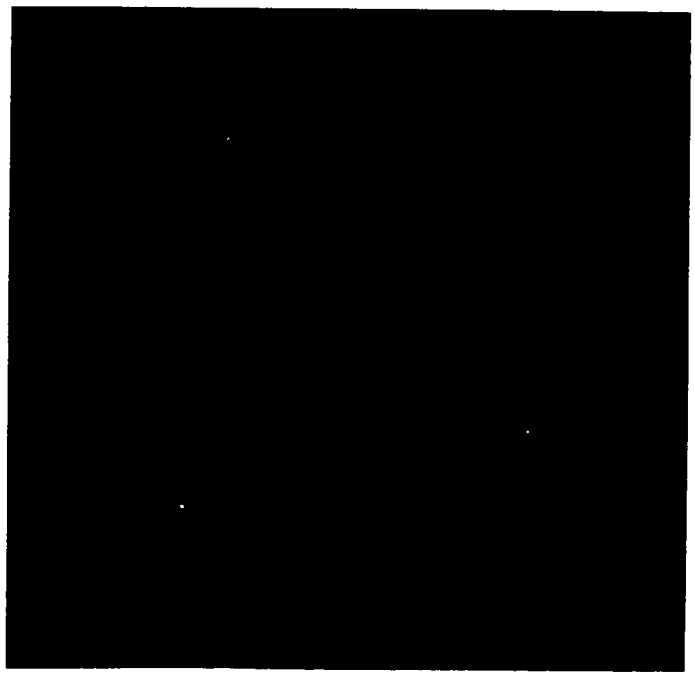

Progenitor endothelial cells were isolated as described in Example 1. The cells were plated in fibronectin-coated slides and grown for 7 days in EBM-2 culture medium. Cells were fixed and stained with Propidium Iodine (PI) and a FITC-conjugated endothelial cell specific lectin. (Ulex Europaeus Uea 1) The results of these experiments are shown in FIGS. 16A and 16B. The figures show that progenitor endothelial cells are bound to the fibronectin-coated slides and that the cells express a ligand for the lectin on their surface.

Example 9

Transfection of Mammalian Cells In Vitro for Use in Blood Vessel Remodeling

Progenitor endothelial cells are transfected using electroporation of a bicistronic plasmid containing genes encoding a protein responsible for the production of adenosine and a prostate specific cell membrane protein. Both genes are under the control of their own promoter, so that the genes are expressed constitutively.

What is claimed is:

1. A method of delivering a stent into a patient, comprising the steps of:
    (i) administering genetically-altered endothelial progenitor cells into the patient, said genetically-altered endothelial progenitor cells comprising exogenous nucleic acid encoding a cell membrane marker molecule not normally found in said genetically-altered endothelial progenitor cells, and at least one therapeutic gene product; said genetically-altered endothelial progenitor cells being capable of expressing said cell membrane marker molecule and said at least one therapeutic gene product, wherein said cell membrane marker molecule is selected from the group consisting of an osteogenic protein, and a prostatic cell membrane protein; and
    (ii) separately administering into said patient a cell-free stent comprising a coating on the lumen surface of the stent; said coating comprising a matrix bearing a covalently attached ligand, wherein said ligand specifically recognizes and binds said cell membrane marker molecule expressed by said genetically-altered endothelial progenitor cells;
    wherein the therapeutic gene product is selected from the group consisting of vascular endothelial growth factor, angiogenin, anti-angiogenic factor, and fibroblast growth factor,
    and wherein said genetically altered endothelial progenitor cells bind to said ligand on said stent in vivo.

2. The method of claim 1, wherein the ligand is selected from the group consisting of antibodies, antibody fragments, combinations of antibodies and antibody fragments thereof.

3. The method of claim 2, wherein the antibodies and/or antibody fragments are monoclonal.

4. The method of claim 1, wherein said exogenous nucleic acid is extrachromosomal or a plasmid.

5. The method of claim 1, wherein said genetically altered endothelial progenitor cells comprise autologous cells.

6. The method of claim 1, wherein said genetically altered endothelial progenitor cells comprise donor or autologous cells.

7. The method of claim 1, wherein said genetically altered endothelial progenitor cells comprise cells harvested from blood.

8. The method of claim 1, wherein said genetically altered endothelial progenitor cells are injected intravenously to said patient.

9. The method of claim 1, wherein said matrix comprises at least a layer of one, or more than one, polymeric compound.

10. The method of claim 9, wherein said one, or more than one, polymeric compound is cross-linked with a cross-linking agent that forms covalent bonds capable of being cleaved by an enzyme under in vivo conditions.

11. The method of claim 9, wherein said one, or more than one, polymeric compound is cross-linked with a cross-linking agent that forms covalent bonds that are capable of non-enzymatic hydrolysis under in vivo conditions.

12. The method of claim 11, wherein said cross-linking agent comprises a compound having at least two reactive functional groups selected from the group consisting of aldehydes, epoxides, acyl halides, alkyl halides, isocyanates, amines, anhydrides, acids, alcohols, haloacetals, aryl carbonates, thiols, esters, imides, vinyls, azides, nitros, peroxides, sulfones, maleimides, poly(acrylic acid), vinyl sulfone, succinyl chloride, polyanhydrides, succinimidyl succinate-polyethylene glycol, and succinimidyl succinamide-polyethylene glycol, amine reactive esters.

13. The method of claim 1, wherein the genetically-altered endothelial progenitor cells are endothelial progenitor or endothelial stem cells derived from human origin.

14. The method of claim 1, wherein the stent further comprises an intimal hyperplasia or restenosis inhibitory compound.

15. The method of claim 14, wherein the compound decreases or inhibits smooth muscle cell migration, smooth muscle cell differentiation, and/or collagen deposition.

16. The method of claim 1, wherein said stent comprises a metal stent.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Sense PCR primer from nitric oxide synthetase
      sequence of endothelial cell origin

<400> SEQUENCE: 1
ttccggggat tctggcagga g                                             21

<210> SEQ ID NO 2
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Antisense PCR primer from nitric oxide
      synthetase sequence of endothelial cell origin

<400> SEQUENCE: 2
gccatggtaa catcgccgca g                                             21

<210> SEQ ID NO 3
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Sense PCR primer for Glyceraldehyde Phosphate
      Dehydrogenase gene

<400> SEQUENCE: 3
ctctaaggct gtgggcaagg tcat                                          24

<210> SEQ ID NO 4
<211> LENGTH: 24
<212> TYPE: DNA
<213> ORGANISM: Homo sapiens

<400> SEQUENCE: 4
gagatccacc accctgttgc tgta                                          24
```